United States Patent [19]
Mackenzie et al.

[11] Patent Number: 5,677,324
[45] Date of Patent: Oct. 14, 1997

[54] BENZOPYRANES AS POTASSIUM CHANNEL OPENERS

[75] Inventors: Alexander Roderick Mackenzie; Sandra Marina Monaghan, both of Sandwich, United Kingdom

[73] Assignee: Pfizer Inc., New York, N.Y.

[21] Appl. No.: 501,080

[22] PCT Filed: Mar. 4, 1994

[86] PCT No.: PCT/EP94/00637

§ 371 Date: Aug. 4, 1995

§ 102(e) Date: Aug. 4, 1995

[87] PCT Pub. No.: WO94/20491

PCT Pub. Date: Sep. 15, 1994

[30] Foreign Application Priority Data

Mar. 10, 1993 [GB] United Kingdom ............... 9304917
Apr. 22, 1993 [GB] United Kingdom ............... 9308368

[51] Int. Cl.$^6$ .......... C07D 405/04; C07D 405/14; A61K 31/41; A61K 31/44
[52] U.S. Cl. .......... 514/382; 514/252; 514/269; 514/274; 514/276; 514/340; 544/238; 544/316; 544/333; 546/243; 546/268.4; 548/252
[58] Field of Search ............ 548/252; 514/382, 514/269, 274, 252, 276, 340; 544/238, 316, 333; 546/268.4, 243

[56] References Cited

FOREIGN PATENT DOCUMENTS 337179 3/1989 European Pat. Off. .
1479518 7/1977 United Kingdom .

OTHER PUBLICATIONS

Bergmann, R. and Gericke, R., J. Med. Chem., 33, 492–503 (1990).

Primary Examiner—Jacqueline Haley
Attorney, Agent, or Firm—Peter C. Richardson; Gregg C. Benson; James T. Jones

[57] ABSTRACT

The present invention relates to compounds of formula (I) and the pharmaceutically acceptable salts thereof, wherein the dashed line represents an optional covalent bond; X is O, NH, S or a direct link; $R^3$ is hydroxy when the dashed line does not represent a covalent bond and $R^3$ is absent when the dashed line represents a covalent bond; $R^4$ is (a), when X is O, a group of formula (i), (b), when X is O, NH or S, optionally substituted hydroxyphenyl, (c) an optionally substituted 4- to 7-membered heterocyclic ring, or (d), when X is NH, a group of formula (ii). The compounds are useful for the treatment of disease associated with the altered tone or motility of smooth muscle.

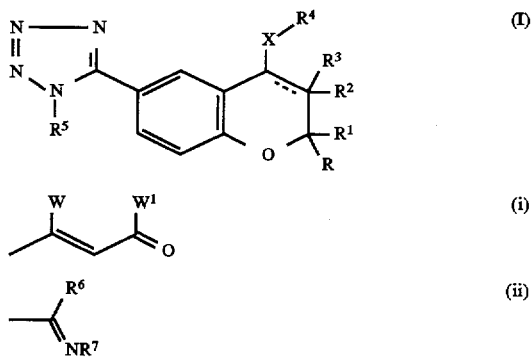

13 Claims, No Drawings

BENZOPYRANES AS POTASSIUM CHANNEL OPENERS

This is a National Stage application of PCT/EP94/00637 filed Mar. 4, 1994 and published as WO94/20491 on Sep. 15, 1994.

The present invention relates to benzopyrans. More particularly it relates to 6-(tetrazol-5-yl)benzo[b]pyran derivatives and to compositions containing, uses of, processes for the preparation of and intermediates used in the preparation of, such derivatives.

The present derivatives display smooth muscle relaxant activity by a mechanism involving potassium channel opening. They are therefore useful in the curative or prophylactic treatment of diseases associated with the altered tone and/or motility of smooth muscle which can, for example, occur in the lung, bladder, gut, uterus or cardiovascular system. Such diseases include chronic obstructive airways disease, asthma, urinary incontinence, irritable bowel syndrome, diverticular disease, oesophageal achalasia and hypertension. In addition, the present derivatives may be useful in the treatment of peripheral vascular disease, congestive heart failure, pulmonary hypertension, myocardial and cerebral ischaemia, angina, male pattern baldness, cardiac arrhythmia, skeletal muscle fatigue/paralysis (myotonic muscular dystrophy), glaucoma, epilepsy, tinnitus, vertigo and dysmenorrhoea.

The present invention provides compounds of the formula:

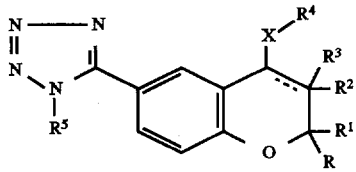

(I)

and the pharmaceutically acceptable salts thereof, wherein the dashed line represents an optional covalent bond;

X is O, NH, S or a direct link;

R and $R^1$ are either each independently selected from H, fluoro($C_1$–$C_4$)alkyl and $C_1$–$C_4$ alkyl or taken together represent $C_2$–$C_6$ alkylene;

$R^2$ is H or $C_1$–$C_4$ alkyl;

$R^3$ is hydroxy when the dashed line does not represent a covalent bond and $R^3$ is absent when the dashed line represents a covalent bond;

$R^4$ is (a), when X is O, a group of the formula:

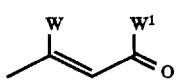

wherein W and $W^1$ taken together represent $C_1$–$C_4$ alkylene, said alkylene being optionally benzo-fused when W and $W^1$ taken together represent $C_2$–$C_4$ alkylene, and optionally substituted, including in the benzo-fused portion, by $C_1$–$C_6$ alkyl, hydroxy, —$OR^8$, halo, —$N(R^8)_2$, —$SR^8$ or halo($C_1$–$C_4$)alkyl, (b), when X is O, NH or S, hydroxyphenyl optionally substituted by $C_1$–$C_6$ alkyl, —$OR^8$, halo, —$N(R^8)_2$, —$SR^8$ or halo($C_1$–$C_4$)alkyl, (c) a 4- to 7-membered heterocyclic ring containing either from 1 to 3 N hetero-atoms or one N hetero-atom and one O or one S hetero-atom, said ring being optionally benzo- or $C_3$–$C_7$ cycloalkyl-fused and optionally substituted, including in the benzo- or $C_3$–$C_7$ cycloalkyl-fused portion, by $C_1$–$C_6$ alkyl, hydroxy, hydroxy($C_1$–$C_4$)alkyl, —$OR^8$, $R^8O$ ($C_1$–$C_4$)alkyl, halo, halo($C_1$–$C_4$)alkyl, —$S(O)_mR^8$, $R^8S(O)_m$($C_1$–$C_4$)alkyl, oxo, N-cyanoimino, amino, amino($C_1$–$C_4$) alkyl, —$NHR^8$, $R^8NH(C_1$–$C_4)$alkyl, —$N(R^8)_2$, $(R^8)_2N$ ($C_1$–$C_4$)alkyl, cyano, cyano($C_1$–$C_4$)alkyl, —$CO_2R^8$, $R^8O_2C$ ($C_1$–$C_4$)alkyl, —$CONH_2$, $H_2NCO(C_1$–$C_4)$alkyl, —$CONHR^8$, $R^8NHCO(C_1$–$C_4)$alkyl, —$CON(R^8)_2$ or $(R^8)_2NCO(C_1$–$C_4)$alkyl, or, as appropriate, a ring N- or S-oxide derivative of said heterocyclic ring, with the proviso that said heterocyclic ring is linked by a ring carbon atom when X is O, NH or S, or (d), when X is NH, a group of the formula:

wherein $R^6$ is —$OR^8$, —$NHR^8$, —$SR^8$, —NH(aryl) or —NH(pyridinyl) and $R^7$ is cyano, nitro or $C_2$–$C_6$ alkanoyl;

$R^5$ is aryl, $C_1$–$C_{12}$ alkyl, $C_2$–$C_{12}$ alkenyl or $C_2$–$C_{12}$ alkynyl, said $C_1$–$C_{12}$ alkyl, $C_2$–$C_{12}$ alkenyl and $C_2$–$C_{12}$ alkynyl being optionally substituted by $C_4$–$C_7$ cycloalkyl, hydroxy, —$OR^8$, $C_2$–$C_6$ alkanoyloxy, halo, cyano, nitro, amino, —$NHR^8$, —$N(R^8)_2$, —$S(O)_mR^8$, —$NHSO_2R^8$, —$NHCOR^8$, —$COR^8$, —$CONH_2$, —$CONHR^8$, —$CON(R^8)_2$, —$OCO_2R^8$, —$CONH(C_1$–$C_6)$alkyl$CO_2R^8$, —$CONR^8(C_1$–$C_6)$alkyl$CO_2R^8$, —$CO_2R^9$, aryl, aryloxy, arylcarbonyl, arylcarbonyloxy, aryl($C_1$–$C_6$)alkoxy, aryl ($C_1$–$C_6$)alkoxycarbonyl, phthalimido, or a group of the formula:

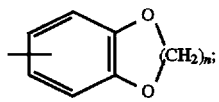

$R^8$ is $C_1$–$C_6$ alkyl;

$R^9$ is indanyl, aryl, $C_1$–$C_{12}$ alkyl, $C_2$–$C_{12}$ alkenyl or $C_2$–$C_{12}$ alkynyl, said $C_1$–$C_{12}$ alkyl, $C_2$–$C_{12}$ alkenyl and $C_2$–$C_{12}$ alkynyl being optionally substituted by $C_4$–$C_7$ cycloalkyl, hydroxy, —$OR^8$, $C_2$–$C_6$ alkanoyloxy, halo, cyano, nitro, amino, —$NHR^8$, —$N(R^8)_2$, —$S(O)_mR^8$, —$NHSO_2R^8$, —$NHCOR^8$, —$COR^8$, —$CONH_2$, —$CONHR^8$, —$CON(R^8)_2$, —$OCO_2R^8$, —$CONH(C_1$–$C_6)$ alkyl$CO_2R^8$, —$CONR^8(C_1$–$C_6)$alkyl$CO_2R^8$, —$CO_2$ ($C_1$–$C_{12}$ alkyl), aryl, aryloxy, arylcarbonyl, arylcarbonyloxy, aryl($C_1$–$C_6$)alkoxy, aryl($C_1$–$C_6$)alkoxycarbonyl, phthalimido, or a group of the formula:

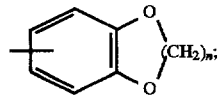

"aryl", used in the definitions of $R^5$, $R^6$ and $R^9$ and in this definition, means phenyl optionally substituted by $C_1$–$C_6$ alkyl, $C_2$–$C_6$ alkenyl, $C_2$–$C_6$ alkynyl, hydroxy, hydroxy ($C_1$–$C_6$)alkyl, —$OR^8$, $R^8O(C_1$–$C_6)$alkyl, $R^8O(C_1$–$C_6)$ alkoxy, $R^8O(C_1$–$C_6)$alkoxy($C_1$–$C_6)$alkyl, halo, halo($C_1$–$C_6$) alkyl, cyano, cyano($C_1$–$C_6$)alkyl, nitro, nitro($C_1$–$C_6$)alkyl, amino, amino($C_1$–$C_6$)alkyl, —$NHR^8$, $R^8NH(C_1$–$C_6)$alkyl, —$N(R^8)_2$, $(R^8)_2N(C_1$–$C_6)$alkyl, —$S(O)_mR^8$, $R^8S(O)_m$ ($C_1$–$C_6$) alkyl, —$NHCOR^8$, $R^8CONH(C_1$–$C_6)$alkyl, —$COR^8$, $R^8CO(C_1$–$C_6)$alkyl, —$CONH_2$, $H_2NCO(C_1$–$C_6)$ alkyl, —$CONHR^8$, $R^8NHCO(C_1$–$C_6)$alkyl, —$CON(R^8)_2$, $(R^8)_2NCO(C_1$–$C_6)$alkyl, —$CONH(C_1$–$C_6)$alkyl$CO_2R^8$, $R^8O_2C(C_1-C_6)$alkylNHCO$(C_1-C_6)$alkyl, —CONR$^8$ $(C_1-C_6)$alkyl CO$_2R^8$, $R^8O_2C(C_1-C_6)$alkylNR$^8$CO$(C_1-C_6)$alkyl, —CO$_2R^{9A}$, $R^{9A}O_2C(C_1-C_6)$alkyl, aryl, aryl$(C_1-C_6)$alkyl, aryl$(C_1-C_6)$alkoxy or aryl$(C_1-C_6)$alkoxy$(C_1-C_6)$alkyl;

$R^{9A}$ is indanyl, phenyl, $C_1-C_{12}$ alkyl, $C_2-C_{12}$ alkenyl or $C_2-C_{12}$ alkynyl, said $C_1-C_{12}$ alkyl, $C_2-C_{12}$ alkenyl and $C_2-C_{12}$ alkynyl being optionally substituted as previously defined for those definitions for $R^9$ and said phenyl being optionally substituted by from 1 to 3 substituents each independently selected from $C_1-C_6$ alkyl, hydroxy, —OR$^8$, halo, halo$(C_1-C_6)$alkyl, nitro and cyano;

m is 0, 1 or 2; and n is 1, 2 or 3.

In the above definitions, the term "halo" means fluoro, chloro, bromo or iodo and alkyl, alkenyl and alkoxy groups containing three or more carbon atoms together with alkynyl and alkanoyl groups containing four or more carbon atoms can be straight- or branched-chain.

Preferably the dashed line does not represent a covalent bond.

Preferably X is O, NH or a direct link.

Most preferably X is O.

Preferably R and R$^1$ are each independently selected from H and $C_1-C_4$ alkyl.

More preferably R and R$^1$ are both $C_1-C_4$ alkyl.

Most preferably R and R$^1$ are both methyl.

Preferably R$^2$ is H or methyl.

Most preferably R$^2$ is methyl.

Preferably R$^2$ is methyl, R$^3$ is hydroxy and the dashed line does not represent a covalent bond.

Preferably R$^4$ is a group of the formula:

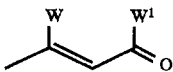

wherein W and W$^1$ taken together represent $C_1-C_4$ alkylene, a 6-membered heterocyclic ring containing 1 or 2 nitrogen hetero-atoms and optionally substituted by $C_1-C_6$ alkyl, hydroxy, halo, $C_1-C_4$ alkylthio or oxo, or is a group of the formula:

wherein R$^6$ is —OR$^8$, —NHR$^8$ or —SR$^8$ and R$^7$ is cyano. More preferably R$^4$ is 1-oxocyclopent-2-en-3-yl, 2-oxo-1,2-dihydropyridin-1-yl, 2-oxo-1H-1,2-dihydropyridin-4-yl, 2-oxopiperidin-1-yl, 3-hydroxypyridazin-6-yl, 2-methyl-3-oxopyridazin-6-yl, 4-chloropyrimidin-2-yl, 2-chloropyrimidin-4-yl, 2-methylthiopyrimidin-4-yl or is a group of the formula:

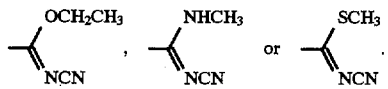

Most preferably R$^4$ is 3-hydroxypyridazin-6-yl.

Preferably R$^5$ is aryl or $C_1-C_{12}$ alkyl, said $C_1-C_{12}$ alkyl being optionally substituted by hydroxy, —OR$^8$, $C_2-C_6$ alkanoyloxy, amino, —CONHR$^8$, —CONH$(C_1-C_6)$alkylCO$_2R^8$, —CO$_2R^9$, aryl, aryloxy, arylcarbonyloxy, aryl$(C_1-C_6)$alkoxy, phthalimido, or a group of the formula:

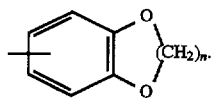

More preferably R$^5$ is phenyl or $C_1-C_4$ alkyl, said $C_1-C_4$ alkyl being optionally substituted by hydroxy, methoxy, acetoxy, amino, methylaminocarbonyl, N-(ethoxycarbonylmethyl)carbamoyl, —CO$_2R^9$, phenyl, methylphenyl, methoxyphenyl, hydroxyphenyl, halophenyl, benzyloxyphenyl, phenoxy, benzoyloxy, benzyloxy, phthalimido, or a group of the formula:

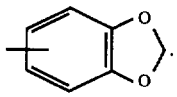

Yet more preferably R$^5$ is phenyl, methyl, ethyl, n-propyl, 2-hydroxyethyl, 2-methoxyethyl, 2-acetoxyethyl, 2-aminoethyl, 2-(methylaminocarbonyl)ethyl, N-(ethoxycarbonylmethyl)carbamoylmethyl, ethoxycarbonylmethyl, 3-methoxycarbonylprop-1-yl, 3-ethoxycarbonylmethyl, 3-methoxycarbonylprop-1-yl, 3-ethoxycarbonylprop-1-yl, 4-ethoxycarbonylbut-1-yl, 3-vinyloxycarbonylprop-1-yl, 3-(2,2,2-trifluoroethoxycarbonyl)prop-1-yl, 3-(ethoxycarbonyloxymethoxycarbonyl)prop-1-yl, 3-(pivaloyloxymethoxycarbonyl)prop-1-yl, 3-phenoxycarbonylprop-1-yl, 3-benzyloxycarbonylprop-1-yl, 3-(5-indanyloxycarbonyl)-prop-1-yl, benzyl, 2-phenylethyl, 3-phenylprop-1-yl, 4-phenylbut-1-yl, 2-(2-methylphenyl)ethyl, 2-(3-methylphenyl)ethyl, 2-(4-methylphenyl)ethyl, 2-(2-methoxyphenyl)ethyl, 2-(3-methoxyphenyl)-ethyl, 2-(4-methoxyphenyl)ethyl, 2-(4-hydroxyphenyl)ethyl, 2-(4-fluorophenyl)ethyl, 2-(4-benzyloxyphenyl)ethyl, 2-phenoxyethyl, 2-benzoyloxyethyl, 2-benzyloxyethyl, 2-phthalimidoethyl or 2-(1,3-benzodioxolan-5-yl)ethyl.

Most preferably R$^5$ is methyl, ethyl, n-propyl, 3-ethoxycarbonylprop-1-yl, 4-ethoxycarbonylbut-1-yl or 2-phenylethyl.

Preferably R$^8$ is methyl or ethyl.

Preferably R$^9$ is indanyl, aryl, $C_1-C_{12}$ alkyl or $C_2-C_{12}$ alkenyl, said $C_1-C_{12}$ alkyl being optionally substituted by halo, $C_2-C_6$ alkanoyloxy, —OCO$_2R^8$ or aryl.

More preferably R$^9$ is indanyl, phenyl, $C_1-C_4$ alkyl or vinyl, said $C_1-C_4$ alkyl being optionally substituted by fluoro, pivaloyloxy, ethoxycarbonyloxy or phenyl, as, preferably, is $R^{9A}$. Most preferably R$^9$ is 5-indanyl, phenyl, methyl, ethyl, vinyl, 2,2,2-trifluoroethyl, pivaloyloxymethyl, ethoxycarbonyloxymethyl or benzyl, as, most preferably, is $R^{9A}$.

Preferably "aryl" means phenyl optionally substituted by $C_1-C_6$ alkyl, hydroxy, —OR$^8$, halo or aryl$(C_1-C_6)$alkoxy. More preferably "aryl" means phenyl optionally substituted by methyl, hydroxy, methoxy, fluoro or benzyloxy. Most preferably "aryl" means phenyl, 2-methylphenyl, 3-methylphenyl, 4-methylphenyl, 4-hydroxyphenyl, 2-methoxyphenyl, 3-methoxyphenyl, 4-methoxyphenyl, 4-fluorophenyl or 4-benzyloxyphenyl.

Preferably m is 0.

Preferably n is 1.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, bisulphate, phosphate, hydrogen phosphate, acetate, maleate, fumarate, lactate, tartrate, citrate, gluconate, benzoate, methanesulphonate, benzenesulphonate and p-toluenesulphonate salts.

Suitable base salts are formed from bases which form non-toxic salts and examples are the aluminium, calcium, lithium, magnesium, potassium, sodium, zinc and diethanolamine salts.

For a review on suitable salts see Berge et al, J. Pharm. Sci., 66, 1–19 (1977).

A compound of the formula (I) may contain one or more asymmetric carbon atoms and/or one or more alkenyl groups and may therefore exist in two or more stereoisomeric forms. The present invention includes the individual stereoisomers of the compounds of the formula (I) and mixtures thereof, together, where appropriate, with all the tautomeric forms of the compounds of the formula (I).

Separation of diastereoisomers or cis and trans isomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base.

A preferred group of compounds of the formula (I) is where the dashed line does not represent a covalent bond, X is O or NH, R and $R^1$ are both $C_1$–$C_4$ alkyl, $R^2$ is H or $C_1$–$C_4$ alkyl, $R^3$ is hydroxy and $R^4$ and $R^5$ are as previously defined for a compound of the formula (I), and which has the (3S,4R)- stereochemistry in the benzopyran ring, that is a compound of the formula:

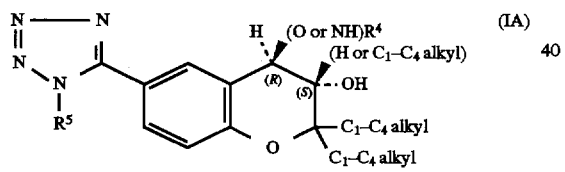

(IA)

The compounds of the formula (I) provided by the invention can be prepared by the following methods:

1) The compounds of the formula (I) wherein the dashed line does not represent a covalent bond, X is O, NH or S, $R^4$ has the definition (a), (b) or (c) as previously defined for $R^4$ for a compound of the formula (I) and R, $R^1$, $R^2$, $R^3$ and $R^5$ are as previously defined for a compound of the formula (I), can be prepared by reacting a compound of the formula:

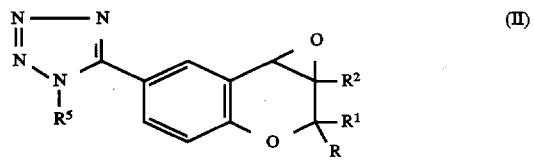

(II)

wherein R, $R^1$, $R^2$ and $R^5$ are as defined for this method, with a compound of the formula:

$R^4$—XH or, where appropriate, a tautomer thereof, or, where X is O or S, with a base salt thereof, wherein $R^4$ and X are as defined for this method. Preferred base salts of the compounds of the formula $R^4$—XH include the alkali metal salts, e.g. the sodium and potassium salts. If a base salt is used, this may be generated in situ from the corresponding compound of the formula $R^4$—XH using a suitable base, e.g. sodium hydride.

The reaction is typically carried out in a suitable organic solvent, e.g. ethanol or tetrahydrofuran, at from room temperature to, and preferably at, the reflux temperature of the solvent. If a base salt of a compound of the formula $R^4$—XH is not used, a suitable base catalyst, e.g. pyridine or triethylamine, may also be present.

If a base salt of a compound of the formula $R^4$—XH wherein X is O and $R^4$ is as previously defined in definition (a) for $R^4$ for a compound of the formula (I) is used, the reaction is preferably carried out in the presence of a suitable Lewis acid, e.g. boron trifluoride etherate.

The intermediates of the formula (II) can be prepared by the following route:

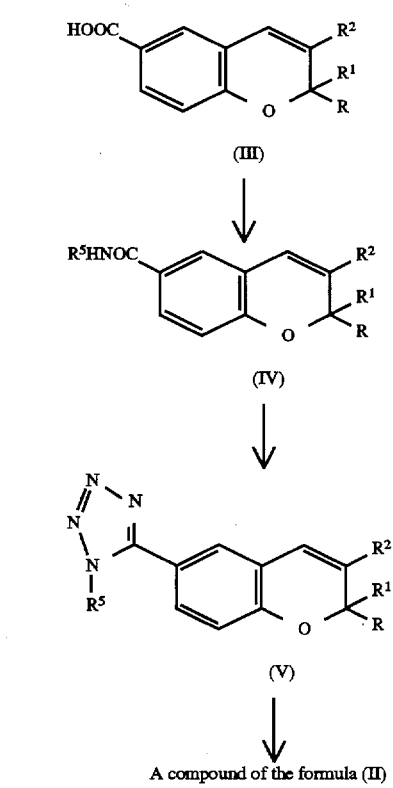

A compound of the formula (II)

wherein R, $R^1$, $R^2$ and $R^5$ are as defined for this method.

In a typical procedure a carboxylic acid of the formula (III) is converted to an amide of the formula (IV) using a conventional procedure, e.g. by reacting the carboxylic acid with 1,1'-carbonyldiimidazole to first form an imidazolide derivative, followed by reaction of this derivative with an amine of the formula $R^5NH_2$, wherein $R^5$ is as defined for this method. Alternatively the carboxylic acid can be converted to the corresponding acid chloride, e.g. using oxalyl chloride in the presence of N,N-dimethylformamide, which can then be reacted with an amine of the formula $R^5NH_2$ to provide the required amide.

The amide of the formula (IV) is reacted first with phosphorus pentachloride and then with trimethylsilyl azide to form a tetrazole of the formula (V) that can be converted to an epoxide of the formula (II) using sodium hypochlorite in the presence of [(S,S)-1,2-bis(3,5-di-tert-butylsalicylideamino)]-cyclohexane manganese (III) chloride (see J. Amer. Chem. Soc., 113, 7063 (1991)) or by using OXONE™ (potassium peroxymonosulphate).

The intermediates of the formulae (III) and $R^4$—XH, and the base salts thereof, are either known or may be prepared by conventional techniques.

Alternatively, where $R^2$ is H, a compound of the formula (V) can be converted to an epoxide of the formula (II) by a two-stage procedure, the first stage involving reacting a compound of the formula (V) with N-bromosuccinimide in aqueous dimethyl sulfoxide to form a 3-bromo-4-hydroxy-2H-benzo[b]pyran derivative and the second stage involving further reacting this bromohydrin derivative with a strong base, e.g. sodium hydride, to form the epoxide.

2) The compounds of the formula (I) wherein the dashed line does not represent a covalent bond, X is a direct link, $R^4$ is an N-linked heterocyclic ring as previously defined in definition (c) for $R^4$ for a compound of the formula (I), and R, $R^1$, $R^2$, $R^3$ and $R^5$ are as previously defined for a compound of the formula (I), can be prepared by reacting a compound of the formula (II), wherein R, $R^1$, $R^2$ and $R^5$ are as previously defined for this method, with a 4- to 7-membered ring heterocyclic compound containing at least one N hetero-atom bearing a hydrogen substituent and which otherwise is as defined in this method for $R^4$, or with a base salt thereof.

In a typical procedure, when a base salt of the heterocyclic compound is not used, the reaction is carried out in the presence of a suitable basic catalyst, e.g. benzyltrimethylammonium hydroxide (TRITON™B) or pyridine, and in a suitable solvent, e.g. dioxan or ethanol, at from room temperature to, and preferably at, the reflux temperature thereof.

When a base salt of the heterocyclic compound is used the preferred base salts include the alkali metal salts, e.g. the sodium and potassium salts. The base salt may be generated in situ by first reacting the heterocyclic compound with a suitable strong base, e.g. sodium hydride, and then allowing the base salt formed to react with a compound of the formula (II).

3) All the compounds of the formula (I) can be prepared by reaction of a compound of the formula:

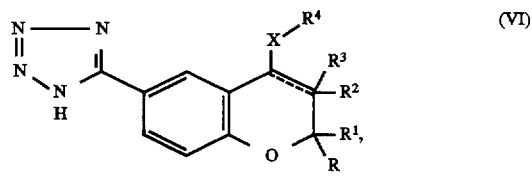

or a base salt thereof, wherein the dashed line, X, R, $R^1$, $R^2$, $R^3$ and $R^4$ are as previously defined for a compound of the formula (I), with a compound of the formula $R^5Z$ wherein $R^5$ is as previously defined for a compound of the formula (I) and Z is a suitable leaving group, e.g. halo (preferably bromo or iodo), methanesulphonyloxy, p-toluenesulphonyloxy or trifluoromethanesulphonyloxy.

Preferred base salts of the compounds of the formula (VI) include the alkali metal salts, e.g. the sodium salt. The base salt may be generated in situ by reaction of a 1H-tetrazole of the formula (VI) with a suitable base, e.g. sodium hydroxide or sodium t-butoxide.

Where a base salt of a compound of the formula (VI) is not used, the alkylation may be carried out in the presence of bis(tributyl)tin oxide and optionally in a suitable solvent, e.g. acetonitrile or N,N-dimethylformamide, at room temperature.

Alternatively, where a base salt of a compound of the formula (VI) is not used, the alkylation may be carried out in the presence of a suitable acid acceptor, e.g. potassium carbonate, and in a suitable solvent, e.g. acetonitrile.

The compounds of the formula (I) where $R^5$ is aryl (e.g. phenyl) can be prepared by reacting a base salt, e.g. a sodium salt, of a compound of the formula (VI) with a diaryliodonium halide, e.g. diphenyliodonium chloride where $R^5$ is phenyl is required. The reaction is typically carried out in a suitable solvent, e.g. t-butanol, and at the reflux temperature thereof.

The intermediate tetrazoles of the formula (VI) can be prepared by reacting a compound of the formula:

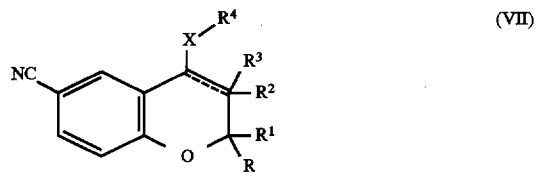

wherein the dashed line, X, R, $R^1$, $R^2$, $R^3$ and $R^4$ are as previously defined for this method, with sodium azide and triethylamine hydrochloride. The reaction is typically carried out in a suitable solvent, e.g. 1-methyl-2-pyrrolidinone, and at an elevated temperature, e.g. ca. 150° C.

4) The compounds of the formula (I) wherein the dashed line represents a covalent bond and X, R, $R^1$, $R^2$, $R^4$ and $R^5$ are as previously defined for a compound of the formula (I), can be prepared by dehydration of a compound of the formula (I) wherein the dashed line does not represent a covalent bond, $R^3$ is hydroxy, and X, R, $R^1$, $R^2$, $R^4$ and $R^5$ are as defined for this method.

In a typical procedure the dehydration is carried out using a suitable dehydrating agent, e.g. polymer-supported sodium hydroxide, and using a suitable solvent, e.g. anhydrous dioxan, at from room temperature to, and preferably at, the reflux temperature thereof.

5) The compounds of the formula (I) wherein the dashed line does not represent a covalent bond, X is a direct link, $R^4$ is 2-oxopiperidin-1-yl optionally substituted as previously defined in definition (c) for $R^4$ for a compound of the formula (I), and R, $R^1$, $R^2$, $R^3$ and $R^5$ are as previously defined for a compound of the formula (I), can be prepared by reduction of a compound of the formula (I) wherein $R^4$ is 2-oxopyridin-1-yl, optionally substituted as defined for $R^4$ for this method and the dashed line, X, R, $R^1$, $R^2$, $R^3$ and $R^5$ are as defined for this method.

The reduction is typically carried out by catalytic hydrogenation of a compound of the formula (I), e.g. using palladium-on-carbon as a catalyst, in a suitable solvent, e.g. ethanol.

6) The compounds of the formula (I) wherein $R^5$ is aryl, $C_1$–$C_{12}$ alkyl, $C_2$–$C_{12}$ alkenyl or $C_2$–$C_{12}$ alkynyl, said alkyl, alkenyl and alkynyl being substituted by —$CO_2R^9$ or by aryl substituted by —$CO_2R^{9A}$ or $R^{9A}O_2C(C_1$–$C_6)$alkyl, and said aryl being substituted by —$CO_2R^{9A}$ or $R^{9A}O_2C(C_1$–$C_6)$ alkyl, and the dashed line, X, R, $R^1$, $R^2$, $R^3$, $R^4$, $R^9$ and "aryl" are as previously defined for a compound of the formula (I), can be prepared by reaction of a compound of the formula:

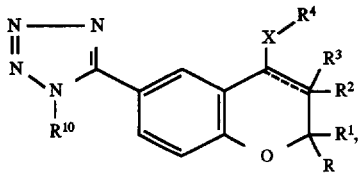

(VIII)

wherein the dashed line, X, R, $R^1$, $R^2$, $R^3$ and $R^4$ are as defined for this method and $R^{10}$ is aryl, $C_1-C_{12}$ alkyl, $C_2-C_{12}$ alkenyl or $C_2-C_{12}$ alkynyl, said alkyl, alkenyl and alkynyl being substituted by —$CO_2H$ or by aryl substituted by —$CO_2H$ or $HO_2C(C_1-C_6)$alkyl, and said aryl being substituted by —$CO_2H$ or $HO_2C(C_1-C_6)$alkyl, or an activated derivative of such a carboxylic acid, with a compound of the formula $R^9OH$ or $R^{9A}OH$, as appropriate, wherein $R^9$ and $R^{9A}$ are as defined for this method.

The term "activated derivative" includes the corresponding acid halide, e.g. acid chloride, imidazolide and activated ester, e.g. benzotriazol-1-yl ester, derivatives of a carboxylic acid of the formula (VIII).

The reaction is typically carried out by reacting a carboxylic acid of the formula (VIII) with oxalyl chloride to form the corresponding acid chloride that may then be reacted with an alcohol of the formula $R^9OH$, optionally in the presence of a suitable acid acceptor, e.g. pyridine, to provide the required ester.

The reaction may also be carried out using conventional esterification conditions, e.g. by reacting a carboxylic acid of the formula (VIII) with an alcohol of the formula $R^9OH$ in the presence of an acid catalyst.

The reaction can further be carried out by reacting a carboxylic acid of the formula (VIII) with an alcohol of the formula $R^9OH$ in the presence of suitable condensing agent, e.g. 1-(3-dimethylaminopropyl)-3-ethylcarbodiimide or dicyclohexylcarbodiimide. A variation on this reaction is to first react a carboxylic acid of the formula (VIII) with 1-hydroxybenzotriazole in the presence of a suitable condensing agent to form an activated ester, that can then be reacted with an alcohol of the formula $R^9OH$ to provide the required ester.

The reaction can yet further be carried out under the conditions of the Mitsunobu reaction by reacting a carboxylic acid of the formula (VIII) with an alcohol of the formula $R^9OH$ in the presence of a suitable phosphine, e.g. triphenylphosphine, and a di($C_1-C_4$)alkyl azodicarboxylate e.g. diethyl azodicarboxylate.

The carboxylic acid intermediates of the formula (VIII) can be prepared by hydrolysis of a corresponding ester of the formula (I), e.g. a methyl or ethyl ester, using conventional conditions, e.g. using aqueous acid or base.

7) The compounds of the formula (I) wherein the dashed line, X, R, $R^1$, $R^2$, $R^3$, $R^4$ and $R^5$ are as defined for method (6) and $R^9$ is vinyl, can be prepared by reaction of a compound of the formula (VIII) wherein the dashed line, X, R, $R^1$, $R^2$, $R^3$ and $R^4$ are as defined for this method and $R^{10}$ is aryl, $C_1-C_{12}$ alkyl, $C_2-C_{12}$ alkenyl or $C_2-C_{12}$ alkynyl, said alkyl, alkenyl and alkynyl being substituted by —$CO_2H$ or by aryl substituted by —COOH or $HO_2C(C_1-C_6)$alkyl, and said aryl being substituted by —COOH or $HO_2C(C_1-C_6)$alkyl, with a vinyl $C_1-C_4$ alkanoate, e.g. vinyl acetate, and in the presence of a suitable catalyst, e.g. 1,10-phenanthrolinylpalladium (II) acetate.

In a typical procedure the reaction is carried out in a suitable solvent, e.g. dichloromethane or tetrahydrofuran, and at an elevated temperature, e.g. at the reflux temperature of the solvent.

8) The compounds of the formula (I) wherein the dashed line, X, R, $R^1$, $R^2$, $R^3$, $R^4$ and $R^5$ are as defined for method (6) and $R^9$ is $C_1-C_{12}$ alkyl optionally substituted as previously defined for the definition of $R^9$ as $C_1-C_{12}$ alkyl for a compound of the formula (I), can be prepared by reaction of a compound of the formula (VIII), or a base salt thereof, wherein the dashed line, X, R, $R^1$, $R^2$, $R^3$, $R^4$ and $R^{10}$ are as defined for a compound of the formula (VIII) in method (7), with a compound of the formula:

$R^9Z^1$ wherein $Z^1$ is a suitable leaving group, e.g. halo, and $R^9$ is as defined for this method.

In a typical procedure a carboxylic acid of the formula (VIII) is reacted with a compound of the formula $R^9Z^1$ wherein $Z^1$ is halo, preferably chloro, in the presence of an alkali metal (e.g. cesium) carbonate and in a suitable solvent, e.g. N,N-dimethylacetamide.

Suitable base salts of the compounds of the formula (VIII) are the alkali metal salts, e.g. the caesium, sodium and potassium salts.

For certain compounds of the formula $R^9Z^1$, the reaction may be conveniently carried out by reaction with a carboxylic acid of the formula (VII) in the presence of a suitable acid acceptor.

9) The compounds of the formula (I) wherein the dashed line does not represent a covalent bond, X is a direct link, $R^4$ is a C-linked heterocyclic ring as previously defined in definition (c) for $R^4$ for a compound of the formula (I), and R, $R^1$, $R^2$, $R^3$ and $R^5$ are as previously defined for a compound of the formula (I), can be prepared by reacting a compound of the formula (II) wherein R, $R^1$, $R^2$ and $R^5$ are as previously defined for this method, with an organometallic compound of the formula:

$R^4M$ wherein $R^4$ is a C-linked heterocyclic ring as defined for $R^4$ for this method and M is a suitable metal, e.g. lithium, sodium or potassium, or metal halide, e.g. a magnesium halide (i.e. a Grignard reagent).

The organometallic compounds of the formula:

$R^4M$ wherein M is a suitable metal are preferably generated in situ by deprotonation of the corresponding heterocyclic compound of the formula:

wherein $R^4$ is as previously defined for this method, with a suitable base, e.g. n- or t-butyl lithium or lithium diisopropylamide.

The organometallic compounds of the formula:

$R^4M$ wherein M is a suitable metal halide, e.g. a magnesium halide, can be prepared by treatment of the corresponding organometallic compound of the formula:

$R^4M$ wherein M is lithium, in situ with a metal halide, e.g. magnesium bromide.

The reaction is typically carried out under an inert atmosphere of nitrogen or argon and in a suitable solvent, e.g. tetrahydrofuran. The reaction step with the epoxide is typically carried out at from −80° C. to the reflux temperature of the solvent, and preferably at from 0° C. to room temperature.

10) The compounds of the formula (I) wherein $R^5$ is $C_1$–$C_{12}$ alkyl, $C_2$–$C_{12}$ alkenyl or $C_2$–$C_{12}$ alkynyl, said alkyl, alkenyl and alkynyl being substituted by $C_2$–$C_6$ alkanoyloxy or arylcarbonyloxy, and "aryl", the dashed line, X, R, $R^1$, $R^2$, $R^3$ and $R^4$ are as previously defined for a compound of the formula (I), can be prepared by reaction of a compound of the formula (I) wherein the dashed line, X, R, $R^1$, $R^2$, $R^3$ and $R^4$ are as defined for this method and $R^5$ is $C_1$–$C_{12}$ alkyl, $C_2$–$C_{12}$ alkenyl or $C_2$–$C_{12}$ alkynyl, said alkyl, alkenyl and alkynyl being substituted by hydroxy, either with a $C_2$–$C_6$ alkanoic acid or arylcarboxylic acid, or with an activated derivative of either of these carboxylic acids, wherein "aryl" is as defined for this method.

The term "activated derivative" includes the corresponding acid halides, e.g. acid chloride, acid anhydride, imidazolide and activated ester, e.g. a benzotriazol-1-yl ester, derivatives of the carboxylic acid.

The reaction can be carried out by reacting a $C_2$–$C_6$ alkanoyl halide or aroyl halide, e.g. a $C_2$–$C_6$ alkanoyl chloride or aroyl chloride, with an alcohol of the formula (I), optionally in the presence of a suitable acid acceptor, e.g. pyridine.

The reaction can also be carried out by reacting an acid anhydride of the formula ($C_2$–$C_6$ alkanoyl)$_2$O or (aroyl)$_2$O with an alcohol of the formula (I), optionally in the presence of a suitable acid acceptor, e.g. pyridine.

The reaction can further be carried out by reaction of an alcohol of the formula (I) and an above carboxylic acid under conventional esterification conditions such as in the presence of a suitable condensing agent or under the conditions of the Mitsunobu reaction, using similar procedures to those described in method (6).

11) The compounds of the formula (I) wherein $R^5$ is aryl, $C_1$–$C_{12}$ alkyl, $C_2$–$C_{12}$ alkenyl or $C_2$–$C_{12}$ alkynyl, said alkyl, alkenyl and alkynyl being substituted by —CONH$_2$, —CONHR$^8$, —CON(R$^8$)$_2$, —CONH(C$_1$–C$_6$)alkylCO$_2$R$^8$ or —CONR$^8$(C$_1$–C$_6$)alkylCO$_2$R$^8$, or by aryl substituted by —CONH$_2$, H$_2$NCO(C$_1$–C$_6$)alkyl, —CONHR$^8$, R$^8$NHCO (C$_1$–C$_6$)alkyl, —CON(R$^8$)$_2$, (R$^8$)$_2$NCO(C$_1$–C$_6$)alkyl, —CONH(C$_1$–C$_6$)alkylCO$_2$R$^8$, R$^8$O$_2$C(C$_1$–C$_6$)alkylNHCO (C$_1$–C$_6$)alkyl, —CONR$^8$(C$_1$–C$_6$)alkylCO$_2$R$^8$ or R$^8$O$_2$C (C$_1$–C$_6$)alkylNR$^8$CO(C$_1$–C$_6$)alkyl, and said aryl being substituted by —CONH$_2$, H$_2$NCO(C$_1$–C$_6$)alkyl, —CONHR$^8$, R$^8$NHCO(C$_1$–C$_6$)alkyl, —CON(R$^8$)$_2$, (R$^8$)$_2$NCO(C$_1$–C$_6$) alkyl, —CONH(C$_1$–C$_6$)alkylCO$_2$R$^8$, R$^8$O$_2$C(C$_1$–C$_6$) alkylNHCO(C$_1$–C$_6$)alkyl, —CONR$^8$(C$_1$–C$_6$)alkylCO$_2$R$^8$ or R$^8$O$_2$C(C$_1$–C$_6$)alkylNR$^8$CO(C$_1$–C$_6$)alkyl, and the dashed line, X, R, $R^1$, $R^2$, $R^3$, $R^4$ and $R^8$ are as previously defined for a compound of the formula (I), can be prepared by reaction of a compound of the formula (VIII), or an activated derivative thereof, wherein the dashed line, X, R, $R^1$, $R^2$, $R^3$, $R^4$, $R^{10}$ and the term "activated derivative" are as defined in method (6) for a compound of the formula (VIII), with ammonia or with a compound of the formula R$^8$NH$_2$, (R$^8$)$_2$NH, R$^8$O$_2$C(C$_1$–C$_6$ alkyl)NH$_2$ or R$^8$O$_2$C(C$_1$–C$_6$ alkyl) NHR$^8$, wherein R$^8$ is as defined for this method.

The reaction can be carried out by reacting a carboxylic acid of the formula (VIII) with an above amine in the presence of a suitable condensing agent, e.g. 1-(3-dimethylaminopropyl)-3-ethylcarbodiimide.

The reaction can also be carried out by first reacting a carboxylic acid of the formula (VIII) with 1-hydroxybenzotriazole in the presence of a suitable condensing agent, e.g. 1-(3-dimethylaminopropyl)-3-ethylcarbodiimide, to form an activated ester, which can then be reacted with an above amine to provide the required amide.

The reaction can further be carried out by first generating the corresponding acid chloride of a carboxylic acid of the formula (VIII), followed by reacting this acid chloride with an above amine to provide the required amide.

The reaction can further be carried out under the conditions of the Mitsunobu reaction (see Method (6)).

12) The compounds of the formula (I) wherein the dashed line, X, R, $R^1$, $R^2$, $R^3$, $R^4$, $R^5$ and $R^8$ are as defined for method (11), can be prepared by reaction of certain compounds of the formula (I) wherein the dashed line, X, R, $R^1$, $R^2$, $R^3$ and $R^4$ are as defined for this method and $R^5$ is aryl, $C_1$–$C_{12}$ alkyl, $C_2$–$C_{12}$ alkenyl or $C_2$–$C_{12}$ alkynyl, said alkyl, alkenyl and alkynyl being substituted by —CO$_2$R$^9$ or by aryl substituted by —CO$_2$R$^9$ or R$^9$O$_2$C(C$_1$–C$_6$)alkyl, and said aryl being substituted by —CO$_2$R$^9$ or R$^9$O$_2$C(C$_1$–C$_6$)alkyl, wherein R$^9$ is a suitable ester-forming group selected from within the definition of R$^9$ as previously defined for a compound of the formula (I), with ammonia or with a compound of the formula R$^8$NH$_2$, (R$^8$)$_2$NH, R$^8$O$_2$C(C$_1$–C$_6$ alkyl)NH$_2$ or R$^8$O$_2$C(C$_1$–C$_6$ alkyl)NHR$^8$, wherein R$^8$ is as defined for this method.

Examples of suitable ester-forming groups for R$^9$ for this method are $C_1$–$C_4$ alkyl, e.g. methyl and ethyl, phenyl, pentafluorophenyl and p-nitrophenyl.

13) The compounds of the formula (I) wherein $R^5$ is $C_1$–$C_{12}$ alkyl substituted by hydroxy, hydroxyphenyl or hydroxy(C$_1$–C$_6$)alkylphenyl, and the dashed line, X, R, $R^1$, $R^2$, $R^3$ and $R^4$ are as previously defined for a compound of the formula (I), can be prepared by hydrogenation of a compound of the formula (I) wherein $R^5$ is $C_1$–$C_{12}$ alkyl substituted by benzyloxy, benzyloxyphenyl or benzyloxy (C$_1$–C$_6$)alkylphenyl, and the dashed line, X, R, $R^1$, $R^2$, $R^3$ and $R^4$ are as defined for this method.

In a typical procedure the reaction is carried out in the presence of a palladium-on-carbon catalyst and in a suitable solvent, e.g. ethanol, under pressure and at from room temperature to the reflux temperature of the solvent.

14) The compounds of the formula (I) wherein $R^5$ is $C_1$–$C_{12}$ alkyl substituted by amino, and the dashed line, X, R, $R^1$, $R^2$, $R^3$ and $R^4$ are as previously defined for a compound of the formula (I), can be prepared by reaction of a compound of the formula (I) wherein $R^5$ is $C_1$–$C_{12}$ alkyl substituted by phthalimido, and the dashed line, X, R, $R^1$, $R^2$, $R^3$ and $R^4$ are as defined for this method, with a $C_1$–$C_4$ alkylamine (e.g. methylamine) or hydrazine.

The reaction is typically carried out in a suitable solvent, e.g. ethanol, at from room temperature to the reflux temperature of the solvent.

15) The compounds of the formula (I) wherein $R^4$ is 2-methyl-3-oxopyridazin-6-yl and the dashed line, X, R, $R^1$, $R^2$, $R^3$ and $R^5$ are as previously defined for a compound of the formula (I), can be prepared by methylation of a compound of the formula (I) wherein $R^4$ is 3-hydroxypyridazin-6-yl and the dashed line, X, R, $R^1$, $R^2$, $R^3$ and $R^5$ are as defined for this method.

The reaction is typically carried out using a suitable methylating agent, e.g. dimethyl sulphate, in the presence of a suitable base, e.g. potassium carbonate, and in a suitable solvent, e.g. acetone, at from room temperature to, and preferably at, the reflux temperature of the solvent.

16) The compounds of the formula (I) wherein the dashed line does not represent a covalent bond, X is NH, $R^4$ is a group of the formula:

and R, $R^1$, $R^2$, $R^3$, $R^5$, $R^7$ and $R^8$ are as previously defined for a compound of the formula (I), can be prepared by reaction of a compound of the formula:

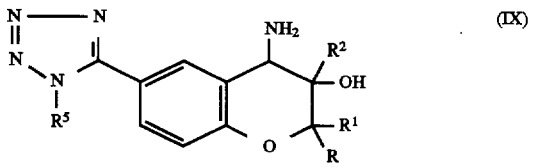

(IX)

wherein R, $R^1$, $R^2$ and $R^5$ are as previously defined for this method, with a compound of the formula $(R^8S)_2C=NR^7$ wherein $R^7$ and $R^8$ are as previously defined for this method.

In a typical procedure the compounds are heated together in pyridine or ethanol.

The intermediates of the formula (IX) can be prepared by reaction of a compound of the formula (II) wherein R, $R^1$, $R^3$ and $R^5$ are as previously defined for this method with ammonia and in a suitable solvent, e.g. ethanol, at from room temperature to the reflux temperature of the solvent, and preferably at from 50° to 70° C.

17) The compounds of the formula (I) wherein the dashed line does not represent a covalent bond, X is NH, $R^4$ is a group of the formula:

wherein $R^6$ is $-OR^8$, $-NHR^8$, $-NH(aryl)$ or $-NH$ (pyridinyl), and R, $R^1$, $R^2$, $R^3$, $R^5$, $R^7$, $R^8$ and "aryl" are as previously defined for a compound of the formula (I), can be prepared by reaction of a compound of the formula (I) wherein the dashed line, X, R, $R^1$, $R^2$, $R^3$, $R^4$, $R^5$, $R^7$ and $R^8$ are as defined for method (16), with a suitable base salt of a compound of the formula $R^8OH$ (i.e. an alkoxide derivative), or with a compound of the formula $R^8NH_2$, $(aryl)NH_2$ or $(pyridinyl)NH_2$, wherein "aryl" and $R^8$ are as defined for this method.

Suitable base salts are the alkali metal salts, e.g. the sodium and potassium salts.

18) The compounds of the formula (I) wherein the dashed line does not represent a covalent bond, X is NH, $R^4$ is a C-linked 4- to 7-membered heterocyclic ring containing from 1 to 3 nitrogen hetero-atoms which is optionally substituted as previously defined in definition (c) for $R^4$ for a compound of the formula (I), and R, $R^1$, $R^2$, $R^3$ and $R^5$ are as previously defined for a compound of the formula (I), can be prepared by reaction of a compound of the formula (IX) wherein R, $R^1$, $R^2$ and $R^5$ are as previously defined for this method, with a 4- to 7-membered ring heterocyclic compound containing from 1 to 3 nitrogen hetero-atoms which is substituted on a ring carbon atom by a leaving group, e.g. halo (preferably chloro or bromo) or a group of the formula $C_1$–$C_4$ alkyl $S(O)_p$— where p is 0, 1 or 2, and optionally further substituted as previously defined for $R^4$ for this method.

In a typical procedure the reaction is carried out in the presence of a suitable acid acceptor, e.g. potassium carbonate or diisopropylethylamine, and in a suitable solvent, e.g. N,N-dimethylacetamide or dioxan, at from room temperature to, and preferably at or about, the reflux temperature thereof.

All of the above reactions and the preparations of novel starting materials used in the preceding methods are conventional and appropriate reagents and reaction conditions for their performance or preparation as well as procedures for isolating the desired products are well known to those skilled in the art with reference to literature precedents and the Examples and Preparations hereto.

A pharmaceutically acceptable salt of a compound of the formula (I) may be readily prepared by mixing together solutions of a compound of the formula (I) and the desired acid or base, as appropriate. The salt may precipitate from solution and be collected by filtration or is recovered by evaporation of the solvent.

The compounds of the formula (I) have smooth muscle relaxant activity since they are able to open potassium channels in such tissue. They can be tested for smooth muscle relaxant activity by a method involving measuring the in vitro relaxation of guinea pig tracheal ring preparations as follows:

Male guinea pigs (500–600 g) were killed by a blow to the head and exsanguinated. The trachea was removed, placed in Krebs solution and cleaned. The trachea was slit through the cartilage along it's longitudinal axis and strips consisting of four adjacent cartilage rings were prepared. The strips were each placed in a water-jacketed organ bath (37° C.) containing Krebs solution and tied to a force-displacement transducer for the measurement of isometric tension responses. The tissues were equilibrated for 60 minutes under a resting load of 1 g and washed every 15 minutes before the start of each experiment.

The composition of the Krebs solution was as follows (millimoles):- NaCl (119); KCl (4.7); $NaHCO_3$ (25); $KH_2PO_4$ (1.2); $MgSO_4$ (1.2); $CaCl_2$ (2.5); glucose (11), and indomethacin (2.8 µM) was added to remove the influence of the endogenous prostanoids. The solution was gassed with 95% $O_2$/5% $CO_2$ and the temperature was kept constant at 37° C.

After the equilibration period a priming dose of KCl (20 mM) was added to each tissue bath and after a further 20 minutes the tissue was washed. After a further 30 minutes KCl (20 mM) was added to contract each tissue. The relaxant action of a compound of the formula (I) was examined when the maintained contractile response had stabilized. The compounds can be added cumulatively ($10^{-8}$–$10^{-5}$ mol) at 5 minute intervals.

The reversal to pretreatment base line was taken as 100 percent relaxation in these studies and concentration-relaxation curves were constructed in order to obtain $IC_{50}$ values for potency.

For human use, the compounds of the formula (I) and their salts can be administered alone, but will generally be administered in admixture with a pharmaceutical carrier selected with regard to the intended route of administration and standard pharmaceutical practice.

For example, they can be administered orally in the form of tablets containing such excipients as starch or lactose, or in capsules or ovules either alone or in admixture with excipients, or in the form of elixirs, solutions or suspensions containing flavouring or colouring agents.

They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the compounds of the formula (I) will be from 0.01 to 20 mg/kg (in single or divided doses) and preferably will be from 0.1 to 5 mg/kg.

Thus tablets or capsules of the compounds will contain from 1 mg to 0.5 g of active compound for administration singly or two or more at a time, as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

The compounds of formula (I) can also be administered by inhalation and are conveniently delivered in the form of an aerosol spray presentation from a pressurised container or a nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of formula (I) and a suitable powder base such as lactose or starch.

Aerosol formulations are preferably arranged so that each metered dose or "puff" of aerosol contains from 20 µg to 1000 µg of a compound of formula (I), or a pharmaceutically acceptable salt thereof, for delivery to the patient. The overall daily dose with an aerosol will be within the range of from 20 µg to 10 mg which may be administered in a single dose or, more usually, in divided doses throughout the day.

Alternatively, the compounds of the formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration of from 1 to 10%, into an ointment consisting of a white wax or white soft paraffin base together with such stabilizers and preservatives as may be required.

Thus the invention further provides:

i) a pharmaceutical composition comprising a compound of the formula (I), or a pharmaceutically acceptable salt thereof, together with a pharmaceutically acceptable diluent or carrier;

ii) a compound of the formula (I), or a pharmaceutically acceptable salt or composition thereof, for use as a medicament;

iii) the use of a compound of the formula (I), or of a pharmaceutically acceptable salt or composition thereof, for the manufacture of a medicament for the curative or prophylactic treatment of angina or a disease associated with the altered tone and/or motility of smooth muscle;

iv) use as stated in (iii) where the disease is chronic obstructive airways disease, asthma, urinary incontinence, irritable bowel syndrome, diverticular disease, oesophageal achalasia or hypertension;

v) a method of treatment of a human to cure or prevent angina or a disease associated with the altered tone and/or motility of smooth muscle which comprises treating said human with an effective amount of a compound of the formula (I) or with a pharmaceutically acceptable salt or composition thereof;

vi) a method as stated in (v) where the disease is chronic obstructive airways disease, asthma, urinary incontinence, irritable bowel syndrome, diverticular disease, oesophageal achalasia or hypertension; and vii) intermediates of the formulae (II), (V), (VI) or a base salt thereof, (VIII) or an activated derivative thereof, and (IX).

The following Examples illustrate the preparation of the compounds of the formula (I):

EXAMPLE 1

(3S,4R)-3,4-Dihydro-6-(1-[3-ethoxycarbonylprop-1-yl]-1H-tetrazol-5-yl)-3-hydroxy-4-(3-hydroxypyridazin-6-yl)oxy-2,2,3-trimethyl-2H-benzo[b]pyran

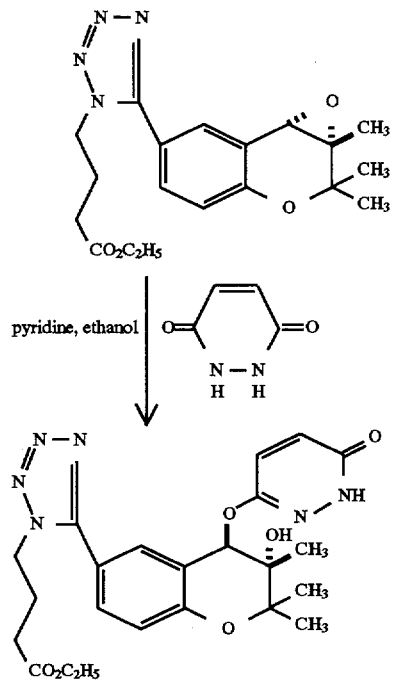

A mixture containing (3S,4S)-3,4-dihydro-3,4-epoxy-6-(1-[3-ethoxycarbonylprop-1-yl]-1H-tetrazol-5-yl)-2,2,3-trimethyl-2H-benzo[b]pyran (see Preparation 1) (0.5 g), 3,6-dihydroxypyridazine (0.23 g), pyridine (0.1 g) and ethanol (10 ml) was heated under reflux for 6 days. On cooling to room temperature the mixture was concentrated in vacuo and the residue azeotroped with dichloromethane (6×10 ml). The resulting foam was purified by chromatography on silica eluting with dichloromethane containing methanol (2.5% up to 5%). The product-containing fractions were combined and concentrated in vacuo to give an oil which was azeotroped with hexane to give the title compound as a colourless solid, 0.32 g, m.p. 90°–110° C.

$^1$H-NMR (CDCl$_3$): δ=7.75(s,1H), 7.60–7.50(dd,1H), 7.15–7.10(d,1H), 7.05–6.95(m,3H), 6.00(s,1H), 4.50–4.40(t,2H), 4.15–4.00(q,2H), 3.55(s,1H), 2.50–2.35(m,2H), 2.30–2.20(m,2H), 1.50(s,3H), 1.45(s,3H), 1.30(s,3H), 1.30–1.20(t,3H) ppm.

EXAMPLES 2 TO 13

The compounds of the following tabulated Examples of the general formula:

5,677,324

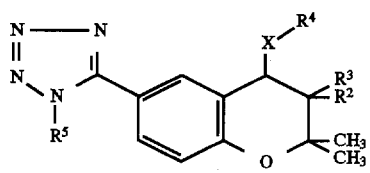

were prepared using similar methods to that used in Example 1 using the appropriate starting materials.

| Ex. | Stereo-chem. | X | R³ | R² | R⁴ | R⁵ | Oxirane starting material ref. | m.p. (°C.) | Analysis/¹H-NMR (CDCl₃)¹ |
|---|---|---|---|---|---|---|---|---|---|
| 2² | 3S, 4R | O | OH | CH₃ | ![HN-pyridone] | —(CH₂)₃CO₂C₂H₅ | see Prep. 1 | 100–107 | Found: C, 57.39; H, 5.98; N, 13.77; C₂₄H₂₉N₅O₆.0.25 CH₂Cl₂ requires: C, 57.71; H, 5.89; N, 13.88%. δ = 7.60–7.50(m, 2H), 7.25–7.20(d, 1H), 7.05–6.95(d, 1H), 6.35(s, 1H), 6.15–6.10(dd, 1H), 5.55(s, 1H), 4.50–4.40(t, 2H), 4.10–4.00(q, 2H), 3.80–3.60(brs, 1H), 2.45–2.35(m, 2H), 2.30–2.10(m, 2H), 1.55(s, 3H), 1.50(s, 3H), 1.35(s, 3H), 1.25–1.20(t, 3H) ppm. |
| 3³ | 3S, 4R | O | OH | CH₃ | ![pyridazinone] | CH₃ | see Prep. 9 | 249–251 | Found: C, 55.84; H, 5.28; N, 21.67; C₁₈H₂₀N₆O₄ requires: C, 56.24; H, 5.24; N, 21.86%. δ = 7.70–7.60(m, 2H), 7.25–7.20(d, 1H), 7.00–6.90(m, 2H), 5.90(s, 1H), 5.35(s, 1H), 4.05(s, 3H), 1.40(s, 3H), 1.35(s, 3H), 1.20(s, 3H) ppm. |
| 4⁴ | 3S, 4R | O | OH | CH₃ | ![pyridazinone] | —CH₂CO₂C₂H₅ | see Prep 12 | 102–120°C. (with foaming) | Found: C, 53.55; H, 5.22; N, 17.42; C₂₁H₂₄N₆O₆.0.2CH₂Cl₂ requires: C, 53.77, H, 5.19; N, 17.75%. δ = 7.65(s, 1H), 7.55–7.45(dd, 1H), 7.15–7.10(d, 1H), 7.05–6.90(m, 2H), 6.00(s, 1H), 5.15(s, 2H), 4.25–4.15(q, 2H), 3.65(s, 1H), 1.50(s, 3H), 1.45(s, 3H), 1.30(s, 3H), 1.15–1.10(t, 3H) ppm. |
| 5⁵ | 3S, 4R/ 3R, 4S | O | OH | CH₃ | ![pyridazinone] | —(CH₂)₂-C₆H₄-O-CH₂-C₆H₅ | see Prep. 15 | 213–218 | Found: C, 66.22; H, 5.73; N, 14.16; C₃₂H₃₂N₆O₅ requires: C, 66.19; H, 5.56; N, 14.47%. (d₆-DMSO) δ = 7.45(s, 1H), 7.40–7.25(m, 6H), 7.25–7.15(d, 1H), 6.90–6.70(m, 6H), 5.90(s, 1H), 5.35(s, 1H), 5.00(s, 2H), 4.60–4.50(t, 2H), 3.05(t, 2H), 1.40(s, 3H), 1.30(s, 3H), 1.20(s, 3H) ppm. |

-continued

| Ex. | Stereo-chem. | X | R³ | R² | R⁴ | R⁵ | Oxirane starting material ref. | m.p. (°C.) | Analysis/¹H-NMR (CDCl₃)¹ |
|---|---|---|---|---|---|---|---|---|---|
| 6[6] | 3S, 4R | O | OH | CH₃ | (pyridazinone ring with NH-N, C=O, CH₃) | —CH₂—phenyl | see Prep. 18 | — | (d₆-DMSO) δ = 7.55–7.50(dd, 1H), 7.50(s, 1H), 7.30–7.20(m, 3H), 7.20–7.15(d, 1H), 7.05–6.95(m, 2H), 6.95–6.85(m, 2H), 5.90(s, 1H), 5.65(s, 2H), 5.35(s, 1H), 1.35(s, 3H), 1.30(s, 3H), 1.15(s, 3H) ppm. |
| 7[7] | 3S, 4R | O | OH | CH₃ | (pyridazinone ring with NH-N, C=O, CH₃) | —(CH₂)₂—phenyl | see Prep. 21 | — | Found: C, 58.49; H, 5.19; N, 15.93; C₂₅H₂₆N₆O₄·0.6 CH₂Cl₂ requires: C, 58.52; H, 5.22; N, 16.00%. (d₆-DMSO) δ = 7.35–7.30(m, 2H), 7.25–7.20(dd, 1H), 7.15–7.05(m, 3H), 6.95–6.80(m, 4H), 5.90(s, 1H), 5.70(d, 1H), 5.35(s, 1H), 4.65(m, 2H), 3.10–3.00 (m, 2H), 1.40(s, 3H), 1.35(s, 3H), 1.20(s, 3H) ppm. |
| 8[8] | 3S, 4R/ 3R, 4S | direct link | OH | H | (pyridinone ring) | —(CH₂)₂—C₆H₄—OCH₃ | see Prep. 24 | — | δ = 7.40–7.35(m, 1H), 7.20–7.10(dd, 1H), 6.95–6.85(m, 2H), 6.80–6.65(m, 5H), 6.35–6.25(d, 1H), 6.25–6.15(t, 1H), 4.50–4.40(m, 2H), 4.25(d, 1H), 3.90–3.85(m, 1H), 3.75(s, 3H), 3.20–3.00(m, 2H), 1.55(s, 3H), 1.40(s, 3H) ppm. |
| 9[8] | 3S, 4R/ 3R, 4S | direct link | OH | O | (pyridinone ring) | —(CH₂)₃CO₂C₂H₅ | see Prep. 36 | 145–147 | Found: C, 60.56; H, 5.92; N, 15.33; C₂₃H₂₇N₅O₅ requires: C, 60.92; H, 6.00; N, 15.44%. δ = 7.65–7.60(d, 1H), 7.40–7.35(m, 1H), 7.20(s, 1H), 7.10–7.05(d, 1H), 7.05–6.95(dd, 1H), 6.70–6.65(d, 1H), 6.45–6.35(d, 1H), 6.30–6.20(t, 1H), 4.50–4.30(m, 2H), 4.30(d, 1H), 4.15–4.05(q, 2H), 3.95–3.90(m, 1H), 2.40–2.30(m, 2H), 2.20–2.10(m, 2H), 1.55(s, 3H), 1.40(s, 3H), 1.30–1.20(t, 3H) ppm. |
| 10[8] | 3S, 4R/ 3R, 4S | direct link | OH | H | (pyridinone ring) | —CH(CO₂C₂H₅)— | see Prep. 72 | — | δ = 7.55–7.50(dd, 1H), 7.45–7.35(m, 1H), 7.10(s, 1H), 7.10–7.05(d, 1H), 7.00–6.95(dd, 1H), 6.70–6.65(d, 1H), 6.40–6.35(d, 1H), 6.30–6.20(t, 1H), 5.05(s, 2H), 4.30–4.10(q, 2H), 4.15–4.10(m, 1H), 3.95–3.85(m, 1H), 1.55(s, 3H), 1.40(s, 3H), 1.30–1.20(t, 3H) ppm. |

-continued

| Ex. | Stereo-chem. | X | $R^3$ | $R^2$ | $R^4$ | $R^5$ | Oxirane starting material ref. | m.p. (°C.) | Analysis/$^1$H-NMR (CDCl$_3$)[1] |
|---|---|---|---|---|---|---|---|---|---|
| 11[9] | 3S, 4R | O | OH | CH$_3$ | (structure: pyridazinone with NH-N, (CH$_2$)$_4$-CO$_2$C$_2$H$_5$ substituent) | | see Prep. 65 | — | Found: C, 57.44; H, 6.10; N, 16.40; C$_{24}$H$_{30}$N$_6$O$_6$ requires: C, 57.82; H, 6.07; N, 16.86%. δ = 7.65(d, 1H), 7.50–7.40(dd, 1H), 7.10–7.05(d, 1H), 7.00–6.90(m, 3H), 6.00(s, 1H), 4.40–4.25(t, 2H), 4.10–4.00(q, 2H), 3.00–2.40(brs, 1H), 2.30–2.20(t, 2H), 2.00–1.85(m, 2H), 1.65–1.50(m, 2H), 1.50(s, 3H), 1.45(s, 3H), 1.25(s, 3H), 1.20–1.15(t, 3H) ppm. |
| 12[10] | 3S, 4R | O | OH | CH$_3$ | (structure: pyridazinone H-N) | —(CH$_2$)$_4$CO$_2$C$_2$H$_5$ | see Prep. 65 | — | δ = 7.55–7.45(m, 2H), 7.25–7.20(d, 1H), 7.05–6.95(d, 1H), 6.35(s, 1H), 6.10–6.05(m, 1H), 5.55(s, 1H), 4.50–4.00(brs, 1H), 4.40–4.30(t, 2H), 4.10–4.05(q, 2H), 2.30–2.20(t, 2H), 2.15–2.00(m, 1H), 2.00–1.85(m, 2H), 1.65–1.50(m, 2H), 1.50(s, 3H), 1.45(s, 3H), 1.35(s, 3H), 1.25–1.20(t, 3H) ppm. |
| 13[11] | 3S, 4R | O | OH | CH$_3$ | (structure: pyridazinone N—CH$_3$) | —(CH$_2$)$_3$CO$_2$C$_2$H$_5$ | see Prep. 1 | — | Found: C, 57.86; H, 6.47; N, 16.66; C$_{24}$H$_{30}$N$_6$O$_6$ requires: C, 57.82; H, 6.07; N, 16.86%. δ = 7.75(d, 1H), 7.60–7.50(dd, 1H), 7.10–6.95(m, 3H), 5.95(s, 1H), 4.50–4.40(t, 2H), 4.15–4.05(q, 2H), 3.75(s, 1H), 3.70(s, 3H), 2.45–2.35(m, 2H), 2.30–2.20(m, 2H), 1.50(s, 3H), 1.45(s, 3H), 1.30(s, 3H), 1.30–1.20(t, 3H) ppm. |

[1] Except where stated.
[2] Eluant for column chromatography was dichloromethane containing methanol (2.5% up to 12%) + 1% concentrated aqueous ammonia.
[3] Eluant for column chromatography was dichloromethane containing methanol (5% up to 10%) + concentrated aqueous ammonia (0.25% up to 0.5%). The product obtained by chromatography was triturated with diethyl ether.
[4] The product obtained by chromatography was triturated with hexane.
[5] Eluant for column chromatography was dichloromethane containing methanol (0% up to 5%). The product obtained by chromatography was triturated with diethyl ether.
[6] Eluant for column chromatography was dichloromethane containing methanol (5%). The product obtained by chromatography was triturated with diethyl ether.
[7] Eluant for column chromatography was dichloromethane containing methanol (5%). The product obtained by chromatography was triturated with hexane.
[8] Eluant for column chromatography was ethyl acetate.
[9] Eluant for column chromatography was ethyl acetate. The product obtained by chromatography was triturated with diethyl ether.
[10] Eluant for column chromatography was dichloromethane containing methanol (2%) + concentrated aqueous ammonia (0.3%).
[11] For the preparation of the 1-methylpyridazin-3,6-dione starting material see J. Org. Chem., 36, 3372 (1971). Eluant for column chromatography was ethyl acetate. The product obtained by chromatography was crystallised from methanol/diethyl ether.

EXAMPLE 14

(3S,4R/3R,4S)-3,4-Dihydro-2,2-dimethyl-3-hydroxy-4-(2-oxo-1,2-dihydropyridin-1-yl)-6-(1-[3-phenylprop-1-yl]-1H-tetrazol-5-yl)-2H-benzo[b]pyran

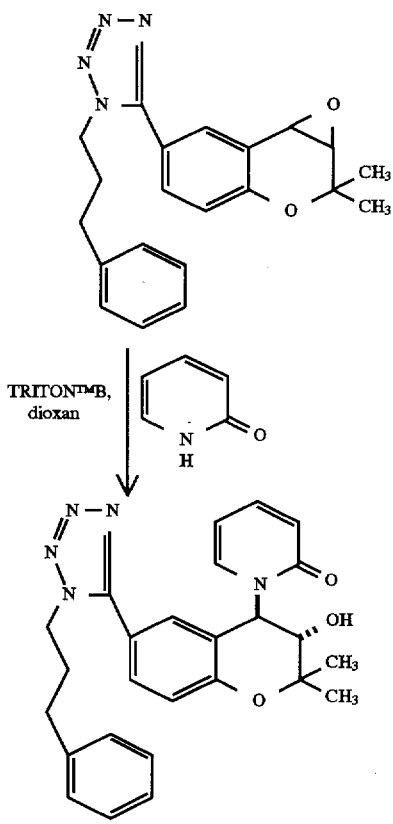

(only one stereoisomer shown)

A mixture containing (3S,4S/3R,4R)-3,4-dihydro-2,2-dimethyl-3,4-epoxy-6-(1-[3-phenylprop-1-yl]-1H-tetrazol-5-yl)-2H-benzo[b]pyran (see Preparation 28) (2.6 g), 2-hydroxypyridine (2 g), benzyltrimethylammonium hydroxide (TRITON™B) (0.5 ml of a 40% solution in methanol) and dioxan (20 ml) was heated under reflux for 7 hours then concentrated in vacuo. The residue was purified by chromatography on silica eluting with 1:1 ethyl acetate/dichloromethane. The product-containing fractions were combined and concentrated in vacuo to give the title compound as a foam, 1.8 g. Found: C,66.97; H,5.73; N,14.78; $C_{26}H_{27}N_5O_3 \cdot 0.1$ $CH_2Cl_2$ requires: C,67.27; H,5.88; N,15.03%.

$^1$H-NMR (CDCl$_3$): δ=7.50–7.45(d,1H), 7.35–7.20(m, 4H), 7.10–7.00(m,3H), 6.90–6.85(d,1H), 6.85–6.80(d,1H), 6.40–6.35(d,1H), 6.20–6.10(t, 1H), 4.30–4.25(t,2H), 4.25–4.20(m,1H), 3.90–3.85(m,1H), 2.65–2.55(t,2H), 2.30–2.15(m,2H), 1.55(s,3H), 1.40(s,3H) ppm.

EXAMPLES 15 TO 21

The compounds of the following tabulated Examples of the general formula:

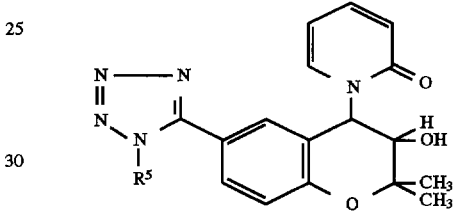

were prepared using similar methods to that used in Example 14 using the appropriate starting materials.

| Ex. | Stereo-chem. | R$^5$ | Oxirane starting material ref. | m.p. (°C.) | Analysis/$^1$H-NMR(CDCl$_3$) |
|---|---|---|---|---|---|
| 15 | 3S, 4R/ 3R, 4S | —(CH$_2$)$_4$—Ph | see Prep. 33 | 98–103 | Found: C, 68.55; H, 6.45; N, 14.50; C$_{27}$H$_{29}$N$_5$O$_3$ requires: C, 68.77; H, 6.20; N, 14.85%. δ = 7.55–7.50(d, 1H), 7.35–7.10(m, 4H), 7.15–7.05(m, 4H), 6.95–6.90(d, 1H), 6.70–6.65(d, 1H), 6.45–6.35(d, 1H), 6.20–6.15(t, 1H), 4.35–4.25(t, 2H), 4.10(d, 1H), 3.90–3.85(m, 1H) 265–2.55(t, 2H), 1.95–1.80(m, 2H), 1.65–1.50(m, 5H), 1.40(s, 3H) ppm. |
| 16[1] | 3S, 4R/ 3R, 4S | —(CH$_2$)$_2$—O—CH$_2$—Ph | see Prep. 39 | — | δ = 7.75–7.70(dd, 1H), 7.40–7.20(m, 5H), 7.10–7.05(m, 2H), 6.95–6.90(d, 1H), 6.70–6.60(d, 1H), 6.40(d, 1H), 6.20–6.15(t, 1H), 4.50–4.45(m, 2H), 4.40–4.25(ABq, 2H), 4.30–4.20(m, 1H), 3.95–3.85(m, 3H), 1.55(s, 3H), 1.40(s, 3H) ppm. |

-continued

| Ex. | Stereo-chem. | R⁵ | Oxirane starting material ref. | m.p. (°C.) | Analysis/¹H-NMR(CDCl₃) |
|---|---|---|---|---|---|
| 17[2] | 3S, 4R/ 3R, 4S | —(CH₂)₂—N(phthalimide) | see Prep. 43 | 221–223 | Found: C, 58.51; H, 4.40; N, 14.71; $C_{27}H_{24}N_6O_5 \cdot 0.67CH_2Cl_2$ requires: C, 58.44; H, 4.48; N, 14.78%. δ = 7.85–7.70(m, 4H), 7.50–7.45(d, 1H), 7.40–7.35(m, 1H), 7.10(s, 1H), 7.05–6.95(d, 1H), 6.95–6.90(d, 1H), 6.70–6.65(d, 1H), 6.35–6.25(m, 2H), 4.70–4.60(m, 2H), 4.25(d, 1H), 4.10–4.00(m, 2H), 3.90–3.85(m, 1H), 1.55(s, 3H), 1.35(s, 3H) ppm. |
| 18[3] | 3S, 4R/ 3R, 4S | —(CH₂)₂—(3-OCH₃-phenyl) | see Prep. 49 | — | Found C, 65.07; H, 5.98; N, 13.59; $C_{26}H_{27}N_5O_4 \cdot 0.4CH_3CO_2C_2H_5$ requires: C, 65.16; H, 5.98; N, 13.77%. δ = 7.40–7.30(m, 1H), 7.20–7.10(m, 2H), 7.05–6.90(m, 2H), 6.80–6.75(m, 3H), 6.50–6.45(d, 1H), 6.35–6.25((m, 2H), 6.25–6.20(m, 1H), 4.60–4.40(m, 2H), 4.25(d, 1H), 3.95–3.85(m, 1H), 3.75(s, 3H), 3.25–3.05(m, 2H), 1.55(s, 3H), 1.40(s, 3H) ppm. |
| 19[3] | 3S, 4R/ 3R, 4S | —(CH₂)₂—(2-OCH₃-phenyl) | see Prep. 52 | — | δ = 7.40–7.15(m, 3H), 7.00–6.95(d, 1H), 6.90(d, 1H), 6.80–6.65(m, 5H), 6.30(d, 1H), 6.20–6.15(t, 1H), 4.65–4.45(m, 2H), 4.30(d, 1H), 3.90–3.85(m, 1H), 3.65(s, 3H), 3.25–3.05(m, 2H), 1.55(s, 3H), 1.40(s, 3H) ppm. |
| 20[4] | 3S, 4R/ 3R, 4S | —(CH₂)₂OCH₃ | see Prep. 56 | 224–225 | Found: C, 60.60; H, 5.87; N, 17.51; $C_{20}H_{23}N_5O_4$ requires: C, 60.44; H, 5.83; N, 17.62%. δ = 7.75–7.70(dd, 1H), 7.45–7.30(m, 2H), 7.10–7.05(d, 1H), 7.00(dd, 1H), 6.70(d, 1H), 6.45–6.35(d, 1H), 6.30–6.20(t, 1H), 4.45–4.35(m, 2H), 4.15–4.05(m, 1H), 3.95–3.75(m, 3H), 3.15(s, 3H), 1.55(s, 3H), 1.40(s, 3H) ppm. |
| 21[5] | 3S, 4R/ 3R, 4S | —(CH₂)₂—phenyl | see Prep. 62 | 180–190 | Found: C, 67.81; H, 5.68; N, 15.80; $C_{25}H_{25}N_5O_3$ requires: C, 67.70; H, 5.68; N, 15.79%. δ = 7.40–7.35(m, 1H), 7.25–7.10(m, 4H), 6.95–6.90(d, 1H), 6.90–6.80(m, 3H), 6.70(d, 1H), 6.65(s, 1H), 6.30–6.25(d, 1H), 6.20–6.15(t, 1H), 4.55–4.40(m, 2H), 4.20(d, 1H), 3.90–3.85(dd, 1H), 3.26–3.10(m, 2H), 1.55(s, 3H), 1.35(s, 3H) ppm. |

[1]Eluant for column chromatography was dichloromethane containing methanol (1%).
[2]Eluant for column chromatography was ethyl acetate and the product obtained was triturated with diethyl ether.
[3]Eluant for column chromatography was ethyl acetate.
[4]Eluant for column chromatography was dichloromethane containing methanol (2.5%) and the product obtained was triturated with diethyl ether.
[5]Column chromatography was unnecessary. The reaction mixture was cooled to room temperature, diluted with dichloromethane and washed with water, then dried (MgSO₄) and concentrated in vacuo. The resulting solid was crystallised from ethyl acetate to give the product.

EXAMPLE 22

(3S,4R/3R,4S)-3,4-Dihydro-2,2-dimethyl-3-hydroxy-4-(2-oxopiperidin-1-yl)-6-(1-[3-phenylprop-1-yl]-1H-tetrazol-5-yl)-2H-benzo[b]pyran

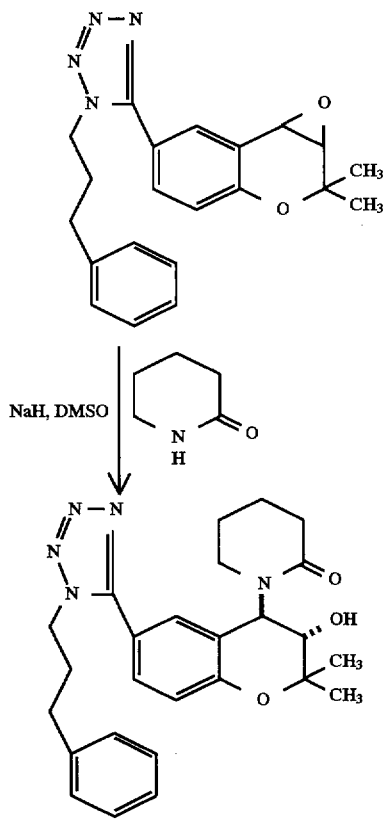

(only one stereoisomer shown)

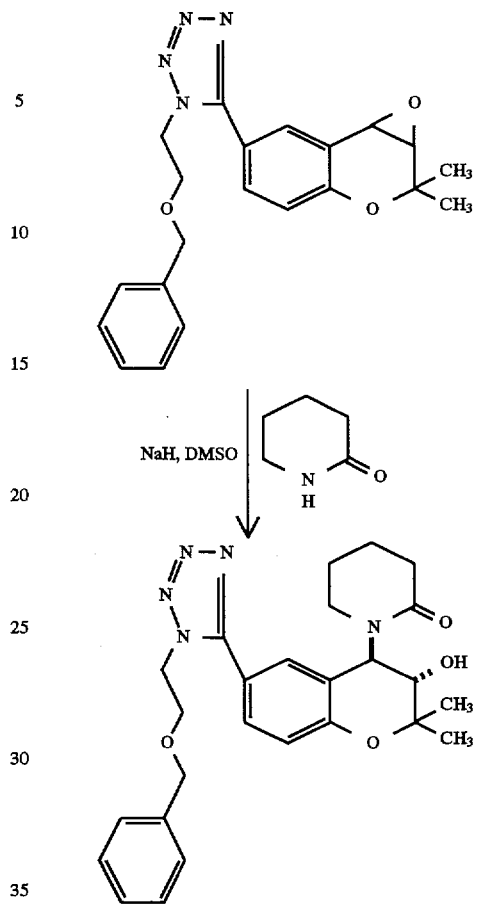

(only one stereoisomer shown)

Sodium hydride (0.4 g of an 80% dispersion in mineral oil) was added to a solution of δ-valerolactam (1.3 g) in dimethyl sulphoxide (DMSO) (10 ml), and the mixture was stirred at room temperature for 1 hour. A solution of (3S,4S/3R,4R)-3,4-dihydro-2,2-dimethyl-3,4-epoxy-6-(1-[3-phenylprop-1-yl]-1H-tetrazol-5-yl)-2H-benzo[b]pyran (see Preparation 28) (1.6 g) in dimethyl sulphoxide (10 ml) was added and the mixture was stirred at room temperature for 16 hours. Water (100 ml) was added and the mixture was extracted with ethyl acetate (3×50 ml). The combined extracts were concentrated in vacuo to give an oil which was purified by chromatography on silica eluting with dichloromethane containing methanol (2%). The product-containing fractions were combined and concentrated in vacuo to give a foam which was triturated with diethyl ether then diluted with hexane to give the title compound as a solid foam, 0.4 g.

$^1$H-NMR (CDCl$_3$): δ=7.40–7.20(m,5H), 7.15–7.10(d, 2H), 7.00–6.95(d,1H), 6.05–5.95(d,1H), 3.85–3.80(m,1H), 3.80–3.65(m,2H), 3.45–3.40(m,1H), 3.15–3.00(m,1H), 3.00–2.85(m,1H), 2.75–2.65(m,2H), 2.65–2.55(m,2H), 2.35–2.20(m,2H), 1.90–1.60(m,4H), 1.55(s,3H), 1.35(s,3H) ppm.

EXAMPLE 23

(3S,4R/3R,4S)-6-(1-[2-Benzyloxyethyl]-1H-tetrazol-5-yl)-3,4-dihydro-2,2-dimethyl-3-hydroxy-4-(2-oxopiperidin-1-yl)-2H-benzo[b]pyran Sodium hydride (0.28 g of an 80% dispersion in mineral oil) was added, over 10 minutes, to a solution of 2-oxopiperidine (1.1 g) and (3S,4S/3R,4R)-6-(1-[2-benzyloxyethyl]-1H-tetrazol-5-yl)-3,4-dihydro-2,2-dimethyl-3,4-epoxy-2H-benzo[b]pyran (see Preparation 39) (3.2 g). When the addition was complete the mixture was stirred at room temperature for 6 hours then poured onto ice (100 g). The mixture was extracted with ethyl acetate (2×50 ml) and the combined extracts were washed with saturated sodium chloride solution (50 ml) then concentrated in vacuo. The residue was purified by chromatography on silica eluting with ethyl acetate. The product-containing fractions were combined and concentrated in vacuo to give the title compound as a foam, 1.3 g. Found: C,64.42; H,6.55; N,14.28; $C_{26}H_{31}N_5O_4 \cdot 0.07$ $CH_2Cl_2$ requires: C,64.79; H,6.49; N,14.49%.

$^1$H-NMR (CDCl$_3$): δ=7.70–7.60(d,1H), 7.45(s,1H), 7.35–7.25(m,3H), 7.15–7.10(m,2H), 6.95–6.90(d,1H), 6.05–5.95(d,1H), 4.55–4.45(m,2H), 4.45(s,2H), 4.05–3.95(m,2H), 3.90–3.75(m,1H), 3.40(d,1H), 3.10–2.90(m,2H), 2.60–2.50(m,2H), 1.90–1.65(m,4H), 1.55(s,3H), 1.30(s,3H) ppm.

EXAMPLE 24

(3S,4R)-3,4-Dihydro-6-(1-[3-ethoxycarbonylprop-1-yl]-1H-tetrazol-5-yl)-3-hydroxy-4-(1-oxocyclopent-2-en-3-yl)oxy-2,2,3-trimethyl-2H-benzo[b]pyran

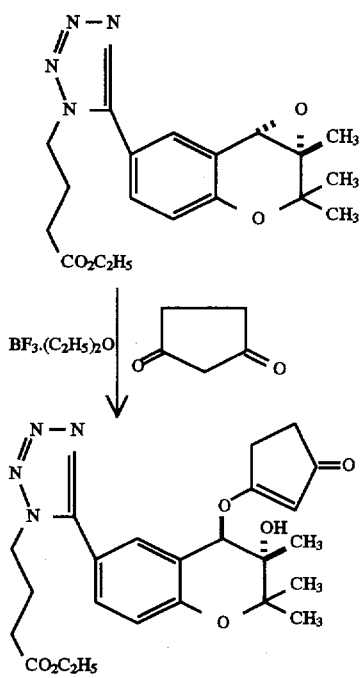

Sodium hydride (0.048 g of an 80% dispersion in mineral oil) was added to a solution of cyclopentan-1,3-dione (0.16 g) in anhydrous tetrahydrofuran (25 ml) and the mixture was stirred at room temperature for 45 minutes. A solution of (3S,4S)-3,4-dihydro-3,4-epoxy-6-(1-[3-ethoxycarbonylprop-1-yl]-1H-tetrazol-5-yl)-2,2,3-trimethyl-2H-benzo[b]pyran (see Preparation 1) (0.5 g) in anhydrous tetrahydrofuran (25 ml) was added followed by boron trifluoride etherate (0.2 ml). The mixture was stirred at room temperature for 2 hours then 10% aqueous sodium bicarbonate (100 ml) was added and the mixture was extracted with ethyl acetate (2×50 ml). The combined extracts were washed with 1N hydrochloric acid (50 ml) and concentrated in vacuo. The residue was purified by chromatography on silica eluting with ethyl acetate containing hexane (50% down to 0%). The product-containing fractions were combined and concentrated in vacuo to give the title compound as a foam, 0.096 g. Found: C,59.14; H,6.33; N,11.78; $C_{24}H_{30}N_4O_6 \cdot H_2O$ requires: C,59.01; H,6.60; N,11.47%.

$^1$H-NMR (CDCl$_3$): δ=7.60–7.50(m,2H), 7.05–7.00(d, 1H), 5.70(s,1H), 5.35(s,1H), 4.50–4.40(m,2H), 4.10–4.00 (m,2H), 2.90(s,1H), 2.85–2.65(m,2H), 2.55–2.30(m,4H), 2.30–2.15(m,2H), 1.50(s,3H), 1.45(s,3H), 1.35(s,3H), 1.30–1.20(t,3H) ppm.

EXAMPLE 25

(3S,4R/3R,4S)-3,4-Dihydro-2,2-dimethyl-3-hydroxy-6-(1-methyl-1H-tetrazol-5-yl)-4-(2-oxo-1,2-dihydropyridin-1-yl)-2H-benzo[b]pyran

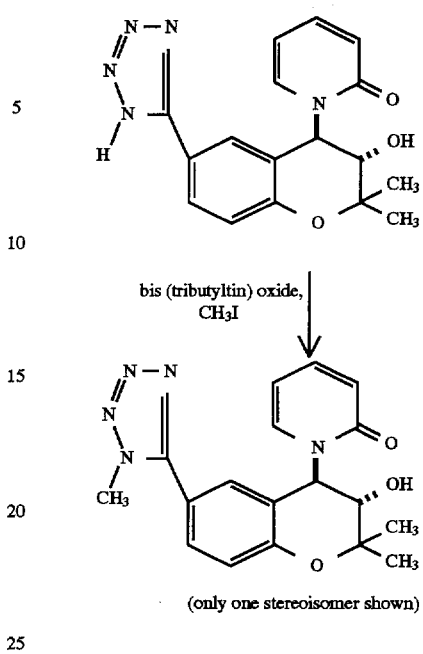

(only one stereoisomer shown)

A mixture containing (3S,4R/3R,4S)-3,4-dihydro-2,2-dimethyl-3-hydroxy-4-(2-oxo-1,2-dihydropyridin-1-yl)-6-(1H-tetrazol-5-yl)-2H-benzo[b]pyran (see Preparation 59) (0.5 g), iodomethane (5 ml) and bistributyltin oxide (0.9 g) was stirred at room temperature for 4 days then partitioned between dichloromethane (50 ml) and 10% aqueous sodium hydroxide (50 ml). The layers were separated and the dichloromethane solution was washed with water (50 ml) then dried (MgSO$_4$) and concentrated in vacuo to give an oil which was triturated with a mixture of hexane (20 ml) and ethyl acetate (10 ml) to give a solid. The solid was purified by chromatography on silica eluting with dichloromethane containing methanol (1% up to 3%) and acetic acid (1% up to 3%).

The fractions containing the higher Rf product were combined and concentrated in vacuo to give (3S,4R/3R,4S)-3,4-dihydro-2,2-dimethyl-3-hydroxy-6-(2-methyl-1H-tetrazol-5-yl)-4-(2-oxo-1,2-dihydropyridin-1-yl)-2H-benzo[b]pyran, 0.07 g.

The fractions containing the lower Rf product were combined and concentrated in vacuo to give a solid which was recrystallised from ethanol to give the title compound, 0.2 g, m.p. 235°–237° C. Found: C,61.36; H,5.21; N,19.62; $C_{18}H_{19}N_6O_3$ requires: C,61.17; N,5.42; N,19.82%.

$^1$H-NMR (d$_6$-DMSO) [mixture of rotamers]: δ=7.85–7.80 (d,0.25H), 7.65–7.60(d,0.5H), 7.60–7.55(d,0.25H), 7.50–7.35(m,2H), 7.15(s,0.25H), 7.10–6.95(m,1.75H), 6.50–6.45(d,0.25H), 6.30–6.15(m,2H), 5.80–5.75(d,1H), 4.95–4.90(d,0.25H), 4.55–4.50(m,0.25H), 4.05–3.95(m, 3H), 1.45(s,2H), 1.40(s,1H), 1.25(s,2H), 1.20(s,1H) ppm.

EXAMPLES 26 TO 36

The compounds of the following tabulated Examples of the general formula:

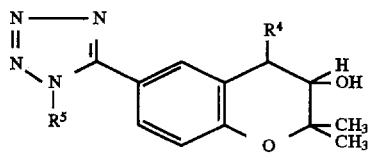

were prepared by similar methods to that used in Example 25 using the appropriate starting materials.

| Ex. | Stereo-chem. | R⁴ | R⁵ | Alkylating agent | Tetrazole starting material ref. | m.p. (°C.) | Analysis/¹H-NMR (CDCl₃)¹ |
|---|---|---|---|---|---|---|---|
| 26[2] | 3S, 4R/ 3R, 4S | (3,4-dihydro-2H-pyridin-2-one-5-yl) | —C₂H₅ | Ethyl iodide | see Prep. 59 | 226 | Found: C, 62, 19; H, 5.79; N, 18.79; C₁₉H₂₁N₅O₃ requires: C, 62.11; H, 5.76; N, 19.06%. (d₆-DMSO) [mixture of rotomers]: δ = 7.85–7.80(d, 0.5H), 7.60–7.30(m, 2.5H), 7.10–6.85(m, 2H), 6.55–6.45(d, 0.5H), 6.30–6.20(m, 2H), 5.85–5.75(d, 1H), 4.95–4.90(m, 0.25H), 4.55–4.45(m, 0.25H), 4.35–4.20(m, 2H), 4.10–3.95(m, 1H), 1.45(s, 2H), 1.40(s, 1H), 1.30–1.10(m, 6H) ppm. |
| 27[3] | 3S, 4R/ 3R, 4S | (piperidin-2-one-5-yl) | —(CH₂)₂CH₃ | n-Propyl iodide | see Prep. 60 and 61 | 184–185 | δ = 7.50–7.45(d, 1H), 7.35(s, 1H), 7.00(d, 1H), 6.05–5.95(d, 1H), 4.40–4.30(t, 2H), 3.90–3.80(d, 1H), 3.15–2.95(m, 3H), 2.65–2.55(m, 2H), 2.00–1.70(m, 5H), 1.55(s, 3H), 1.30(s, 3H), 1.00–0.90(t, 3H) ppm. |
| 28[4] | 3S, 4R/ 3R, 4S | (piperidin-2-one-5-yl) | —(CH₂)₂O—C₆H₅ | 2-Phenoxy-ethyl bromide | see Prep. 60 and 61 | 115–120 | Found: C, 64.34; H, 6.24; N, 15.00; C₂₅H₂₉N₅O₄ requires: C, 64.77; H, 6.31; N, 15.11%. δ = 7.75–7.60(dd, 1H), 7.55(s, 1H), 7.35–7.25(m, 2H), 7.10–7.00(m, 2H), 6.80–6.75(d, 2H), 6.10–6.00(d, 1H), 4.85–4.75(m, 2H), 4.65–4.45 (m, 2H), 3.95–3.85(d, 1H), 3.30–3.20(brs, 1H), 3.15–3.00(brs, 2H), 2.65–2.40(m, 2H), 1.90–1.70(m, 4H), 1.60(s, 3H), 1.35(s, 3H) ppm. |
| 29[5] | 3S, 4R/ 3R, 4S | (piperidin-2-one-5-yl) | —(CH₂)₂—C₆H₄—CH₃ | 2-(4-Methyl-phenyl)ethyl bromide | see Prep. 60 and 61 | 140–146 | δ = 7.20(s, 1H), 7.05–6.95(m, 3H), 6.95–6.85(m, 3H), 5.95–5.90(d, 1H), 4.60–4.50(t, 2H), 1.85–1.75(m, 1H), 1.35–1.30(d, 1H), 3.30–3.10(m, 2H), 3.10–2.90(m, 2H), 2.60–2.50(m, 2H), 2.30(s, 3H), 1.90–1.65(m, 4H), 1.55(s, 3H) 1.30(s, 3H) ppm. |
| 30[6] | 3S, 4R/ 3R, 4S | (piperidin-2-one-5-yl) | —(CH₂)₂—C₆H₄—CH₃ | 2-(2-Methyl-phenyl)ethyl bromide | see Prep. 60 and 61 | 169–172 | Found: C, 68.01; H, 6.67; N, 15.54; C₂₆H₃₁N₅O₃ requires: C, 67.67; H, 6.77; N, 15.18%. δ = 7.15–6.90(m, 5H), 6.90–6.85(d, 1H), 6.80–6.75(d, 1H), 5.95–5.90(d, 1H), 4.65–4.45(m, 2H), 3.85–3.75(m, 1H), 3.60–3.55(d, 1H), 3.30–3.10(m, 2H), 3.10–2.85(m, 2H), 2.60–2.45(m, 2H), 2.10(s, 3H), 1.90–1.65(m, 4H), 1.50(s, 3H), 1.30(s, 3H) ppm. |

-continued

| Ex. | Stereo-chem. | R⁴ | R⁵ | Alkylating agent | Tetrazole starting material ref. | m.p. (°C.) | Analysis/¹H-NMR (CDCl₃)¹ |
|---|---|---|---|---|---|---|---|
| 31[7] | 3S, 4R/ 3R, 4S | N-methyl-2-oxopiperidinyl | —CH₂—phenyl | Benzyl bromide | see Prep. 60 and 61 | 169–171 | Found: C, 66.20; H, 6.36; N, 16.08; $C_{24}H_{27}N_5O_3$ requires: C, 66.49; H, 6.28; N, 16.16%. δ = 7.50–7.40(dd, 1H), 7.40–7.30(m, 3H), 7.25–7.10(m, 3H), 7.00–6.90(d, 1H), 6.00–5.90(d, 1H), 5.70–5.55(ABq, 2H), 3.85–3.75(d, 1H), 3.75–3.60(brs, 1H), 3.10–2.95(m, 1H), 2.85–2.75(m, 1H), 2.60–2.30(m, 2H), 1.80–1.60(m, 3H), 1.55(s, 3H), 1.30(s, 3H) ppm. |
| 32[7] | 3S, 4R/ 3R, 4S | N-methyl-2-oxopiperidinyl | —(CH₂)₂—(3-methylphenyl) | 2-(3-Methyl-phenyl)ethyl bromide | see Prep. 60 and 61 | 173–176 | δ = 7.10–6.95(m, 4H), 6.90–6.85(d, 1H), 6.75–6.70(m, 2H), 5.95–5.90(d, 1H), 4.60–4.50(m, 2H), 3.85–3.75(m, 1H), 3.60(d, 1H), 3.25–3.10(m, 2H), 3.10–2.90(m, 2H), 2.60–2.50(m, 2H), 2.25(s, 3H), 1.90–1.65(m, 4H), 1.55(s, 3H), 1.30(s, 3H) ppm. |
| 33[8] | 3S, 4R/ 3R, 4S | N-methyl-2-oxopiperidinyl | —(CH₂)₂—(4-fluorophenyl) | 2-(4-Fluoro-phenyl)ethyl iodide[9] | see Prep. 60 and 61 | 140–144 | Found: C, 64.85; H, 6.10; N, 15.18; $C_{26}H_{28}N_5O_3F$ requires: C, 64.50; H, 6.06; N, 15.05%. δ = 7.15(d, 1H), 7.10–7.05(dd, 1H), 6.95–6.85(m, 5H), 6.00–5.90(d, 1H), 4.65–4.55(t, 2H), 3.85–3.75(m, 1H), 3.35(d, 1H), 3.30–3.10(m, 2H), 3.10–3.00(m, 1H), 2.95–2.85(m, 1H), 2.60–2.55(m, 2H), 1.90–1.65(m, 4H), 1.55(s, 3H), 1.30(s, 3H) ppm. |
| 34[10] | 3S, 4R/ 3R, 4S | N-methyl-2-oxopiperidinyl | —(CH₂)₂—(3,4-methylenedioxyphenyl) | 2-Methane-sulphonyl-oxy-1-(3,4-methylene-dioxy-phenyl)-ethane[11] | see Prep. 60 and 61 | 204–205 | δ = 7.15(s, 1H), 7.15–7.10(d, 1H), 6.90(d, 1H), 6.65–6.60(d, 1H), 6.40–6.35(m, 2H), 6.00–5.90(m, 3H), 4.60–4.50(t, 2H), 3.85–3.80(d, 1H), 3.30–3.20(brs, 1H), 3.15–2.90(m, 4H), 2.60–2.55(m, 2H), 1.90–1.70(m, 4H), 1.55(s, 3H), 1.30(s, 3H) ppm. |
| 35[12] | 3S, 4R/ 3R, 4S | N-methyl-2-oxopiperidinyl | —(CH₂)₂—phenyl | 2-Phenyl-ethyl iodide | see Prep. 60 and 61 | 105–115 | Found: C, 67.52; H, 6.72; N, 15.71; $C_{25}H_{29}N_5O_3$ requires: C, 67.09; H, 6.53; N, 15.65%. δ = 7.30–7.15(m, 3H), 7.10–6.85(m, 5H), 5.95–5.90(d, 1H), 4.65–4.50(m, 2H), 3.85–3.75(d, 1H), 3.35–3.15(m, 3H), 3.10–2.85(m, 2H), 2.60–2.50(m, 2H), 1.90–1.65(m, 4H), 1.50(s, 3H), 1.30(s, 3H) ppm. |
| 36[13] | 3S, 4R/ 3R, 4S | N-methyl-2-oxopiperidinyl | CH₃ | Methyl iodide | see Prep. 60 and 61 | 253–254 | (d₆-DMSO) δ = 7.60(d, 1H), 7.30(s, 1H), 7.00–6.95(d, 1H), 5.80–5.70(m, 2H), 5.65–5.60(brs, 1H), 3.75–3.70(d, 1H), 3.30(s, 1H), 3.20–3.10(m, 1H), 2.80–2.70(m, 1H), 2.50–2.30(m, 3H), 1.80–1.60(m, 4H), 1.45(s, 3H), 1.20(s, 3H) ppm. |

[1]Except where stated.
[2]Acetonitrile was used as a solvent for the reaction. Eluant for column chromatography was dichloromethane containing methanol (0% up to 2%) and acetic acid (0% up to 2%). The required compound was the lower Rf. product and it was crystallised from ethyl acetate.
[3]Acetonitrile was used as a solvent for the reaction and the mixture was initially sonicated for 30 minutes. Eluant for column chromatography was dichloromethane containing methanol (0% up to 2%) and acetic acid (0% up to 2%).
The corresponding tetrazole 2-alkylated product was obtained as the higher Rf. product from the column. The required compound was obtained as the lower Rf. product and was crystallised from diethyl ether.
[4]N,N-Dimethylformamide was used as a solvent for the reaction and ethyl acetate as the extraction solvent in the work-up. Eluant for column chromatography was toluene containing acetic acid (20% up to 40%). The corresponding tetrazole 2-alkylated product was obtained as the higher Rf. product from the column. The required compound was obtained as the lower Rf. product and was crystallised from ethyl acetate.

-continued

| Ex. | Stereo- chem. | R[4] | R[5] | Alkylating agent | Tetrazole starting material ref. | m.p. (°C.) | Analysis/$^1$H-NMR (CDCl₃)[1] |
|---|---|---|---|---|---|---|---|

[5]As footnote (4) except the lower Rf. product from the column was triturated with diethyl ether to provide the required compound.
[6]As footnote (4) except the lower Rf. product from the column was rechromatographed on silica eluting with dichloromethane containing methanol (5%) to provide the required product after trituration with diethyl ether.
[7]As footnote (4) except the required compound, obtained as the lower Rf. product, was crystallised from ethyl acetate/hexane.
[8]N,N-Dimethyl formamide was used as a solvent for the reaction. In the work-up reaction the mixture was partitioned between ethyl acetate and 5% aqueous sodium hydroxide, the layers separated and the aqueous layer extracted with ethyl acetate. The combined ethyl acetate extracts were dried (MgSO₄) and concentrated in vacuo to give an oil which was purified by chromatography on silica eluting with dichloromethane containing methanol (1% up to 2%) and acetic acid (1% up to 2%). The product-containing fractions were combined and concentrated in vacuo to give an oil which was crystallised from ethyl acetate to give the corresponding tetrazole 2-alkylated product, m.p. 210–212° C. The mother liquors from the crystallisation were concentrated in vacuo to give a gum which was further purified by chromatography on silica eluting with dichloromethane containing methanol (1% up to 2%) and acetic acid (1% up to 2%). The fractions containing the lower Rf product were combined and concentrated in vacuo to give a gum which was crystallised from ethyl acetate/ether to give the required product.
[9]See Preparation 75.
[10]The reaction mixture was sonicated for 24 hours. The corresponding tetrazole 2-alkylated product was obtained as the higher Rf. product from the column. The required product was obtained as the lower Rf. product from the column after trituration with diethyl ether.
[11]See Preparation 70.
[12]As footnote (4) except the lower Rf. product from the column was rechromatographed on silica eluting with dichloromethane containing methanol (1.5% up to 5%) and acetic acid (1.5% up to 5%) to provide the required product.
[13]The eluant used for column chromatography was toluene containing acetic acid (33% up to 50%). The corresponding tetrazole 2-alkylated product was obtained as the higher Rf. product from the column.
The required product was obtained as the lower Rf. product as a solid.

EXAMPLE 37

(3S,4R/3R,4S)-3,4-Dihydro-2,2-dimethyl-3-hydroxy-4-(2-oxopiperidin-1-yl)-6-(1-phenyl-1H-tetrazol-5-yl)-2H-benzo[b]pyran

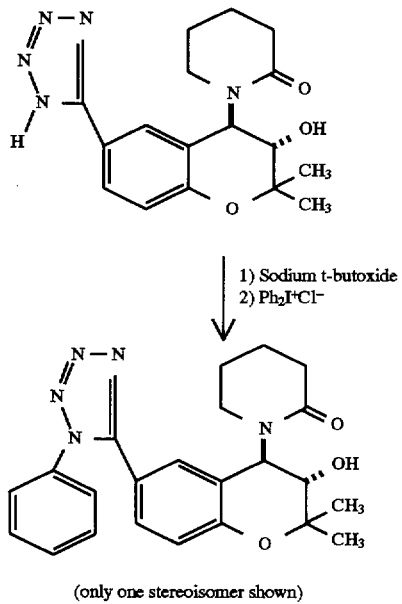

(only one stereoisomer shown)

Sodium metal (0.035 g) was added to tert-butanol (30 ml) and the mixture was heated under reflux for 30 minutes. On cooling to room temperature (3S,4R/3R,4S)-3,4-dihydro-2,2-dimethyl-3-hydroxy-4-(2-oxopiperidin-1-yl)-6-(1H-tetrazol-5-yl)-2H-benzo[b]pyran (see Preparations 60 and 61) (0.5 g) was added followed by diphenyliodonium chloride (0.5 g) and the mixture was heated under reflux for 10 hours. Sodium hydroxide (0.22 g) was added followed by further diphenyliodonium chloride (0.5 g) and the mixture was heated under reflux for a further 7 hours. The solution was concentrated in vacuo and the residue was partitioned between dichloromethane (50 ml) and 5% aqueous sodium hydroxide (50 ml). The layers were separated and the aqueous layer was extracted with dichloromethane (2×50 ml). The combined extracts were dried (MgSO₄) then concentrated in vacuo to give an oil which was purified by chromatography on silica eluting with dichloromethane containing methanol (1% up to 8%). The product-containing fractions were combined and concentrated in vacuo to give a gum which was triturated with ethyl acetate to give the title compound, 0.005 g.

$^1$H-NMR CDCl₃): δ=7.65–7.55(m,3H), 7.50–7.40(m, 2H), 7.45–7.25 (m,2H), 6.90–6.80(d,1H), 5.95–5.85(d,1H), 3.85–3.70(m,1H), 3.10–2.90(m,2H), 2.90–2.80(m,1H), 2.60–2.50(m,2H), 1.90–1.60(m,4H), 1.55(s,3H), 1.30(s,3H) ppm.

EXAMPLE 38

2,2-Dimethyl-6-(1-[2-(4-methoxyphenyl)ethyl]-1H-tetrazol-5-yl)-4-(2-oxo-1,2-dihydropyridin-1-yl)-2H-benzo[b]pyran

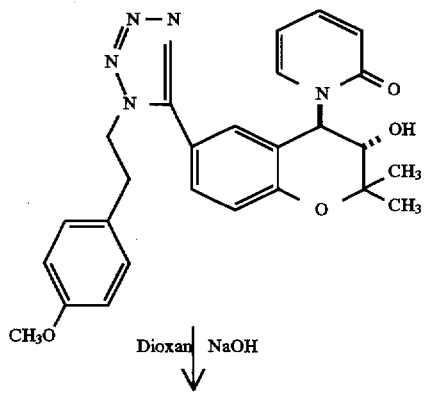

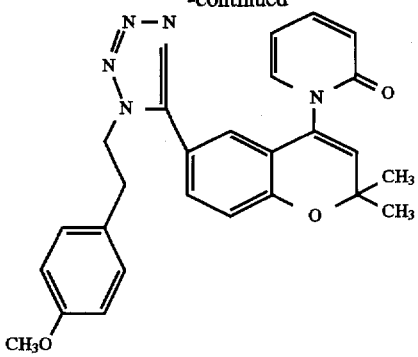

A mixture containing (3S,4R/3R,4S)-3,4-dihydro-2,2-dimethyl-3-hydroxy-6-(1-[2-(4-methoxyphenyl)ethyl]-1H-tetrazol-5-yl)-4-(2-oxo-1,2-dihydropyridin-1-yl)-2H-benzo[b]pyran (see Example 8) (0.65 g), polymer-supported sodium hydroxide (Merck 1567, 1 g) and anhydrous dioxan (30 ml) was heated under reflux for 15 minutes. On cooling to room temperature, the mixture was filtered, the dioxan was evaporated in vacuo, the residue was partitioned between water and dichloromethane, the organic layer was separated, concentrated in vacuo and the residue was purified by chromatography on silica eluting with dichloromethane containing methanol (2.5%). The product-containing fractions were combined and concentrated in vacuo to give an oil which was triturated with 2:1 hexane/ethyl acetate to give the title compound as a solid, 0.277 g, m.p. 156°–158° C. Found: C,68.21; H,5.58; N,15.27; $C_{26}H_{25}N_5O_3$ requires: C,68.56; H,5.53; N,15.37%.

$^1$H-NMR (CDCl$_3$): δ=7.45–7.35(m,1H), 7.25–7.15(dd, 1H), 7.00–6.85(m,5H), 6.75–6.70(d,2H), 6.60–6.50(d,1H), 6.30–6.20(t,1H), 5.80(s,1H), 4.60–4.40(m,2H), 3.75(s,3H), 3.20–3.05(m,2H), 1.65(s,3H), 1.55(s,3H) ppm.

EXAMPLES 39 to 46

The compounds of the following tabulated Examples of the general formula:

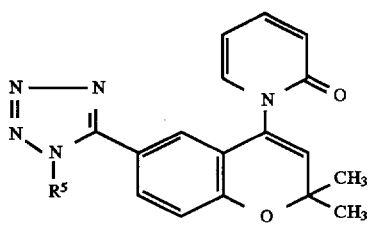

were prepared by similar methods to that of Example 38 using the appropriate starting materials.

| Ex. | R$^5$ | Reference for the preparation of the 3,4-dihydro-2H-benzo[b]pyran starting material | m.p. (°C.) | Analysis/$^1$H-NMR (CDCl$_3$) |
|---|---|---|---|---|
| 39[1] | —(CH$_2$)$_3$—C$_6$H$_5$ | see Example 14 | 130–132 | Found: C, 70.66; H, 5.77; N, 16.08; C$_{26}$H$_{25}$N$_5$O$_2$.0.025 CH$_2$Cl$_2$ requires: C, 70.78; H, 5.72; N, 15.86%. δ = 7.45–7.10(m, 8H), 7.00–6.90(m, 2H), 6.60–6.50(d, 1H), 6.30–6.20(t, 1H), 5.80(s, 1H), 4.35–4.25(t, 2H), 2.75–2.60(m, 2H), 2.30–2.15(m, 2H), 1.65(s, 3H), 1.60(s, 3H) ppm. |
| 40[2] | —(CH$_2$)$_4$—C$_6$H$_5$ | see Example 15 | 129–131 | Found: C, 71.37; H, 6.00; N, 15.20; C$_{27}$H$_{27}$N$_5$O$_2$ requires: C, 71.50; H, 6.00; N, 15.44%. δ = 7.50–7.35(m, 2H), 7.35–7.10(m, 6H), 7.05–6.90(m, 2H), 6.60–6.55(d, 1H), 6.30–6.20(t, 1H), 5.80(s, 1H), 4.35–4.25(t, 2H), 2.65–2.55(t, 2H), 1.95–1.85(m, 2H), 1.70–1.50(m, 2H), 1.65(s, 3H), 1.60(s, 3H) ppm. |
| 41[3] | —(CH$_2$)$_2$OCH$_2$—C$_6$H$_5$ | see Example 16 | — | δ = 7.70–7.65(d, 1H), 7.40–6.90(m, 9H), 6.60–6.55(d, 1H), 6.15–6.10(t, 1H) 5.75(s, 1H), 4.60–4.30(m, 2H), 4.40(s, 2H), 4.00–3.90(m, 2H), 1.65(s, 3H), 1.55(s, 3H) ppm. |
| 42[4] | —(CH$_2$)$_2$—C$_6$H$_4$—OCH$_3$ | see Example 18 | — | Found: C, 67.45; H, 5.46; N, 14.99; C$_{26}$H$_{25}$N$_5$O$_3$.0.1CH$_2$Cl$_2$ requires: C, 67.56; H, 5.47; N, 15.09%. δ = 7.45–7.35(m, 1H), 7.20–7.10(m, 2H), 6.95–6.90(m, 1H), 6.90–6.85(m, 2H), 6.75–6.70(dd, 1H), 6.60–6.50(m, 3H), 6.30–6.20(t, 1H), 5.80(s, 1H), 4.60–4.45(m, 2H), 3.70(s, 3H), 3.25–3.10(m, 2H), 1.65(s, 3H), 1.55(s, 3H) ppm. |

| Ex. | R[5] | Reference for the preparation of the 3,4-dihydro-2H-benzo[b]pyran starting material | m.p. (°C.) | Analysis/$^1$H-NMR (CDCl$_3$) |
|---|---|---|---|---|
| 43[4] | —(CH$_2$)$_2$—C$_6$H$_4$—OCH$_3$ | see Example 19 | — | δ = 7.45–7.35(m, 1H), 7.35–7.15(m, 2H), 7.10–7.05(dd, 1H), 6.95–6.85(m, 3H), 6.85–6.75(m, 2H), 6.65–6.55(d, 1H), 6.30–6.20(m, 1H), 5.80(s, 1H), 4.60–4.50(m, 2H), 3.70(s, 3H), 3.25–3.10(t, 2H), 1.65(s, 3H), 1.60(s, 3H) ppm. |
| 44[5] | —CH$_2$CH$_2$OCH$_3$ | see Example 20 | 141–144 | Found: C, 63.57; H, 5.72; N, 18.35; C$_{20}$H$_{21}$N$_5$O$_3$ requires: C, 63.31; N, 5.72; H, 18.46%. δ = 7.70–7.65(dd, 1H), 7.50–7.40(m, 1H), 7.30–7.20(m, 2H), 7.05–6.95(d, 1H), 6.65–6.55(d, 1H), 6.30–6.20(t, 1H), 5.75(s, 1H), 455–4.35(m, 2H), 3.90–3.80(m, 2H), 3.15(s, 3H), 1.65(s, 3H), 1.60(s, 3H) ppm. |
| 45[6] | CH$_3$ | see Example 25 | 205–210 | Found: C, 64.48; H, 5.09; N, 20.57; C$_{18}$H$_{17}$N$_5$O$_2$ requires: C, 64.46; H, 5.11; N, 20.88%. δ = 7.55–7.40(m, 2H), 7.25–7.20(d, 1H), 7.05–7.00(m, 2H), 6.65–6.60(d, 1H), 6.30–6.25(t, 1H), 5.80(s, 1H), 4.05(s, 3H), 1.65(s, 3H), 1.60(s, 3H) ppm. |
| 46[4] | —(CH$_2$)$_2$—C$_6$H$_5$ | see Example 21 | — | δ = 7.45–7.35(m, 1H), 7.30–7.20(m, 5H), 7.10–6.95(m, 3H), 6.90(d, 1H), 6.55–6.50(d, 1H), 6.25–6.20(t, 1H), 5.80(s, 1H), 4.60–4.40(m, 2H), 3.30–3.10(m, 2H), 1.65(s, 3H), 1.55(s, 3H) ppm. |

[1]The required product was obtained after trituration with diethyl ether.
[2]The reaction mixture was cooled to room temperature and the dioxan removed in vacuo to give the required compound as an oil which crystallised on standing.
[3]The required product was obtained after trituration with hexane.
[4]The required product was obtained as a foam after the column fractions had been concentrated in vacuo.
[5]The reaction mixture was cooled to room temperature, the solvent removed in vacuo and the residue partitioned between dichloromethane and water. The organic layer was separated and concentrated in vacuo to give an oil which afforded the required product after trituration with diethyl ether.
[6]The hot reaction mixture was filtered, cooled and concentrated in vacuo. The residue was crystallised from ethyl acetate to provide the required product.

EXAMPLE 47

(3S,4R/3R,4S)-3,4-Dihydro-2,2-dimethyl-3-hydroxy-4-(2-oxopiperidin-1-yl)-6-(1-[3-phenylprop-1-yl)-1H-tetrazol-5-yl)-2H-benzo[b]pyran

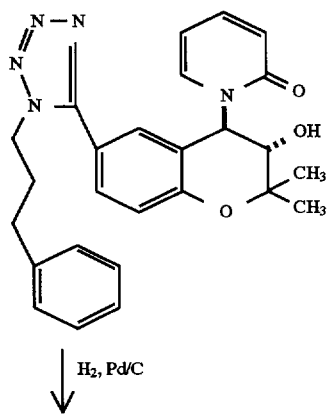

H$_2$, Pd/C

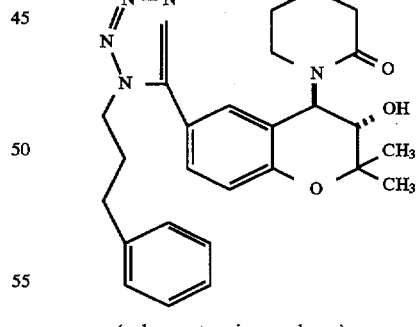

(only one stereoisomer shown)

A mixture containing (3S,4R/3R,4S)-3,4-dihydro-2,2-dimethyl-3-hydroxy-4-(2-oxo-1,2-dihydropyridin-1-yl)-6-(1-[3-phenylprop-1-yl]-1H-tetrazol-5-yl)-2H-benzo[b]pyran (see Example 14) (0.8 g), 10% palladium-on-carbon (0.1 g) and ethanol (40 ml) was hydrogenated at 50 psi (345 kPa) for 24 hours. A further batch of 10% palladium-on-carbon (0.1 g) was added and the hydrogenation continued for a further 24 hours. The mixture was filtered through a cellulose-based filter aid and the filtrate concentrated in vacuo to give a solid which was triturated with diethyl ether to give the title compound as a colourless solid, 0.66 g, m.p. 115°–122° C. Found: C,66.19; H,7.25; N,13.96; $C_{26}H_{31}N_6O_3 \cdot C_2H_6OH$ requires: C,66.25; H,7.35; N,13.80%.

$^1$H-NMR (CDCl$_3$): δ=7.40–7.20(m,5H), 7.15–7.10(d, 2H), 7.00–6.95(d,1H), 6.05–5.95(d,1H), 3.85–3.80(m,1 H), 3.80–3.65(m,2H), 3.45–3.40(m,1H), 3.15–3.00(m,1H), 3.00–2.85(m,1H), 2.75–2.65(m,2H), 2.65–2.55(m,2H), 2.35–2.20(m,2H), 1.90–1.60(m,4H), 1.55(s,3H), 1.35(s,3H) ppm.

EXAMPLES 48 to 57

The compounds of the following tabulated Examples of the general formula:

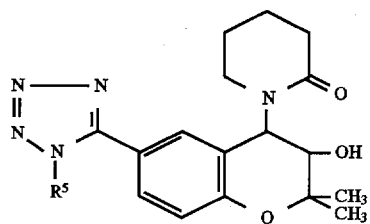

were prepared by similar methods to that of Example 47 using the appropriate starting materials.

| Ex. | Stereo-chem. | R$^5$ | Reference for the preparation of the pyridone starting material | m.p. (°C.) | Analysis/$^1$H-NMR (CDCl$_3$) |
|---|---|---|---|---|---|
| 48$^2$ | 3S, 4R/ 3R, 4S | –(CH$_2$)$_2$–C$_6$H$_4$–OH | see Example 72 | 217–220 | Found: C, 64.28; H, 6.45; N, 14.84; $C_{25}H_{29}N_5O_4$ requires: C, 64.78; H, 6.31; N, 15.11%. (d$_6$-DMSO): δ = 9.20(s, 1H), 7.35–7.30(d, 1H), 7.15(s, 1H), 6.95–6.90(d, 1H), 6.75–6.70(d, 2H), 6.55–6.50(d, 2H), 5.75–5.70(d, 1H), 6.60–5.55(d, 1H), 4.65–4.45(m, 2H), 3.70–3.65(m, 1H), 3.15–3.10(m, 1H), 3.00–2.85(m, 2H), 2.70–2.60(m, 1H), 2.40–2.30(m, 2H), 1.75–1.60(m, 3H), 1.45(s, 3H), 1.15(s, 3H) ppm. |
| 49$^2$ | 3S, 4R/ 3R, 4S | –(CH$_2$)$_4$–C$_6$H$_5$ | see Example 15 | 167–169 | Found: C, 68.18; H, 6.98; N, 14.69; $C_{27}H_{33}N_5O_3$ requires: C, 68.19; H, 6.99; N, 14.73%. δ = 7.45–7.10(m, 5H), 7.10–7.05(d, 2H), 7.00–6.95(d, 1H), 6.00–5.95(d, 1H), 4.40–4.30(t, 2H), 3.90–3.75(d, 1H), 3.50–3.40(brs, 1H), 3.10–2.90(m, 2H), 2.65–2.50(m, 4H), 2.00–1.50(m, 8H), 1.55(s, 3H), 1.30(s, 3H) ppm. |
| 50$^2$ | 3S, 4R/ 3R, 4S | –(CH$_2$)$_3$CO$_2$C$_2$H$_5$ | see Example 9 | — | Found: C, 60.06; H, 6.37; N, 15.02; $C_{23}H_{31}N_5O_5$ requires: C, 60.38; H, 6.83; N, 15.31%. δ = 7.55–7.45(d, 1H), 7.40(s, 1H), 7.05–6.95(d, 1H), 6.05–5.95((d, 1H), 4.50–4.40(t, 2H), 4.15–4.05(q, 2H), 3.90–3.80(m, 1H), 3.40(s, 1H), 3.10–2.90(m, 2H), 2.65–2.50(m, 2H), 2.45–2.35(m, 2H), 2.30–2.20(m, 2H), 1.95–1.70(m, 4H), 1.50(s, 3H), 1.30(s, 3H), 1.30–1.20(t, 3H) ppm. |
| 51$^2$ | 3S, 4R/ 3R, 4S | –CH$_2$CO$_2$C$_2$H$_5$ | see Example 10 | — | δ = 7.50–7.45(d, 1H), 7.30(s, 1H), 7.00–6.95(d, 1H), 5.95–5.90(d, 1H), 5.20–5.05(ABq, 2H), 4.35–4.25(q, 2H), 3.85–3.80(d, 1H), 3.50–3.40(brs, 1H), 3.15–3.05(m, 1H), 2.95–2.90(m, 1H), 2.60–2.50(m, 2H), 1.95–1.60(m, 4H), 1.50(s, 3H), 1.30–1.20(m, 6H) ppm. |

-continued

| Ex. | Stereo-chem. | R⁵ | Reference for the preparation of the pyridone starting material | m.p. (°C.) | Analysis/¹H-NMR (CDCl₃)[1] |
|---|---|---|---|---|---|
| 52[2,3] | 3S, 4R/ 3R, 4S | $-(CH_2)_2-N$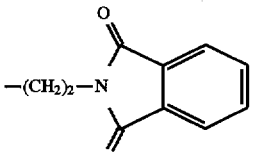 | see Example 17 | — | (d₆-DMSO): δ = 7.85–7.70(m, 4H), 7.30–7.25(d, 1H), 7.20(s, 1H), 6.70–6.65(d, 1H), 5.70–5.60(d, 1H), 5.55(d, 1H), 4.75–4.55(m, 2H), 3.90–3.75(m, 2H), 3.70–3.60(m, 1H), 3.20–3.10(m, 1H), 2.75–2.65(m, 1H), 2.50–2.30(m, 2H), 1.80–1.50(m, 4H), 1.40(s, 3H), 1.10(s, 3H) ppm. |
| 53[2] | 3S, 4R/ 3R, 4S | $-(CH_2)_2-$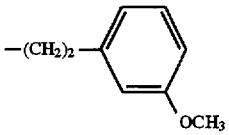$\quad OCH_3$ | see Example 18 | 195–197 | Found: C, 65.31; H, 6.53; N, 14.56; C₂₆H₃₁N₅O₄.0.1(C₂H₅)₂O requires: C, 65.38; H, 6.65; N, 14.44%. δ = 7.15–7.10(m, 1H), 7.05–6.95(m, 2H), 6.90–6.85(d, 1H), 6.75–6.70(dd, 1H), 6.50–6.45(d, 1H), 6.40(s, 1H), 5.95–5.90(d, 1H), 4.65–4.50(m, 2H), 3.85–3.75(m, 1H), 3.70(s, 3H), 3.35–3.30(m, 1H), 3.30–3.10(m, 2H), 3.05–2.85(m, 2H), 2.60–2.50(m, 2H), 1.90–1.70(m, 4H), 1.55(s, 3H), 1.30(s, 3H) ppm. |
| 54[2,4] | 3S, 4R/ 3R, 4S | $-(CH_2)_2-$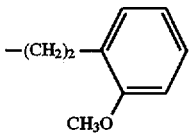 $CH_3O$ | see Example 19 | 190–192 | Found: C, 65.26; H, 6.66; N, 14.63; C₂₆H₃₁N₅O₄.0.125(C₂H₅)₂O requires: C, 65.37; H, 6.67; N, 14.38%. δ = 7.25–7.15(m, 1H), 7.15–7.10(m, 2H), 6.90–6.70(m, 4H), 5.95–5.90(d, 1H), 4.70–4.45(m, 2H), 3.85–3.75(m, 1H), 3.70(s, 3H), 3.50–340(m, 1H), 3.25–3.10(m, 2H), 3.05–2.90(m, 2H), 2.60–2.50(m, 2H), 1.90–1.70(m, 4H), 1.55(s, 3H), 1.30(s, 3H) ppm. |
| 55[2] | 3S, 4R/ 3R, 4S | $-CH_2CH_2OCH_3$ | see Example 20 | 200–202 | Found: C, 59.69; H, 6.76; N, 17.29; C₂₀H₂₇N₅O₄ requires: C, 59.83; H, 6.78; N, 17.44%. δ = 7.65–7.60(d, 1H), 7.50(s, 1H), 7.00–6.95(d, 1H), 6.05–5.95(d, 1H), 4.55–4.40(m, 2H), 3.95–3.90(t, 2H), 3.90–3.80(d, 1H), 3.45–3.35(brs, 1H), 3.30(s, 3H), 3.10–2.90(m, 2H), 2.65–2.50(m, 2H), 1.90–1.65(m, 4H), 1.55(s, 3H), 1.30(s, 3H) ppm. |
| 56[2,5] | 3S, 4R/ 3R, 4S | $-(CH_2)_2-$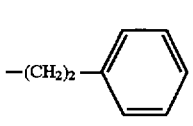 | see Example 21 | 168–170 | Found: C, 66.98; H, 6.52; N, 15.56; C₂₅H₂₉N₅O₃ requires: C.67.09; H, 6.53; N, 15.65%. δ = 7.30–7.15(m, 3H), 7.10–6.85(m, 5H), 5.95–5.90(d, 1H), 4.65–4.50(m, 2H), 3.85–3.75(m, 1H), 3.65(d, 1H), 3.30–3.15(m, 2H), 3.10–2.95(m, 1H), 2.95–2.85(m, 1H), 2.60–2.50(t, 2H), 1.90–1.60(m, 4H), 1.50(s, 3H), 1.30(s, 3H) ppm. |
| 57[2,5] | 3S, 4R/ 3R, 4S | $-(CH_2)_2-$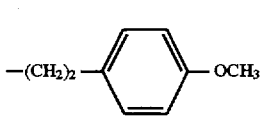$-OCH_3$ | see Example 8 | 178–180 | Found: C, 63.92; H, 6.54; N, 14.41; C₂₆H₃₁N₅O₄.0.5H₂O requires: C, 64.18; H, 6.63; N, 14.39%. δ = 7.15(s, 1H), 7.10–7.00(dd, 1H), 6.90–6.80(m, 3H), 6.80–6.70(d, 2H), 6.00–5.90(d, 1H), 4.60–4.50(t, 2H), 3.90–3.75(m, 1H), 3.80(s, 3H), 3.50–3.45(d, 1H), 3.25–3.10(m, 2H), 3.10–2.90(m, 2H), 2.60–2.50(t, 2H), 1.90–1.65(m, 4H), 1.50(s, 3H), 1.30(s, 3H) ppm. |

[1]Except where stated.
[2]Hydrogenation carried out at 50° C.
[3]The reaction mixture was filtered, the filtrate concentrated in vacuo and the solid obtained triturated with hot methanol, filtered and dried to provide the required product.
[4]The filtrate obtained after passage through the cellulose-based filter aid was concentrated in vacuo to give an oil which was purified by chromatography on silica eluting with dichloromethane containing methanol (2.5%). The product-containing fractions were combined and concentrated in vacuo to give a foam which was triturated with diethyl ether to give the required product as a solid.

| Ex. | Stereo-chem. | R[5] | Reference for the preparation of the pyridone starting material | m.p. (°C.) | Analysis/$^1$H-NMR (CDCl$_3$) |
|---|---|---|---|---|---|

[5]The required product was obtained after recrystallisation of the crude product from ethyl acetate.

[6]After the hydrogenation the reaction mixture was filtered through a cellulose–based filter aid and the filtrate concentrated in vacuo to give a gum which was azeotroped with dichloromethane to give a foam. The foam was taken up in ethyl acetate whereupon a solid precipitated which was purified further by chromatography on silica eluting with dichloromethane containing methanol (5%). The product-containing fractions were combined and concentrated in vacuo to give a gum which was azeotroped with dichloromethane to give a foam. The foam was crystallised from ethyl acetate to give a solid which was further purified by chromatography on silica eluting with ethyl acetate containing dichloromethane (20% down to 0%). The product-containing fractions were combined and concentrated in vacuo to give a gum which was azeotroped with dichloromethane. The resulting solid was triturated with diethyl ether and dried to give the required product as a solid.

EXAMPLE 58

(3S,4R)-3,4-Dihydro-3-hydroxy-4-(3-hydroxypyridazin-6-yl)oxy-6-(1-[3-methoxycarbonylprop-1-yl]-1H-tetrazol-5-yl)-2,2,3-trimethyl-2H-benzo[b]pyran

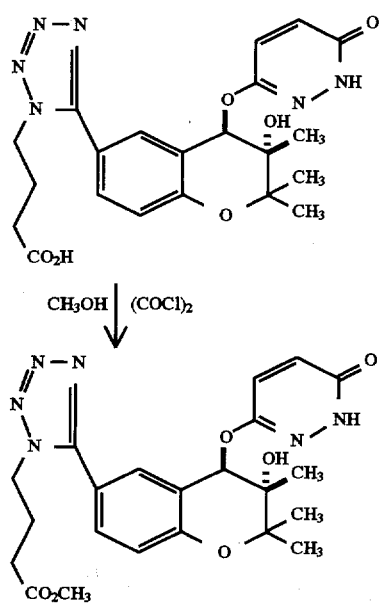

Oxalyl chloride (10 drops) was added to a solution of (3S,4R)-6-(1-[3-carboxyprop-1-yl]-1H-tetrazol-5-yl)-3,4-dihydro-3-hydroxy-4-(3-hydroxypyridazin-6-yl)oxy-2,2,3-trimethyl-2H-benzo[b]pyran (see Preparation 48) (0.15 g) in anhydrous tetrahydrofuran (5 ml). After 10 minutes the mixture was concentrated in vacuo and the residue azeotroped with anhydrous dichloromethane (3×5 ml). Dichloromethane (4 ml) was added followed by methanol (0.5 ml). After 15 minutes the solution was concentrated in vacuo and the residue purified by chromatography on silica eluting with dichloromethane containing methanol (2.5% up to 5%). The product-containing fractions were concentrated in vacuo to give an oil which was triturated with hexane to give the title compound as a foam, 0.13 g.

$^1$H-NMR (CDCl$_3$): δ=7.75(s,1H), 7.60–7.55(dd,1H), 7.15–7.10(d,1H), 7.05–6.95(m,2H), 6.00(s,1H), 4.50–4.40 (m,2H), 3.65(s,3H), 3.55–3.30(brs,1H), 2.50–2.40(m,2H), 2.30–2.20(m,2H), 1.50(s,3H), 1.45(s,3H), 1.30(s,3H) ppm.

EXAMPLES 59 to 61

The compounds of the following tabulated Examples of the general formula:

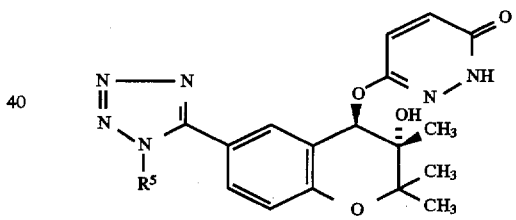

were prepared by similar methods to that of Example 58 using the appropriate starting materials.

| Ex. | R[5] | m.p. (°C.) | Analysis/$^1$H-NMR (CDCl$_3$) |
|---|---|---|---|
| 59[1] | —(CH$_2$)$_3$—CO$_2$CH$_2$CF$_3$ | — | Found: C, 50.08; H, 4.66; N, 14.94; C$_{23}$H$_{25}$F$_3$N$_6$O$_6$.0.2CH$_2$Cl$_2$ requires: C, 50.16; H, 4.61; N, 15.13%. 67 = 7.70(s, 1H), 7.65–7.55(dd, 1H), 7.15–7.10(d, 1H), 7.10–6.95(m, 2H), 6.05(s, 1H), 4.50–4.35(m, 4H), 3.45(s, 1H), 2.60–2.50(m, 2H), 2.35–2.20(m, 2H), 1.50(s, 3H), 1.45(s, 3H), 1.30(s, 3H) ppm. |
| 60[2] | —(CH$_2$)$_3$—CO$_2$CH$_2$—⌬ | — | δ = 10.95–10.85(brs, 1H), 7.80–7.75(d, 1H), 7.65–7.55(dd, 1H), 7.45–7.30(m, 5H), 7.20–7.15(d, 1H), 7.10–7.00(m, 2H), 6.05(s, 1H), 5.10(s, 2H), 4.55–4.45(m, 2H), 3.40(s, 1H), 2.55–2.50(m, 2H), 2.40–2.25(m, 2H), 1.55(s, 3H), 1.50(s, 3H), 1.35(s, 3H) ppm. |

| Ex. | R⁵ | m.p. (°C.) | Analysis/¹H-NMR (CDCl₃) |
|---|---|---|---|
| 61[3] | 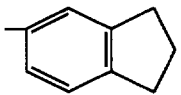 —(CH₂)₃—CO₂— | — | Found: C, 63.04; H, 5.62; N, 14.43; C₃₀H₃₂N₆O₆ requires: C, 62.92; H, 5.63; N, 14.68%. δ = 11.00–10.90(brs, 1H), 7.70(d, 1H), 7.55–7.50(dd, 1H), 7.15–7.10(d, 1H), 7.10–7.05(d, 1H), 7.00–6.90(m, 2H), 6.85(s, 1H), 6.75–6.70(dd, 1H), 5.95(s, 1H), 4.55–4.45(t, 2H), 3.45–3.40(s, 1H), 2.90–2.80(m, 4H), 2.70–2.60(t, 2H), 2.40–2.25(m, 2H), 2.10–2.00(m, 2H), 1.45(s, 3H), 1.40(s, 3H), 1.30(s, 3H) ppm. |

[1]Pyridine was added together with 2,2,2-trifluoroethanol. No trituration with hexane was carried out.
[2]Pyridine was added together with benzyl alcohol. The product obtained from the column was triturated with diethyl ether to provide the required product.
[3]Pyridine was added together with 5-indanol. No trituration with hexane was carried out.

EXAMPLE 62

(3S,4R)-3,4-Dihydro-3-hydroxy-4-(3-hydroxypyridazin-6-yl)oxy-6-(1-[3-phenoxycarbonylprop-1-yl]-1H-tetrazol-5-yl)-2,2,3-trimethyl-2H-benzo[b]pyran

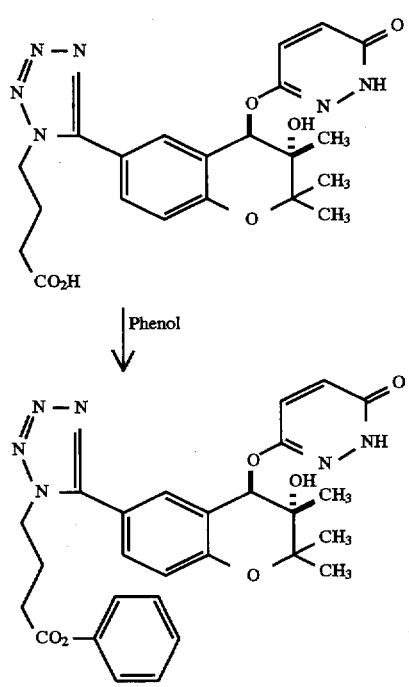

1-(3-Dimethylaminopropyl)-3-ethylcarbodiimide hydrochloride (0.092 g) was added to a solution of (3S,4R)-6-(1-[3-carboxyprop-1-yl]-1H-tetrazol-5-yl)-3,4-dihydro-3-hydroxy-4-(3-hydroxypyridazin-6-yl)oxy-2,2,3-trimethyl-2H-benzo[b]pyran (see Preparation 48) (0.2 g) and triethylamine (0.05 g) in anhydrous dichloromethane (5 ml) and the mixture was stirred at room temperature for 1.75 hours. Phenol (0.06 g) was added and the mixture was stirred at room temperature for 18 hours then concentrated in vacuo. The residue was purified by chromatography on silica eluting with dichloromethane containing methanol (2.5% up to 5%). The product-containing fractions were combined and concentrated in vacuo to give the title compound as a foam, 0.042 g.

¹H-NMR (CDCl₃): δ=7.75(d,1H), 7.80–7.75(dd,1H), 7.40–7.30(m,2H), 7.30–7.20(m,1H), 7.10–6.90(m,5H), 5.95 (s,1H), 4.55–4.50(m,2H), 3.50(brs,1H), 2.75–2.65(m,2H), 2.40–2.30(m,2H), 1.50(s,3H), 1.45(s,3H), 1.30(s,3H) ppm.

EXAMPLE 63

(3S,4R)-3,4-Dihydro-3-hydroxy-4-(3-hydroxypyridazin-6-yl)oxy-2,2,3-trimethyl-6-(1-[3-vinyloxycarbonylprop-1-yl]-1H-tetrazol-5-yl)-2H-benzo[b]pyran

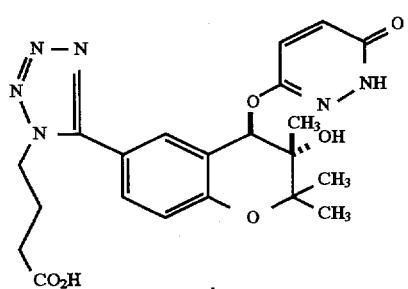

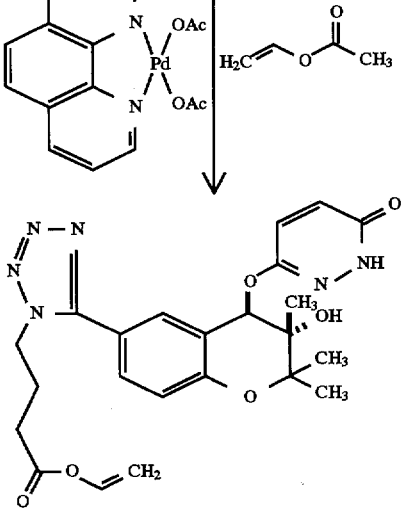

A mixture containing (3S,4R)-6-(1-[3-carboxyprop-1-yl]-1H-tetrazol-5-yl)-3,4-dihydro-3-hydroxy-4-(3-hydroxypyridazin-6-yl)oxy-2,2,3-trimethyl-2H-benzo[b]pyran (see Preparation 48) (0.5 g), vinyl acetate (5 ml), 1,10-phenanthrolinylpalladium(II) acetate (see Tetrahedron, 28, 233(1972)) (0.05 g), dichloromethane (10 ml) and anhydrous tetrahydrofuran (10 ml) was heated under reflux for 2 days. The mixture was concentrated in vacuo and the residue was purified by chromatography on silica eluting with ethyl acetate. The product-containing fractions were combined and concentrated in vacuo to give the title compound as a foam, 0.18 g. Found: C,57.07; H,5.48; N,17.24; C₂₃H₂₆N₆O₆ requires: C,57.25; H,5.43; N,17.42%.

¹H-NMR (CDCl₃): δ=11.30–11.25(brs, 1H), 7.75(d,1H), 7.65–7.55(dd,1H), 7.25–7.10(m,2H), 7.10–7.00(m,2H), 6.05(s,1H), 4.95–4.85(dd,1H), 4.65–4.60(dd,1H), 4.55–4.45 (t,2H), 3.60(brs,1H), 2.60–2.50(t,2H), 2.40–2.25(m,2H), 1.60(s,3H), 1.50(s,3H), 1.35(s,3H) ppm.

EXAMPLE 64

(3S,4R)-3,4-Dihydro-3-hydroxy-4-(3-hydroxypyridazin-6-yl)oxy-6-(1-[3-(pivaloyloxymethoxycarbonyl)prop-1-yl]-1H-tetrazol-5-yl)-2,2,3-trimethyl-2H-benzo[b]pyran

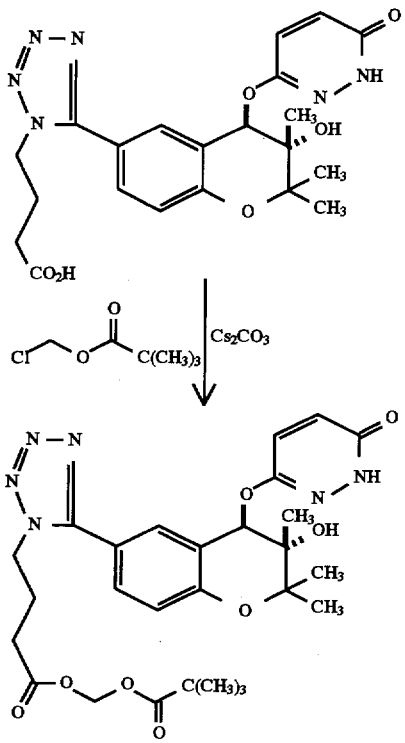

Cesium carbonate (0.18 g) was added to a solution of (3S,4R)-6-(1-[3-carboxyprop-1-yl]-1H-tetrazol-5-yl)-3,4-dihydro-3-hydroxy-4-(3-hydroxypyridazin-6-yl)oxy-2,2,3-trimethyl-2H-benzo[b]pyran (see Preparation 48) (0.5 g) in anhydrous N,N-dimethylacetamide (20 ml) and the mixture was stirred with heating until an almost homogeneous solution was obtained. On cooling to room temperature pivalic acid chloromethyl ester (0.18 ml) was added and the mixture was stirred at room temperature for 3 days then concentrated in vacuo and the residue partitioned between dichloromethane (100 ml) and ice-cold 1M hydrochloric acid (50 ml). The layers were separated, the dichloromethane layer dried (MgSO₄) and concentrated in vacuo. The residue was purified by chromatography on silica eluting with ethyl acetate. The product-containing fractions were combined and concentrated in vacuo to give the title compound as a foam, 0.39 g, m.p. 90°–100° C. Found: C,56.87; H,6.06; N,14.76; C₂₇H₃₄N₆O₈ requires: C,56.83; H,6.00; N,14.73%.

¹H-NMR (CDCl₃): δ=11.30–11.25(brs,1 H), 7.70(d,1H), 7.55–7.45(dd,1H), 7.15–7.10(d, 1H), 7.00–6.90(m,2H), 6.00 (s,1H), 5.70–5.65(ABq,2H), 4.50–4.40(t,2H), 3.60–3.55 (brs,1H), 2.50–2.40(m,2H), 2.25–2.15(m,2H), 1.50(s,3H), 1.45(s,3H), 1.30(s,3H), 1.15(s,9H) ppm.

EXAMPLE 65

3S,4R)-3,4-Dihydro-6-1-3-ethoxycarbonyloxymethoxycarbonyl)prop-1-yl]-1H-tetrazol-5-yl)-3-hydroxy-4-(3-hydroxypyridazin-6-yl)oxy-2,2,3-trimethyl-2H-benzo[b]pyran

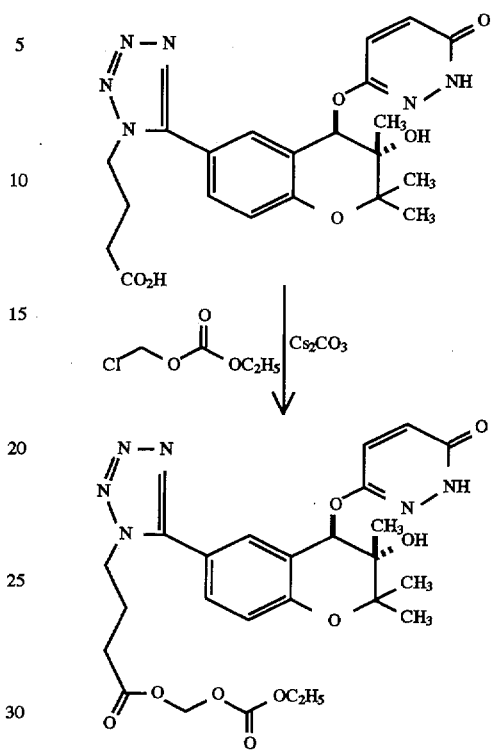

Cesium carbonate (0.18 g) was added to a solution of (3S,4R)-6-(1-[3-carboxypyrop-1-yl]-1H-tetrazol-5-yl)-3,4-dihydro-3-hydroxy-4-(3-hydroxypyridazin-6-yl)oxy-2,2,3-trimethyl-2H-benzo[b]pyran (see Preparation 48) (0.5 g) in anhydrous N,N-dimethylacetamide (20 ml) and the mixture was stirred with heating until an almost homogeneous solution was obtained. On cooling to room temperature chloromethyl ethyl carbonate (see Preparation 77) (0.17 g) was added and the mixture was stirred at room temperature for 24 hours then partitioned between diethyl ether (100 ml) and ice-cold 1M hydrochloric acid (50 ml). The layers were separated, the ethereal layer washed with water (50 ml) and saturated aqueous sodium chloride solution (50 ml), then dried (MgSO₄) and concentrated in vacuo. The residue was purified by chromatography on silica eluting with dichloromethane containing methanol (0% up to 6%). The product-containing fractions were combined and concentrated in vacuo to give the title compound, 0.06 g. Found: C,53.84; H,5.55; N,14.97; C₂₆H₃₀N₆O₅ requires: C,53.76; H,5.41; N,15.05%.

¹H-NMR (CDCl₃): δ=11.65–11.55(brs,1 H), 7.70(d,1H), 7.60–7.55(dd,1H), 7.20–7.15(d,1H), 7.10–6.95(m,2H), 6.10 (s,1H), 5.70(s,2H), 4.50–4.40(t,2H), 4.30–4.20(q,2H), 3.80 (brs,1H), 2.55–2.45(m,2H), 2.30–2.20(m,2H), 1.55(s,3H), 1.50(s,3H), 1.35–1.25(m,6H) ppm.

EXAMPLE 66

(3S,4R/3R,4S)-6-(1-[2-Benzoyloxyethyl]-1H-tetrazol-5-yl)-3,4-dihydro-2,2-dimethyl-3-hydroxy-4-(2-oxopiperidin-1-yl)-2H-benzo[b]pyran

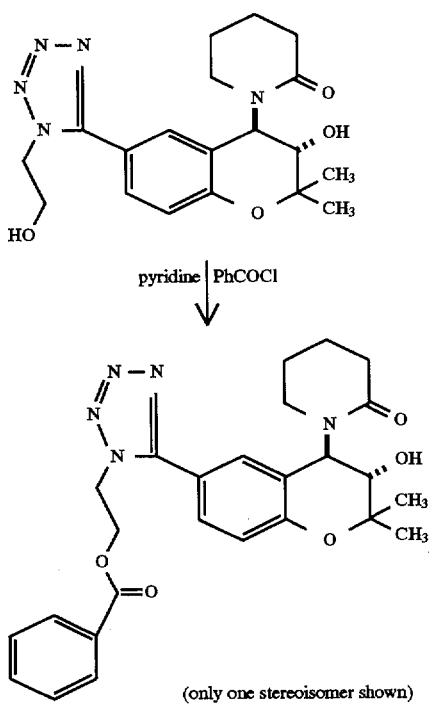

(only one stereoisomer shown)

A mixture containing (3S,4R/3R,4S)-3,4-dihydro-2,2-dimethyl-3-hydroxy-6-(1-[2-hydroxyethyl]-1H-tetrazol-5-yl)-4-(2-oxopiperidin-1-yl)-2H-benzo[b]pyran (see Example 71) (0.211 g), benzoyl chloride (0.078 g) and pyridine (1 ml) was shaken in a vial for 30 minutes. The mixture was added to water (5 ml) and extracted with ethyl acetate (3×5 ml). The combined ethyl acetate extracts were concentrated in vacuo to give a colourless solid which was purified by chromatography on silica eluting with dichloromethane containing methanol (5%). The product-containing fractions were combined and concentrated in vacuo to give the title compound as a solid, 0.115 g, m.p. 233°–236° C. Found: C,63.31; H,5.63; N,14.21; $C_{26}H_{29}N_5O_5$ requires: C,63.53; H,5.95; N,14.25%.

$^1$H-NMR (CDCl$_3$): δ=7.85–7.80(d,2H), 7.60–7.55(m, 1H), 7.50–7.35(m,4H), 6.90(d,1H), 5.95–5.90(d,1H), 4.90–4.65(m,4H), 3.85–3.75(m,1H), 3.40(d,1H), 3.10–2.90 (m,2H), 2.60–2.50(m,2H), 1.90–1.70(m,4H), 1.50(s,3H), 1.25(s,3H) ppm.

EXAMPLE 67

(3S,4R/3R,4S)-6-(1-[2-Acetyloxyethyl]-1H-tetrazol-5-yl)-3,4-dihydro-2,2-dimethyl-3-hydroxy-4-(2-oxopiperidin-1-yl)-2H-benzo[b]pyran

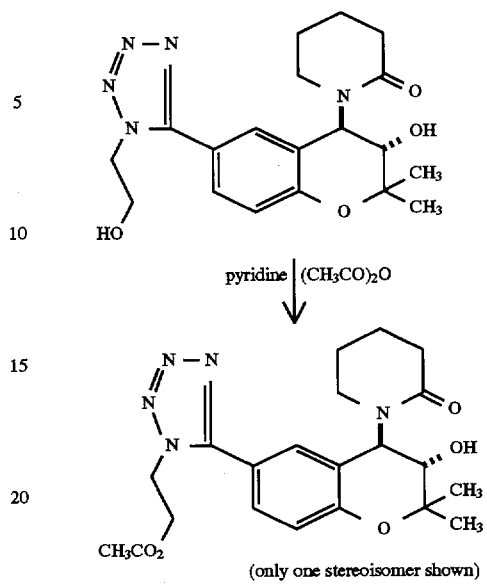

(only one stereoisomer shown)

A mixture containing (3S,4R/3R,4S)-3,4-dihydro-2,2-dimethyl-3-hydroxy-6-(1-[2-hydroxyethyl]-1H-tetrazol-5-yl)-4-(2-oxopiperidin-1-yl)-2H-benzo[b]pyran (see Example 71) (0.2 g), acetic anhydride (0.047 g) and pyridine (2 ml) was shaken in a vial for 30 minutes. The mixture was added to water (5 ml) and extracted with ethyl acetate (3×5 ml). The combined extracts were concentrated in vacuo to give a foam which was purified by chromatography on silica eluting with dichloromethane containing methanol (5%). The product-containing fractions were combined and concentrated in vacuo to give the title compound as a foam, 0.117 g. Found: C,56.05; H,5.90; N,15.18; $C_{21}H_{27}N_5O_5$·0.33CH$_2$Cl$_2$ requires: C,55.96; H,6.09; N,15.29%.

$^1$H-NMR (CDCl$_3$): δ=7.55–7.45(d,1H), 7.35(s,1H), 7.05–6.95(d,1H), 6.05–5.95(d,1H), 4.70–4.60(m,2H), 4.55–4.45(m,2H), 3.90–3.80(m,1H), 3.35–3.30(d,1H), 3.15–2.90(m,2H), 2.60–2.50(m,2H), 1.90(s,3H), 1.95–1.70 (m,4H), 1.55(s,3H), 1.30(s,3H) ppm.

EXAMPLE 68

(3S,4R)-3,4-Dihydro-6-(1-[N-(ethoxycarbonylmethyl)carbamoylmethyl]-1H-tetrazol-5-yl)-3-hydroxy-4-(3-hydroxypyridazin-6-yl)oxy-2,2,3-trimethyl-2H-benzo[b]pyran

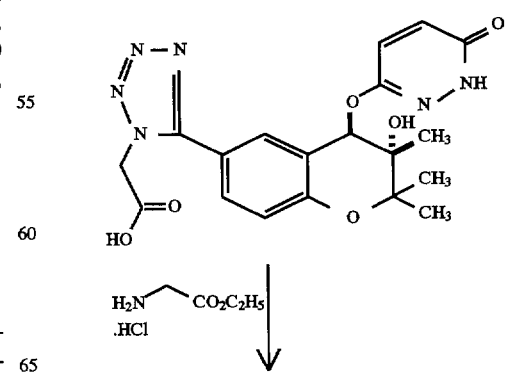

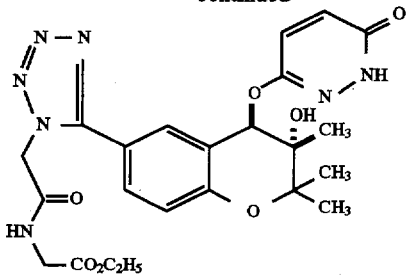

1-(3-Dimethylaminopropyl)-3-ethylcarbodiimide hydrochloride (0.192 g) was added to a solution of (3S,4R)-6-(1-carboxymethyl-1H-tetrazol-5-yl)-3,4-dihydro-3-hydroxy-4-(3-hydroxypyridazin-6-yl)oxy-2,2,3-trimethyl-2H-benzo[b]pyran (see Preparation 69) (0.214 g), N-methylmorpholine (0.162 g), 1-hydroxybenzotriazole (0.068 g) and ethyl glycinate hydrochloride (0.084 g) in anhydrous dichloromethane (5 ml) at 0° C. The mixture was allowed to warm to room temperature and stirred for 3 days. The mixture was concentrated in vacuo and the residue partitioned between ethyl acetate (30 ml) and water (30 ml). The layers were separated and the ethyl acetate layer was washed with saturated aqueous sodium chloride solution (30 ml) then dried (MgSO$_4$) and concentrated in vacuo to give the title compound, 0.09 g, m.p. 130°–140° C.

$^1$H-NMR (CDCl$_3$): δ=11.85–11.60(brs,1H), 7.85(s,1H), 7.80–7.60(m,2H), 7.15–7.10(d,1H), 7.05–6.95(m,2H), 5.95 (s,1H), 5.30–5.10(ABq,2H), 4.25–4.10(q,2H), 4.10–4.00(d, 2H), 2.20–1.70(brs,1H), 1.55(s,3H), 1.50(s,3H), 1.35(s,3H), 1.30–1.20(t,3H) ppm.

EXAMPLE 69

(3S,4R)-4-(2-Cyano-3-methylquanidino)-3,4-dihydro-3-hydroxy-6-(1-[3-(N-methylcarbamoyl)prop-1-yl]-1H-tetrazol-5-yl)-2,2,3-trimethyl-2H-benzo[b]pyran

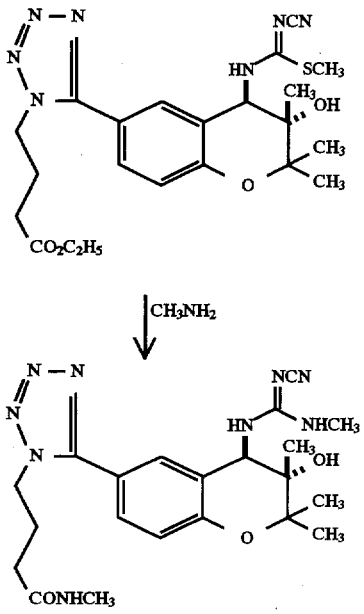

A mixture of (3S,4R)-4-(3-cyano-2-methylisothioureido)-3,4-dihydro-6-(1-[3-ethoxycarbonylprop-1-yl]-1H-tetrazol-5-yl)-3-hydroxy-2,2,3-trimethyl-2H-benzo[b]pyran (see Example 75) (0.2 g) and methylamine (2 ml of a 33% solution in industrial methylated spirit) was allowed to stand at room temperature for 4 hours. Further methylamine (2 ml of a 33% solution in Industrial methylated spirit) was added and the mixture was allowed to stand for a further 3 days. The solvent was removed in vacuo and the resulting foam was purified by chromatography on silica eluting with dichloromethane containing methanol (5% up to 10%). The product-containing fractions were combined and concentrated in vacuo to give the title compound as a solid, 0.15 g, m.p. 143°–146° C.

$^1$H-NMR (d$_6$-DMSO): δ=7.75–7.65(m,1H), 7.55–7.45(m, 2H), 7.30–7.25(brs,1 H), 6.95–6.85(m,2H), 5.40–5.15(brm, 2H), 4.45–4.35(m,2H), 2.80(d,3H), 2.10–1.95(m,4H), 1.40 (s,3H), 1.30(s,3H), 1.05(s,3H) ppm.

EXAMPLE 70

(3S,4R/3R,4S)-3,4-Dihydro-3-hydroxy-6-(1-[2-(4-hydroxyphenyl)ethyl]-1H-tetrazol-5-yl)-4-(3-hydroxypyridazin-6-yl)oxy-2,2,3-trimethyl-2H-benzo[b]pyran

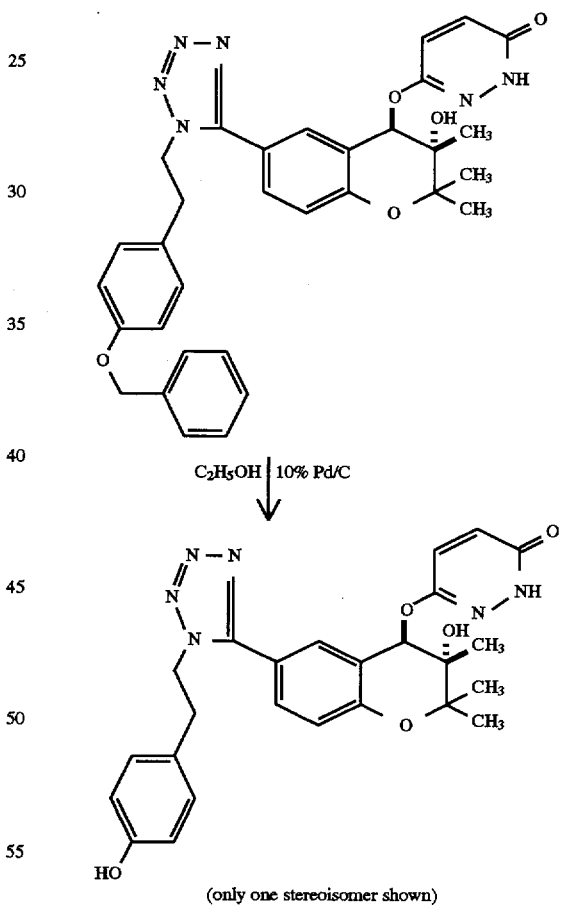

(only one stereoisomer shown)

A mixture containing (3S,4R/3R,4S)-6-(1-[2-(4-Benzyloxyphenyl)ethyl]-1 H-tetrazol-5-yl)-3,4-dihydro-3-hydroxy-4-(3-hydroxypyridazin-6-yl)oxy-2,2,3-trimethyl-2H-benzo[b]pyran (see Example 5) (0.35 g), 10% palladium-on-carbon (0.05 g) and ethanol (50 ml) was hydrogenated at 50° C. and 345 kPa (50 psi) for 2 hours. The mixture was filtered through a cellulose based filter aid and the filtrate was concentrated in vacuo to give a foam which was purified by chromatography on silica eluting with ethyl acetate containing methanol (4%) and concentrated aqueous ammonia (0.5%). The product-containing fractions were combined and concentrated in vacuo to give a gum which was triturated with diethyl ether to give the title compound as a colourless foam, 0.15 g, m.p. 120°–160° C. (with foaming).

$^1$H-NMR (d$_6$-DMSO): δ=9.25–9.10(brs,1H), 7.45(s,1H), 7.35–7.30(d,1H), 7.25–7.20(d,1H), 6.95–6.85(m,2H), 6.75–6.65(d,2H), 6.55–6.45(d,2H), 5.90(s,1H), 5.40–5.30 (brs,1H), 4.55–4.45(t, 2H), 2.95–2.85(t,2H), 1.40(s,3H), 1.30(s,3H), 1.20(s,3H) ppm.

EXAMPLE 71

(3S,4R/3R,4S)-3,4-Dihydro-2,2-dimethyl-3-hydroxy-6-(1-[2-hydroxyethyl]-1H-tetrazol-5-yl)-4-(2-oxopiperidin-1-yl)-2H-benzo[b]pyran

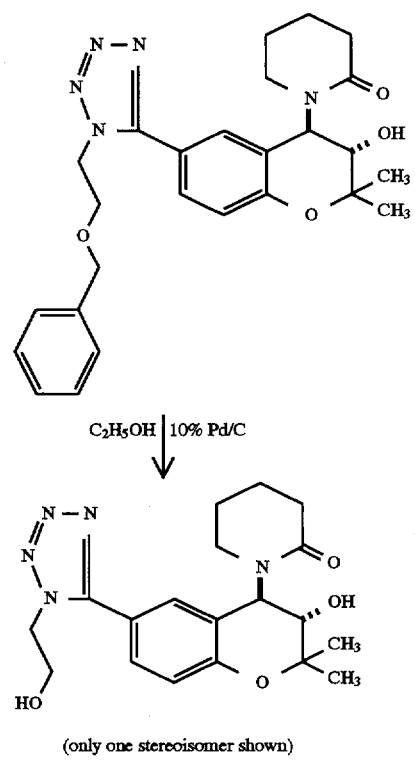

(only one stereoisomer shown)

A mixture containing (3S,4R/3R,4S)-6-(1-[2-benzyloxyethyl]-1H-tetrazol-5-yl)-3,4-dihydro-2,2-dimethyl-3-hydroxy-4-(2-oxopiperidin-1-yl)-2H-benzo[b] pyran (see Example 23) (0.67 g), 10% palladium-on-carbon (0.2 g) and ethanol (50 ml) was hydrogenated at 345 kPa (50 psi) and 50° C. for 16 hours. The catalyst was filtered off and the filtrate was concentrated in vacuo to give a foam which was purified by chromatography on silica eluting with dichloromethane containing methanol (5%). The product-containing fractions were combined and concentrated in vacuo to give a foam which was triturated with diethyl ether to give the title compound as a solid, 0.45 g, m.p. 217°–219° C. Found: C,59.00; H,6.47; N,17.87; C$_{19}$H$_{25}$N$_5$O$_4$ requires: C,58.90; H,6.50; N,18.08%.

$^1$H-NMR (CDCl$_3$): δ=7.55–7.50(d,1H), 7.45(s,1H), 6.85–6.80(d,1H), 5.85–5.75(d,1H), 4.70–4.60(t,1 H), 4.40 (d,1H), 4.35–4.25(m,2H), 4.05–3.90(m,2H), 3.70–3.65(m, 1H), 3.10–3.00(m,1H), 2.85–2.75(m,1H), 2.50–2.30(m,2H), 1.80–1.45(m,4H), 1.40(s,3H), 1.15(s,3H) ppm.

EXAMPLE 72

(3S,4R/3R,4S)-6-(1-[2-(4-Benzyloxyphenyl)ethyl]-1H-tetrazol-5-yl)-3,4-dihydro-2,2-dimethyl-3-hydroxy-4-(2-oxo-1,2-dihydropyridin-1-yl)-2H-benzo[b]pyran

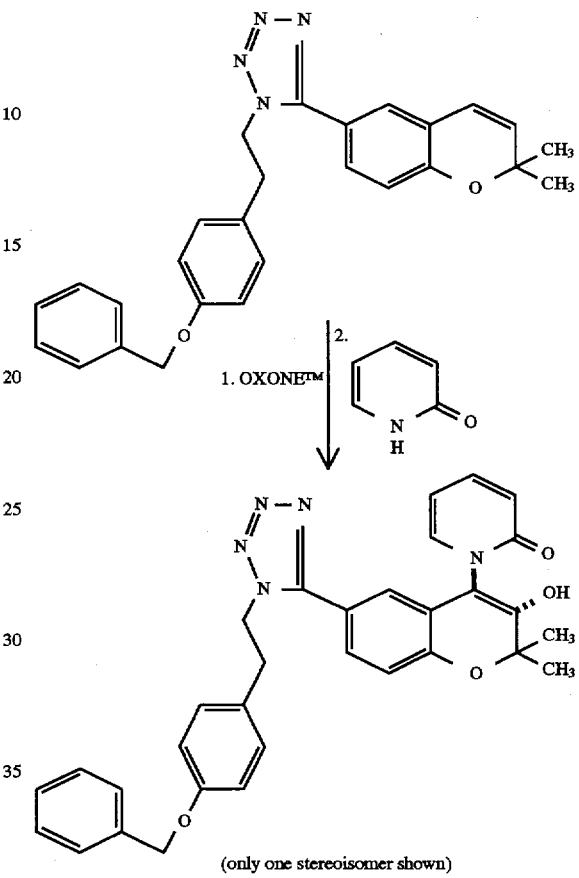

(only one stereoisomer shown)

A solution of OXONE (trade mark) (4.2 g) in water (20 ml) was added, over 1 hour, to a stirred mixture of 6-(1-[2-(4-benzyloxyphenyl)ethyl]-1H-tetrazol-5-yl)-2,2-dimethyl-2H-benzo[b]pyran (see Preparation 31) (3 g), sodium hydrogen carbonate (3.5 g), water (20 ml) and acetone (60 ml). When the addition was complete the mixture was stirred at room temperature for a further 1 hour. The acetone was evaporated in vacuo and the resulting aqueous mixture was extracted with dichloromethane (2×100 ml). The dichloromethane solution was dried (Na$_2$SO$_4$) then concentrated in vacuo to the give the crude epoxide intermediate as a foam, 3.2 g. The foam was dissolved in anhydrous dioxan (20 ml) then 2-hydroxypyridine (2 g) and benzyltrimethylammonium hydroxide (0.5 ml of a 40% solution in methanol) were added. The mixture was heated under reflux for 4 hours then allowed to stand at room temperature for 16 hours. Water (100 ml) was added and the mixture extracted with dichloromethane (3×50 ml). The combined dichloromethane extracts were washed with water (50 ml) and concentrated in vacuo to give a solid which was purified by column chromatography on silica eluting with dichloromethane containing methanol (2.5%). The product-containing fractions were combined and concentrated in vacuo to give the title compound as a foam, 2.5 g. Found: C,67.84; H,5.27; N,11.97; C$_{32}$H$_{31}$N$_6$O$_4$.H$_2$O requires: C,67.71; H,5.86; N,12.34%.

$^1$H-NMR (CDCl$_3$): δ=7.50–7.25(m,6H), 7.20–7.15(d, 1H), 7.00–6.75(m,6H), 6.70–6.65(d,1H), 6.35–6.30(d,1H), 6.20–6.15(t, 1H), 5.05(s,2H), 4.50–4.40(m,2H), 4.20(d,1H), 3.90–3.85(dd,1H), 3.20–3.00(m,2H), 1.55(s,3H), 1.40(s,3H) ppm.

EXAMPLE 73

(3S,4R/3R,4S)-6-(1-[2-Aminoethyl]-1H-tetrazol-5-yl)-3,4-dihydro-2,2-dimethyl-3-hydroxy-4-(2-oxopiperidin-1-yl)-2H-benzo[b]pyran

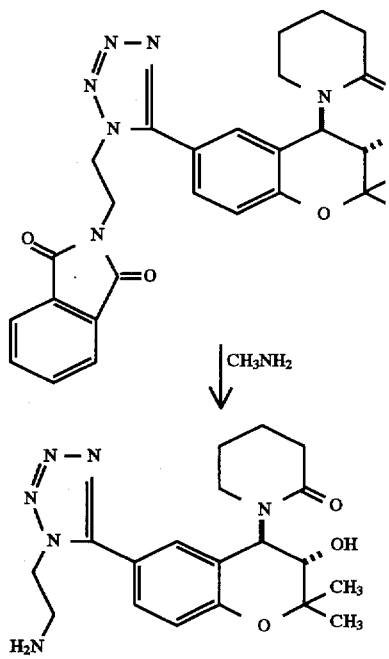

(only one stereoisomer shown)

A mixture of (3S,4R/3R,4S)-3,4-dihydro-2,2-dimethyl-3-hydroxy-4-(2-oxopiperidin-1-yl)-6-(1-[2-phthalimidoethyl]-1H-tetrazol-5-yl)-2H-benzo[b]pyran (see Example 52) (0.5 g) and methylamine (10 ml of a 33% solution in industrial methylated spirit) was stirred at room temperature for 24 hours. The solvent was evaporated in vacuo and the residue was azeotroped twice with dichloromethane to give a solid which was purified by chromatography on silica eluting with dichloromethane containing methanol (1.25%). The product-containing fractions were combined and concentrated in vacuo to give the title compound as a foam, 0.34 g.

$^1$H-NMR (CDCl$_3$): δ=7.60–7.55(d,1H), 7.50(s,1H), 7.00–6.95(d,1H), 6.00–5.90(d,1H), 4.45–4.35(m,2H), 3.90–3.80(d,1H), 3.35–3.25(m,2H), 3.15–3.05(m,1H), 3.05–2.90(m,1H), 2.60–2.50(m,2H), 1.90–1.60(m,5H), 1.55(s,3H), 1.30(s,3H) ppm.

EXAMPLE 74

(3S,4R)-3,4-Dihydro-6-(1-[4-ethoxycarbonylbut-1-yl]-1H-tetrazol-5-yl)-3-hydroxy-4-(2-methyl-3-oxopyridazin-6-yl)oxy-2,2,3-trimethyl-2H-benzo[b]pyran

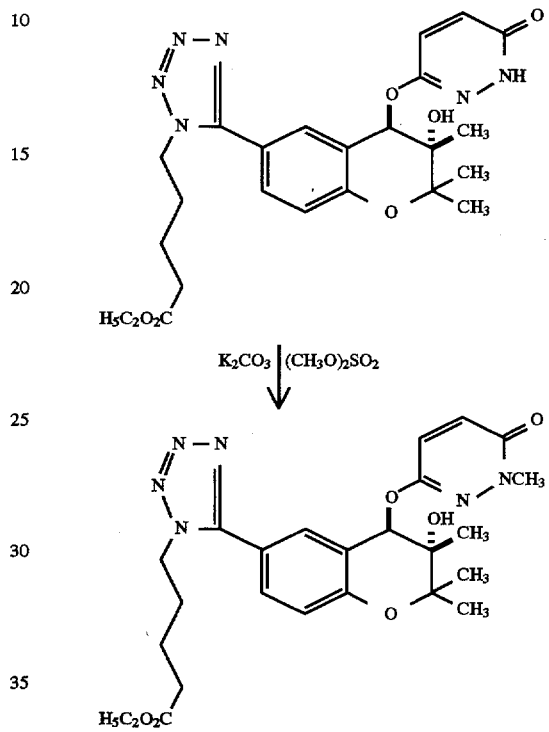

A mixture containing (3S,4R)-3,4-dihydro-6-(1-[4-ethoxycarbonylbut-1-yl]-1H-tetrazol-5-yl)-3-hydroxy-4-(3-hydroxypyridazin-6-yl)oxy-2,2,3-trimethyl-2H-benzo[b]pyran (see Example 11) (0.25 g), dimethyl sulfate (0.34 ml), anhydrous potassium carbonate (0.51 g) and acetone (10 ml) was heated under reflux for 4 hours. On cooling to room temperature the mixture was concentrated in vacuo and the residue partitioned between ethyl acetate (50 ml) and water (50 ml).

The ethyl acetate layer was washed with saturated aqueous sodium chloride (50 ml), dried (MgSO$_4$) and concentrated in vacuo to give an oil which was purified by chromatography on silica eluting with ethyl acetate. The product-containing fractions were combined and concentrated in vacuo to give the title compound as a gum, 0.015 g.

$^1$H-NMR (CDCl$_3$): δ=7.65(d,1H), 7.45–7.40(dd,1H), 7.10–6.90(m,3H), 5.95(s,1H), 4.40–4.30(t,2H), 4.10–4.00(q,2H), 3.80–3.70(brs,1H), 3.65(s,3H), 2.30–2.20(t,2H), 1.95–1.85(m,2H), 1.60–1.50(m,2H), 1.45(s,3H), 1.40(s,3H), 1.25(s,3H), 1.25–1.15(t,3H) ppm.

EXAMPLE 75

(3S,4R)-4-(3-Cyano-2-methylisothioureido)-3,4-dihydro-6-(1-[3-ethoxycarbonylprop-1-yl]-1H-tetrazol-5-yl)-3-hydroxy-2,2,3-trimethyl-2H-benzo[b]pyran

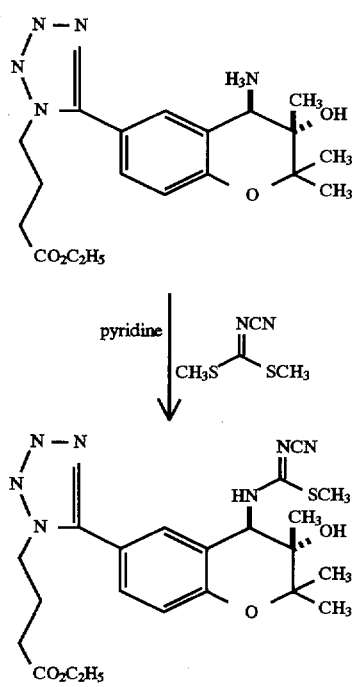

A mixture containing (3S,4R)-4-amino-3,4-dihydro-6-(1-[3-ethoxycarbonylprop-1-yl]-1H-tetrazol-5-yl)-3-hydroxy-2,2,3-trimethyl-2H-benzo[b]pyran (see Preparation 55) (1.2 g), dimethyl N-cyanodithioiminocarbonate (0.7 g) and pyridine (10 ml) was heated at 75° C. for 18 hours then concentrated in vacuo to give a gum which was stirred in dichloromethane containing methanol (2.5%) (20 ml). The resulting solid was filtered off and dried in vacuo to give the title compound, 0.85 g, m.p. 225°–227° C. Found: C,54.13; H,5.91; N,19.81; $C_{22}H_{29}N_7O_4S$ requires: C,54.20; H,6.00; N,20.11%.

$^1$H-NMR ($d_6$-DMSO): δ=8.45–8.30(brs,1H), 7.60–7.55 (d,1H), 7.40(s,1H), 7.00–6.90(d,1H), 5.50–5.40(brs,1H), 5.35(s,1H), 4.50–4.40(t,2H), 4.00–3.90(q,2H), 2.70–2.60 (brs,3H), 2.40–2.30(t,2H), 2.15–2.00(m,2H), 1.40(s, 3H), 1.30(s,3H), 1.10(s,3H), 1.15–1.05(t,3H) ppm.

EXAMPLE 76

(3S,4R)-4-(3-Cyano-2-ethylisoureido)-3,4-dihydro-6-(1-[3-ethoxycarbonylprop-1-yl]-1H-tetrazol-5-yl)-3-hydroxy-2,2,3-trimethyl-2H-benzo[b]pyran

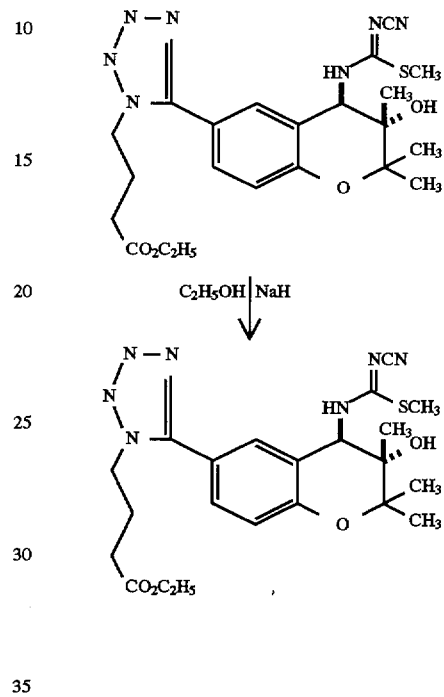

Sodium hydride (0.03 g of an 80% dispersion in mineral oil) was added to ethanol (4 ml). After 5 minutes (3S,4R)-4-(3-cyano-2-methylisothioureido)-3,4-dihydro-6-(1-[3-ethoxycarbonylprop-1-yl]-1H-tetrazol-5-yl)-3-hydroxy-2,2,3-trimethyl-2H-benzo[b]pyran (see Example 75) (0.2 g) was added and the mixture was allowed to stand at room temperature for 16 hours. The solution was acidified to pH 3 with 2N hydrochloric acid and then was concentrated in vacuo. The residue was purified by chromatography on silica eluting with dichloromethane containing methanol (2.5%). The product-containing fractions were combined and concentrated in vacuo to give an oil which was triturated with hexane to give the title compound as a foam, 0.09 g. Found: C,57.00; H,6.46; N,19.48; $C_{23}H_{31}N_7O_5$.0.1 hexane requires: C,57.35; H,6.60; N,19.83%.

$^1$H-NMR (CDCl$_3$): δ=7.55–7.45(m,2H), 7.05–6.95(d, 1H), 6.55–6.45(d,1H), 5.30–5.15(m,1H), 4.60–4.45(m,1H), 4.45–4.25(m,3H), 4.15–4.05(m,2H), 2.55–2.30(m,3H), 2.20–2.10(m,2H), 1.50(s,3H), 1.45(s,3H), 1.40–1.30(t,3H), 1.25(s,3H), 1.30–1.20(t,3H) ppm.

EXAMPLE 77

(3S,4R)-3,4-Dihydro-6-(1-[3-ethoxycarbonylprop-1-yl]-1H-tetrazol-5-yl)-3-hydroxy-4-(2-methylthiopyrimidin-4-yl)amino-2,2,3-trimethyl-2H-benzo[b]pyran

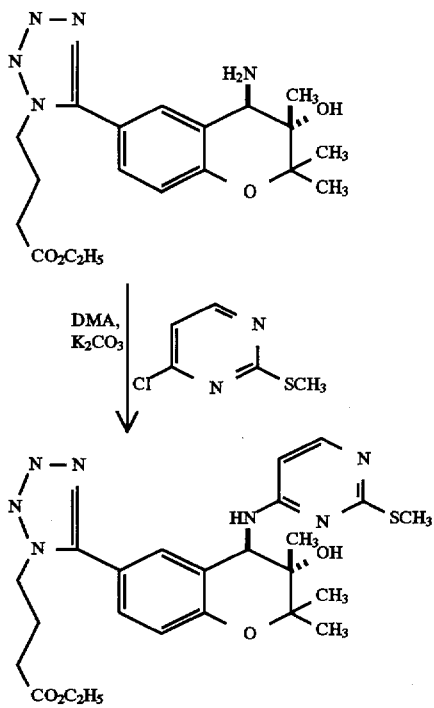

A mixture containing (3S,4R)-4-amino-3,4-dihydro-6-(1-[3-ethoxycarbonylprop-1-yl]-1H-tetrazol-5-yl)-3-hydroxy-2,2,3-trimethyl-2H-benzo[b]pyran (see Preparation 55) (0.6 g), 4-chloro-2-methylthiopyrimidine (0.5 g), anhydrous potassium carbonate (0.7 g) and anhydrous dimethylacetamide (5 ml) was heated at 120° C. for 24 hours. On cooling to room temperature water (10 ml) was added and the mixture was extracted with ethyl acetate (2×50 ml). The extracts were combined and washed with water (50 ml) then concentrated in vacuo to give an oil which was purified by chromatography on silica eluting with dichloromethane containing ethyl acetate (40%). The product-containing fractions were combined and concentrated in vacuo to give a foam which was further purified by chromatography on silica eluting with dichloromethane containing isopropanol (3.3%). The product-containing fractions were combined and concentrated in vacuo to give an oil which was triturated with hexane to give the title compound as a foam, 0.077 g, m.p. 115°–130° C.

$^1$H-NMR (CDCl$_3$): δ=7.95–7.90(d,1H), 7.65(s,1H), 7.55–7.45(dd,1H), 7.05–6.95(d,1H), 6.95–6.85(m,1H), 6.00–5.80(brm,1H), 4.65–4.40(m,2H), 4.15–4.05(m,2H), 2.55(s,3H), 2.50–2.40(m,2H), 2.30–2.10(m,2H), 1.60(s,3H), 1.55(s,3H), 1.30(s,3H), 1.30–1.20(t,3H) ppm.

EXAMPLE 78

(3S,4R)-4-(2-Chloropyrimidin-4-yl)amino- and (3S,4R)-4-(4-Chloropyrimidin-2-yl)amino-3,4-dihydro-6-(1-[3-ethoxycarbonylprop-1-yl]-1H-tetrazol-5-yl)-3-hydroxy-2,2,3-trimethyl-2H-benzo[b]pyran
(Examples 78A and 78B Respectively)

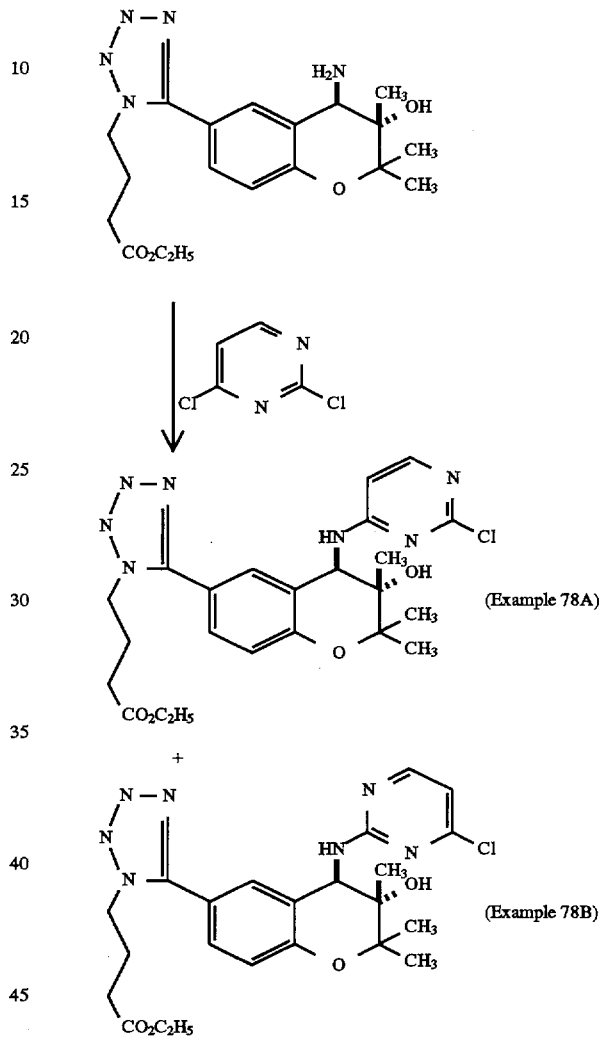

A mixture containing (3S,4R)-4-amino-3,4-dihydro-6-(1-[3-ethoxycarbonylprop-1-yl]-1H-tetrazol-5-yl)-3-hydroxy-2,2,3-trimethyl-2H-benzo[b]pyran (see Preparation 55) (0.5 g), 2,4-dichloropyrimidine (0.383 g), diisopropylethylamine (0.33 g) and dioxan (10 ml) was heated under reflux for 18 hours. The mixture was concentrated in vacuo and the residue purified by chromatography on silica eluting with dichloromethane containing ethyl acetate (40%). This first gave, after combination and evaporation of the appropriate fractions, an oil which was triturated with hexane to give the 4-chloropyrimidinyl title compound, Example 78B, as a foam, 0.12 g.

$^1$H-NMR (CDCl$_3$): δ=8.15–8.10(d,1H), 7.70(s,1H), 7.55–7.50(dd,1H), 7.05–7.00(d,1H), 6.70–6.65(d,1H), 6.30–6.25(d,1H), 5.50–5.45(d,1H), 4.60–4.45(m,2H), 4.20–4.00(m,2H), 2.50–2.40(m,2H), 2.25–2.10(m,2H), 1.55 (s,3H), 1.50(s,3H), 1.30–1.15(t,3H), 1.25(s,3H) ppm.

Further elution of the column with ethyl acetate containing dichloromethane (20%) gave, after combination and evaporation of the appropriate fractions, an oil which was triturated with diethyl ether to give the 2-chloropyrimidinyl title compound, Example 78A, as a foam, 0.34 g.

$^1$H-NMR (CDCl$_3$): δ=8.10–8.05(d,1H), 7.60(s,1H), 7.35–7.30(d,1H), 7.15–7.00(brs,1H), 6.95–6.85(m,2H), 5.65–5.50(brm,1H), 5.30–5.20(brs,1H), 4.55–4.25(m,2H), 4.10–3.90(m,2H), 2.45–2.30(m,2H), 2.15–2.05(m,2H), 1.55 (s,3H), 1.50(s,3H), 1.25(s,3H), 1.30–1.10(t,3H) ppm.

EXAMPLE 79

(3S,4R)-4-(2-Chloropyrimidin-4-yl)amino- and (3S, 4R)-4-(4-Chloropyrimidin-2-yl)amino-3,4-dihydro-6-(1-[4-ethoxycarbonylbut-1-yl]-1H-tetrazol-5-yl)-3-hydroxy-2,2,3-trimethyl-2H-benzo[b]pyran (Examples 79A and 79B Respectively)

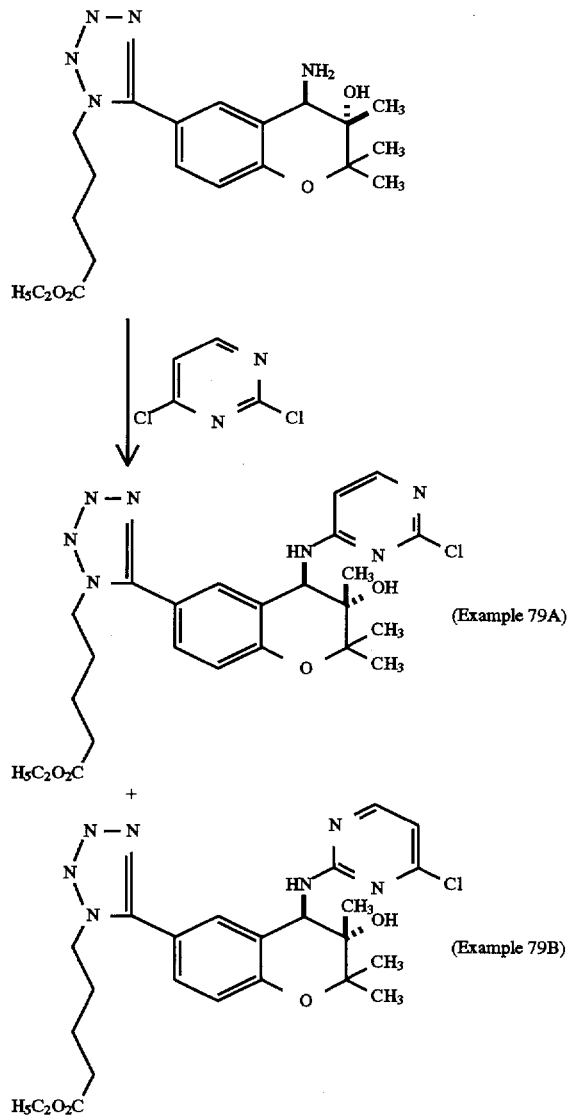

(Example 79A)

(Example 79B)

A mixture containing (3S,4R)-4-amino-3,4-dihydro-6-(1-[4-ethoxycarbonylbut-1-yl]-1H-tetrazol-5-yl)-3-hydroxy-2,2,3-trimethyl-2H-benzo[b]pyran (see Preparation 68) (0.36 g), 2,4-dichloropyrimidine (0.26 g), diisopropylethylamine (0.225 g) and dioxan (5 ml) was heated at 95° C. for 20 hours. On cooling to room temperature the mixture was poured into water (20 ml) and extracted with ethyl acetate (3×20 ml). The combined ethyl acetate extracts were washed with water (50 ml) then dried (MgSO$_4$) and concentrated in vacuo to give a gum which was purified by chromatography on silica eluting with 1:1 ethyl acetate/hexane. The fractions containing the higher Rf product were combined and concentrated in vacuo to give the 4-chloropyrimidinyl title compound, Example 79B, 0.076 g.

$^1$H-NMR (CDCl$_3$): δ=8.10(d,1H), 7.70(s,1H), 7.45–7.40 (dd,1H), 7.00–6.95(d,1H), 6.65–6.60(d,1H), 6.20–6.00(brs, 1H), 5.50–5.40(d,1H), 4.40–4.35(t,2H), 4.10–3.95(m,3H), 2.30–2.20(m,2H), 1.95–1.85(m,2H), 1.60–1.40(m,2H), 1.50 (s,3H), 1.45(s,3H), 1.25–1.15(m,6H) ppm.

The fractions containing the lower Rf product were combined and concentrated in vacuo to give the 2-chloropyrimidinyl title compound, Example 79A, 0.18 g.

$^1$H-NMR (CDCl$_3$): δ=8.05–8.00(d,1H), 7.55(s,1H), 7.30–7.25(d,1H), 7.10–7.00(brs,0.5H), 6.90(d,1H), 6.85(d, 1H), 5.65–5.50(brs,1H), 5.10–4.95(brs,0.5H), 4.45–4.25(m, 2H), 4.15–4.00(m,3H), 2.25–2.10(m,2H), 1.95–1.75(m,2H), 1.60–1.20(brm,2H), 1.50(s,3H), 1.45(s,3H), 1.25–1.15(m, 6H) ppm.

The following Preparations illustrate the preparation of certain starting materials used in the preceding Examples:

PREPARATION 1

(3S,4S)-3,4-Dihydro-3,4-epoxy-6-(1-[3-ethoxycarbonylprop-1]-1H-tetrazol-5-yl)-2,2,3-trimethyl-2H-benzo[b]pyran

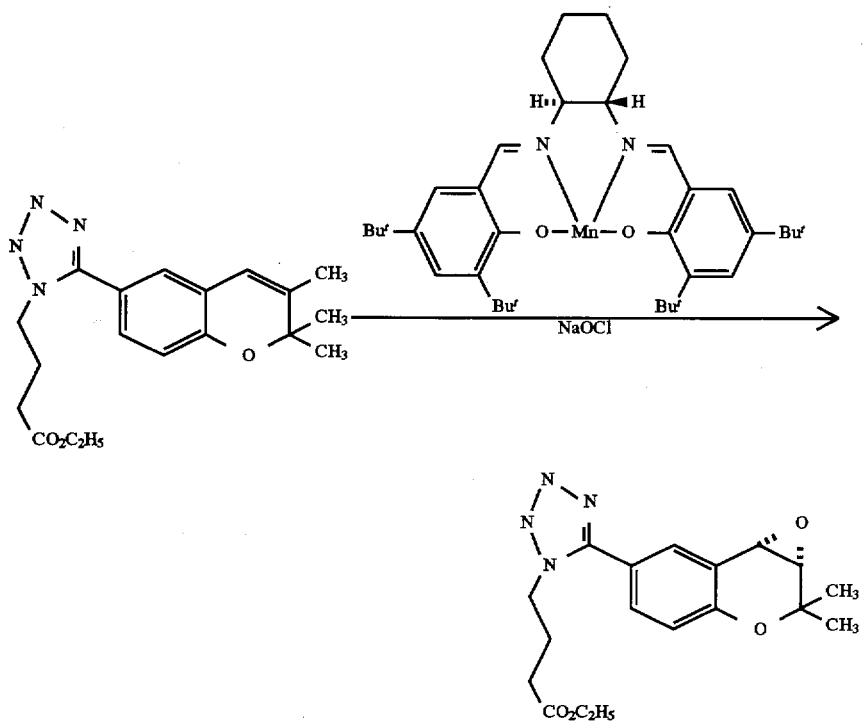

A solution of the compound of Preparation 2 (2 g) and [(S,S)-1,2-bis(3,5-di-tert-butylsalicylideamino]cyclohexane manganese III chloride (see J. Amer. Chem. Soc., 1991, 113, 7063) (0.23 g) in dichloromethane (7 ml) was added to a stirred solution of commercial bleach (21 ml of a 3M solution) at 0° C. The mixture was stirred at 0° C. for 7 hours then diluted with dichloromethane (20 ml). The layers were separated and the dichloromethane solution was washed with water (20 ml) then dried (MgSO$_4$) and concentrated in vacuo. The residue was purified by chromatography on silica eluting with dichloromethane containing methanol (2.5%). The product-containing fractions were combined and concentrated in vacuo, to give the title compound as a red/brown oil, 0.99 g, optical purity 97% by chiral HPLC.

$^1$H-NMR (CDCl$_3$): δ=7.75 (s,1H), 7.60–7.55 (dd,1H), 7.00–6.95 (d,1H), 4.55–4.45 (t,2H), 4.15–4.05 (q,2H), 3.95 (s,1H), 2.45–2.35 (m,2H), 2.30–2.20 (m,2H), 1.60 (s,3H), 1.55 (s,3H), 1.30 (s,3H), 1.30–1.20 (t,3H) ppm.

PREPARATION 2

6-(1-[3-Ethoxycarbonylprop-1-yl]-1H-tetrazol-5-yl)-2,2,3-trimethyl-2H-benzo[b]pyran

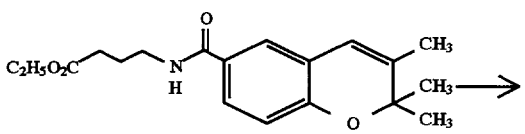

-continued

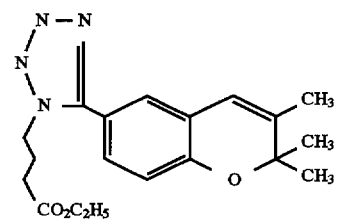

Phosphorus pentachloride (1.8 g) was added to a solution of the compound of Preparation 3 (2.4 g) in chloroform (30ml) and the mixture was heated under reflux for 15 minutes. On cooling to room temperature trimethylsilyl azide (1.4 g) was added and the mixture was stirred at room temperature for 16 hours. Water (20 ml) was added and the mixture was stirred vigorously. The layers were separated and the chloroform solution was concentrated in vacuo to give an orange oil which was purified by chromatography on silica eluting with dichloromethane containing ethyl acetate (5%). The product-containing fractions were combined and concentrated in vacuo to give the title compound as a pale yellow oil, 2.04 g.

$^1$H-NMR (CDCl$_3$): δ=7.40–7.35 (dd,1H), 7.30 (d,1H), 6.90–6.85 (d,1H), 6.15–6.10 (d,1H), 4.55–4.45 (m,2H), 4.15–4.05 (m,2H), 2.45–2.30 (m,2H), 2.30–2.20 (m,2H), 1.85 (s,3H), 1.45 (s,6H), 1.25–1.20 (t,3H) ppm.

PREPARATION 3

6-(N-[3-Ethoxycarbonyl]prop-1-yl)carbamoyl-2,2,3-trimethyl-2H-benzo[b]pyran

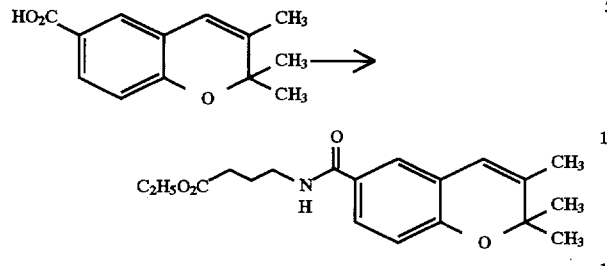

A mixture of the compound of Preparation 4 (2 g) and 1,1'-carbonyldiimidazole (1.6 g) was stirred in dichloromethane (50 ml) for 30 minutes. Triethylamine (1.4 g) and ethyl 4-aminobutanoate hydrochloride (2.3 g) were added and the mixture was stirred at room temperature for 5 days then washed with water (100 ml) and concentrated in vacuo. The residue was purified by chromatography on silica eluting with dichloromethane containing methanol (1.25%). The product-containing fractions were combined and concentrated in vacuo to give the title compound as a yellow oil, 2.4 g.

$^1$H-NMR (CDCl$_3$): δ7.50–7.45 (dd,1H), 7.35 (d,1H), 6.80–6.75 (d,1H), 6.45–6.35 (m,1H), 6.10 (s,1H), 4.15–4.05 (q,2H), 3.50–3.40 (q,2H), 2.45–2.35 (t,2H), 2.00–1.90 (m,2H), 1.85 (s,3H), 1.40 (s,6H), 1.25–1.20 (t,3H) ppm.

PREPARATION 4

2,2,3-Trimethyl-2H-benzo[b]pyran-6-carboxylic Acid

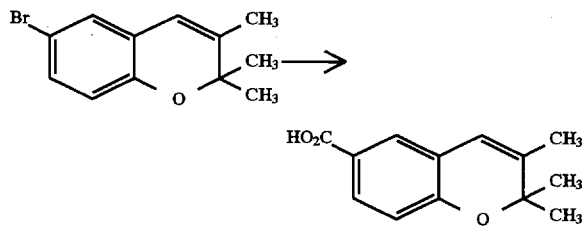

n-Butyllithium (81 ml of a 2.5M solution in hexane) was added dropwise to a solution of the compound of Preparation 5 (47 g) in anhydrous tetrahydrofuran (250 ml) at –70° C. When the addition was complete the mixture was stirred at –70° C. for 15 minutes then carbon dioxide pellets were added at such a rate that the temperature of the reaction mixture did not exceed –60° C. When the addition of pellets was no longer exothermic the mixture was allowed to warm to room temperature. Water (50 ml) was added and the tetrahydrofuran evaporated in vacuo. Further water (500 ml) was added and the solution was brought to pH 14 by the addition of 10% aqueous sodium hydroxide solution. The aqueous mixture was extracted with diethyl ether then acidified to pH 1 by the addition of concentrated hydrochloric acid. The resulting solid was filtered off, washed with water, dissolved in dichloromethane (500 ml), the organic layer was separated from the residual water, dried (Na$_2$SO$_4$) and concentrated in vacuo. The resulting solid was triturated with hexane to give the title compound as a colourless solid, 31 g, m.p. 169°–171° C. Found: C, 71.22; H, 6.72; C$_{13}$H$_{14}$O$_3$ requires: C, 71.55; H, 6.47%.

$^1$H-NMR (CDCl$_3$): δ=7.90–7.80 (d,1H), 7.65 (s,1H), 6.85–6.75 (d,1H), 6.10 (s,1H), 1.85 (s,3H), 1.45 (s,6H) ppm.

PREPARATION 5

6-Bromo-2,2,3-trimethyl-2H-benzo[b]pyran

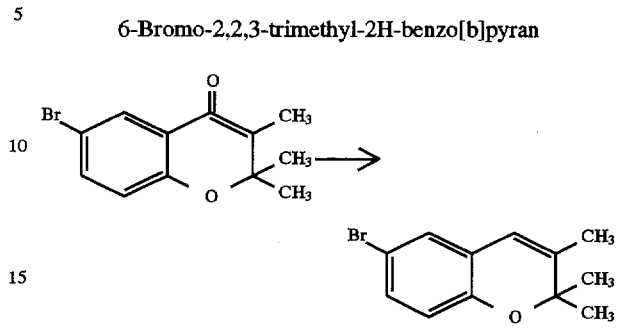

Sodium borohydride (24 g) was added in portions to a solution of the compound of Preparation 6 (or Preparation 78) (164 g) in ethanol (700 ml) and the resulting mixture was stirred at room temperature for 1.5 hours then concentrated in vacuo. Water (500 ml) was added and the mixture was cooled to 0° C. then acidified to pH 1 with concentrated hydrochloric acid. The mixture was extracted with diethyl ether (2×500 ml) and the combined ether extracts were washed with water (500 ml), dried (MgSO$_4$) and concentrated in vacuo to give a red oil. The oil was dissolved in toluene (2 liters), para-toluenesulphonic acid (22 g) was added and the mixture was heated under reflux using Dean-Stark apparatus for 30 minutes. Further para-toluenesulphonic acid (5 g) was added and heating was continued for 1 hour. On cooling to room temperature, the mixture was washed with 10% aqueous sodium hydroxide (500 ml) and water (500 ml) then concentrated in vacuo. The residue was purified by chromatography on silica eluting with hexane containing dichloromethane (20%).The product-containing fractions were combined and concentrated in vacuo to give the title compound as a red oil, 130 g.

$^1$H-NMR (CDCl$_3$): δ=7.15–7.10 (dd,1H), 7.00 (s, 1H), 6.65–6.60 (d,1H), 6.00 (s,1H), 1.85 (s,3H), 1.60 (s,6H) ppm.

PREPARATION 6

6-Bromo-2,3-dihydro-2,2,3-trimethyl-4H-benzo[b]pyran-4-one

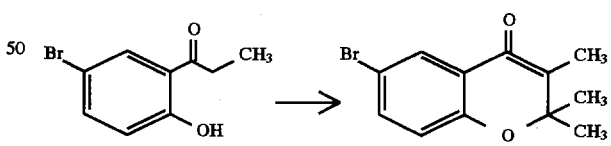

A mixture of the compound of Preparation 7 (255 g), pyrrolidine (109 ml) and toluene (800 ml) was heated under reflux in a Dean-Stark apparatus for 22 hours. Acetone (125 ml) was added and heating was continued for 24 hours. Further portions of acetone (125 ml) were added after 24 and 48 hours and heating was continued for a total of 6 days. The mixture was concentrated in vacuo and the residue was taken up in diethyl ether (1250 ml). The ethereal solution was washed with 2N hydrochloric acid (800 ml), 2N sodium hydroxide (3×300 ml) and brine (2×400 ml) then dried (MgSO$_4$) and concentrated in vacuo to give the title compound as a dark oil, 164.5 g.

¹H-NMR (CDCl₃): δ=7.95 (d,1H), 7.55–7.50 (dd,1H), 6.85–6.80 (d,1H), 2.75–2.65 (q,1H), 1.45 (s,3H), 1.25 (s,3H), 1.20–1.15 (d,3H) ppm.

PREPARATION 7

4-Bromo-2-propanoylphenol

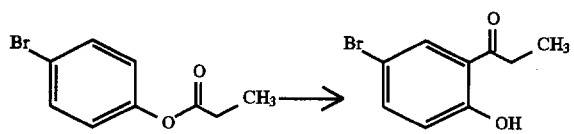

A mixture of the compound of Preparation 8 (230 g) and aluminium chloride (300 g) was heated with stirring until the reaction temperature was approximately 80° C., whereupon an exothermic reaction took place which raised the temperature of the mixture to 110° C. The reaction mixture was stirred at 110° C. for 20 minutes then the temperature was increased to 140° C. for 20 minutes and, finally, the mixture was heated at 160° C. for 1 hour. On cooling to room temperature the mixture was treated with ice (1 kg), and extracted with dichloromethane (3×500 ml). The dichloromethane extracts were dried (MgSO₄) and concentrated in vacuo to give the title compound as a dark oil which crystallised on standing, 223 g.

¹H-NMR (CDCl₃): δ=7.85 (d,1H), 7.55–7.50 (dd,1H), 6.90–6.85 (d,1H), 3.10–2.95 (q,2H), 1.25–1.20 (t,3H) ppm.

PREPARATION 8

4-Bromophenyl Propanoate

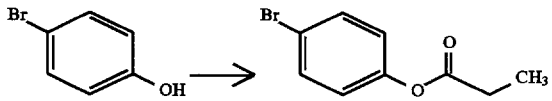

Triethylamine (219 ml) was added to a solution of 4-bromophenol (259 g) and 4-dimethylaminopyridine (1.5 g) in dichloromethane (1000 ml) at 0° C. at such a rate that the temperature did not rise above 20° C. When the addition was complete propionyl chloride (137 ml) was added in portions over 1 hour such that the temperature did not rise above 20° C. Finally, the mixture was stirred at room temperature for 2 hours. Water (700 ml) was added and the layers were separated. The dichloromethane solution was washed with brine (500 ml), dried (MgSO₄) and concentrated in vacuo to give the title compound as an oil, 344 g.

¹H-NMR (CDCl₃): δ=7.45–7.40 (d,2H), 6.95–6.90 (d,2H), 2.60–2.45 (q,2H), 1.25–1.15 (t,3H) ppm.

PREPARATION 9

(3S,4S)-3,4-Dihydro-3,4-epoxy-6-(1-methyl-1H-tetrazol-5-yl)-2,2,3-trimethyl-2H-benzo[b]pyran

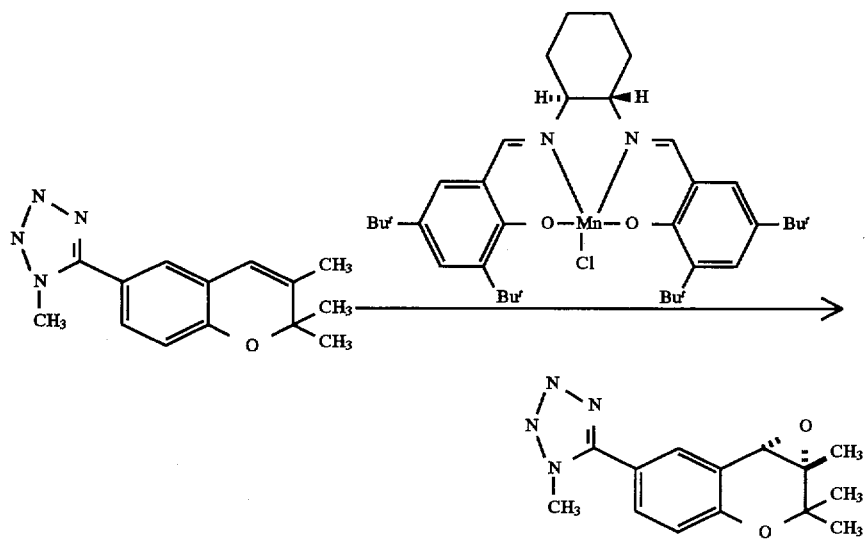

A solution of the compound of Preparation 10 (2.5 g) and [(S,S)-1,2-bis(3,5-di-tert-butylsalicylideamino]cyclohexane manganese III chloride (see J. Amer. Chem. Soc., 1991, 113, 7063) (0.4 g) in dichloromethane (15 ml) was added to a stirred solution of commercial bleach (36 ml of a 0.55M solution) at 0° C. The mixture was allowed to warm to room temperature and was stirred for 20 hours then extracted with dichloromethane (3×25 ml). The combined dichloromethane extracts were concentrated in vacuo to give an oil which was purified by chromatography on silica eluting with dichloromethane containing ethyl acetate (5% up to 10%). The product-containing fractions were combined and concentrated in vacuo to give a foam which was further purified by chromatography on silica eluting with dichloromethane containing methanol (2.5%). The product-containing fractions were combined and concentrated in vacuo to give the title compound as a foam, 1.0 g.

¹H-NMR (CDCl₃): δ=7.75 (d,1H), 7.60–7.55 (dd,1H), 7.00–6.95 (d,1H), 4.15 (s,3H), 3.75 (s,1H), 1.65 (s,3H), 1.55 (s,3H), 1.30 (s,3H) ppm.

PREPARATION 10

6-(1-Methyl-1H-tetrazol-5-yl)-2,2,3-trimethyl-2H-benzo[b]pyran

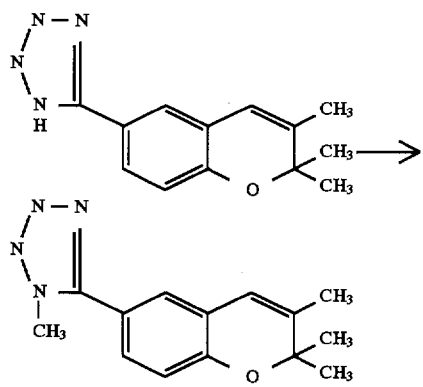

A mixture of the compound of Preparation 11 (4 g), bis(tributyltin) oxide (9.8 g) and iodomethane (4 ml) was stirred at room temperature for 16 hours. The iodomethane was evaporated in vacuo and the residue was triturated with hexane containing ethyl acetate (20%). The resulting solid was filtered off and dried to give the title compound, 2.9 g, m.p. 127°–130° C.

$^1$H-NMR (CDCl$_3$): δ=7.45–7.35 (dd,1H), 7.30 (d,1H), 6.90–6.85 (d,1H), 6.15 (s,1H), 4.15 (s,3H), 1.85 (s,3H), 1.45 (s,6H) ppm.

PREPARATION 11

6-(1H-Tetrazol-5-yl)-2,2,3-trimethyl-2H-benzo[b]pyran

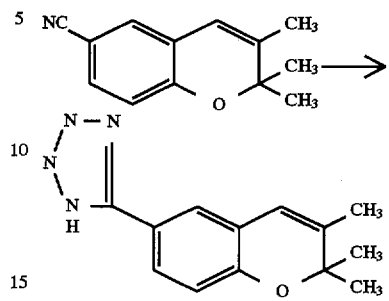

A mixture of 6-cyano-2,2,3-trimethyl-2H-benzo[b]pyran (see J. Med. Chem., 1991, 34, 3074) (4 g), sodium azide (4.0 g), triethylamine hydrochloride (4.2 g) and 1-methyl-2-pyrrolidinone (40 ml), was heated at 150° C. for 1 hour. On cooling to room temperature water (200 ml) was added and the mixture was brought to pH 14 by the addition of solid sodium hydroxide. The solution was extracted with ethyl acetate (200 ml) then acidified to pH 3–4 with concentrated hydrochloric acid to give a solid which was filtered off, washed with water and dried to give the title compound, 4.5 g, m.p. 179°–181° C. Found: C, 64.58; H, 5.81; N, 23.46; C$_{13}$H$_{14}$N$_4$O requires: C, 64.45; H, 5.82; N, 23.13%.

$^1$H-NMR (CDCl$_3$): δ=7.70–7.65 (dd,1H), 7.60 (d,1H), 6.80–6.75 (d,1H), 6.05 (s,1H), 1.80 (s,3H), 1.35 (s,6H) ppm.

PREPARATION 12

(3S,4S)-3,4-Dihydro-3,4-epoxy-6-(1-ethoxycarbonylmethyl-1H-tetrazol-5-yl)-2,2,3-trimethyl-2H-benzo[b]pyran

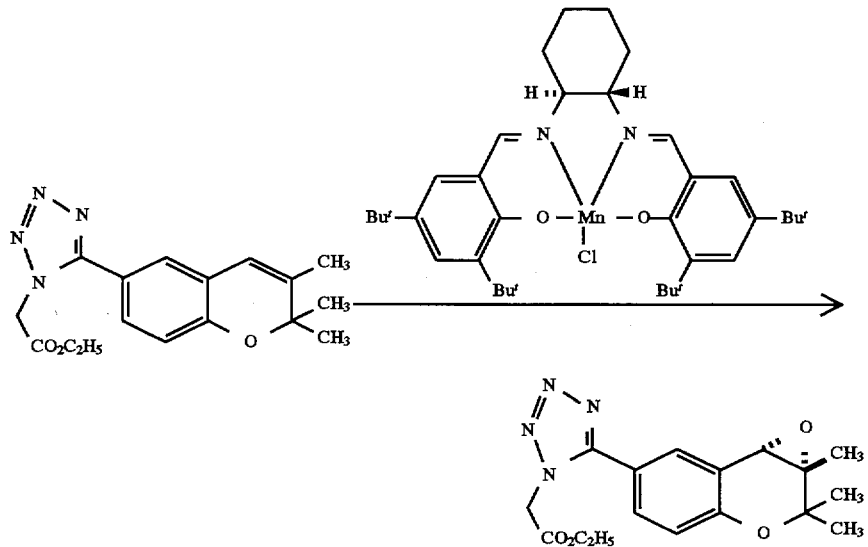

A solution of the compound of Preparation 13 (1.77 g) and [(S,S)-1,2-bis(3,5-di-tert-butylsalicylideamino]cyclohexane manganese III chloride (see J. Amer. Chem. Soc., 1991, 113, 7063) (0.23 g) in dichloromethane (7 ml) was added to a stirred solution of commercial bleach (21 ml of a 3M solution) at 0° C. The mixture was allowed to warm to room temperature and stirred for 16 hours. Dichloromethane (50 ml) was added and the mixture was filtered through a cellulose-based filter aid. The layers were separated and the dichloromethane solution was concentrated in vacuo to give a dark oil which was purified by chromatography on silica eluting with dichloromethane containing methanol (1.25%). The product-containing fractions were combined and concentrated in vacuo to give the title compound as a tan foam, 1.03 g.

¹H-NMR (CDCl₃): δ=7.65 (d,1H), 7.50-7.45 (dd,1H), 6.95-6.90 (d,1H), 5.15 (s,2H), 4.30-4.20 (q,2H), 3.70(s, 1H), 1.60 (s,3H), 1.55 (s,3H), 1.30 (s,3H), 1.30-1.25 (t,3H) ppm.

PREPARATION 13

6-(1-Ethoxycarbonylmethyl-1H-tetrazol-5-yl)-2,2,3-trimethyl-2H-benzo[b]pyran

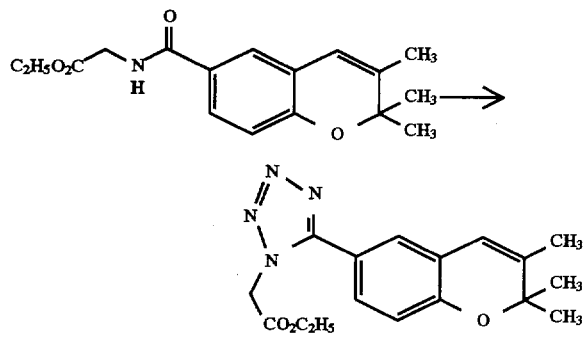

Phosphorus pentachloride (1.7 g) was added to a solution of the compound of Preparation 14 (2.34 g) in chloroform (30 ml) and the mixture was heated under reflux for 15 minutes. On cooling to room temperature trimethylsilyl azide (1.33 g) was added and the mixture was stirred at room temperature for 16 hours. Water (20 ml) was added and the mixture was stirred vigorously for 15 minutes. The layers were separated and the chloroform solution, was concentrated in vacuo to give an orange oil which was purified by chromatography on silica eluting with dichloromethane containing ethyl acetate (5%). The product-containing fractions were combined and concentrated in vacuo to give the title compound as an oil, 1.77 g.

¹H-NMR (CDCl₃): δ=7.30-7.20(m,2H), 6.90-6.85(d, 1H), 6.10(s,1H), 5.15(s,2H), 4.30-4.20(quartet,2H), 1.90(s, 3H), 1.45(s,6H), 1.30-1.20(t,3H) ppm.

PREPARATION 14

6-(N-Ethoxycarbonylmethyl)carbamoyl-2,2,3-trimethyl-2H-benzo[b]pyran

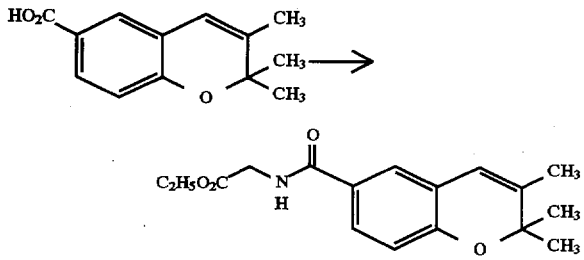

A mixture of the compound of Preparation 4 (2 g) and 1,1'-carbonyldiimidazole (1.6 g) in dichloromethane (50 ml) was stirred at room temperature for 30 minutes. Triethylamine (1.1 g) and ethyl glycinate hydrochloride (1.4 g) were added and the mixture was stirred at room temperature for 16 hours then washed with water (100 ml) and concentrated in vacuo. The residual red oil was purified by chromatography on silica eluting with dichloromethane containing methanol (1.25%). The product-containing fractions were combined and concentrated in vacuo to give the title compound as an oil, 2.34 g.

¹H-NMR (CDCl₃): δ=7.55-7.50 (dd,1H), 7.40 (d,1H), 6.80-6.75 (d,1H), 6.55-6.50 (brs,1H), 6.10 (s,1H), 4.30-4.15 (m,4H), 1.85 (d,3H), 1.40 (s,6H), 1.35-1.30 (t,3H) ppm.

PREPARATION 15

(3R,4R/3S,4S)-6-(1-[2-(4-Benzyloxyphenyl)ethyl]-1H-tetrazol-5-yl)-3,4-dihydro-3,4-epoxy-2,2,3-trimethyl-2H-benzo[b]pyran

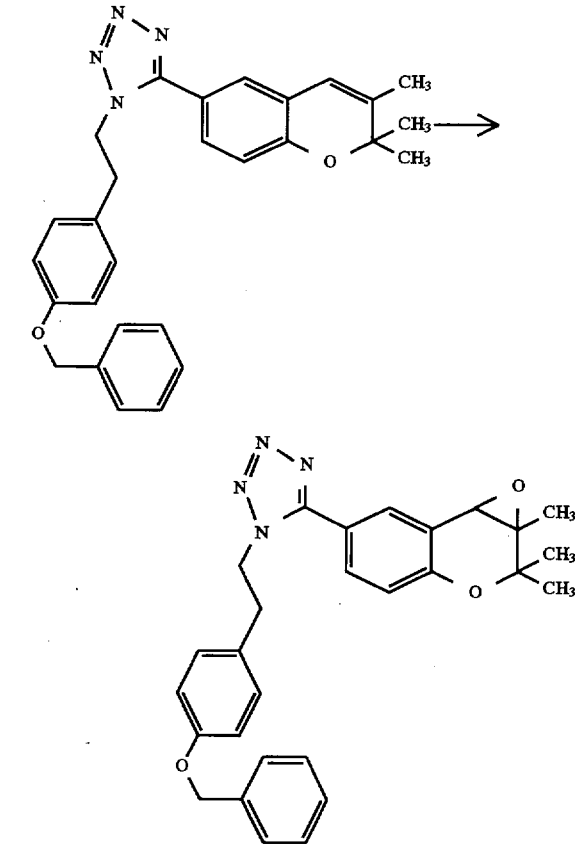

A solution of OXONE™ (3.7 g) in water (17 ml) was added, over 2 hours, to a stirred mixture of the compound of Preparation 16 (2.7 g), sodium hydrogen carbonate (3 g), water (17 ml) and acetone (52 ml). When the addition was complete the mixture was stirred at room temperature for a further 1.5 hours. The acetone was evaporated in vacuo and the resulting aqueous mixture was partitioned between water (50 ml) and dichloromethane (100 ml). The layers were separated and the dichloromethane layer was dried (Na₂SO₄), filtered through a cellulose-based filter aid and concentrated in vacuo to give the title compound as a yellow foam, 2.2 g.

¹H-NMR (CDCl₃): δ=7.50-7.30 (m,6H), 7.15-7.05 (m,2H), 6.85-6.80 (m,4H), 5.10-4.95 (m,2H), 4.60-4.45

(m,2H), 3.40 (s,1H), 3.20–3.15 (t,2H), 1.55 (s,3H), 1.50 (s,3H), 1.25 (s,3H) ppm.

PREPARATION 16

6-(1-[2-(4-Benzyloxyphenyl)ethyl]-1H-tetrazol-5-yl)-2,2,3-trimethyl-2H-benzo[b]pyran

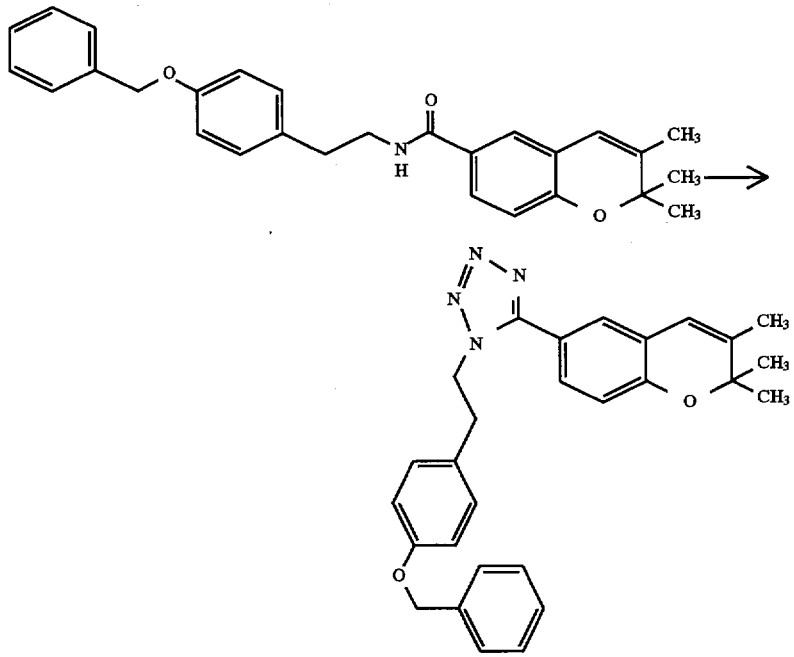

Phosphorus pentachloride (1.2 g) was added to a solution of the compound of Preparation 17 in chloroform (30 ml) and the mixture was heated under reflux for 15 minutes. On cooling to room temperature trimethylsilyl azide (1 g) was added and the mixture was stirred at room temperature for 16 hours. Water (20 ml) was added and the mixture was stirred vigorously for 15 minutes. The layers were separated and the chloroform solution was dried (MgSO$_4$) then concentrated in vacuo to give the title compound as an orange oil, 2.7 g.

$^1$H-NMR (CDCl$_3$): δ=7.45–7.25 (m,6H), 7.00–6.95 (dd, 1H), 6.90–6.75 (m,5H), 6.05 (s,1H), 5.00 (s,2H), 4.60–4.50 (t,2H), 3.25–3.15 (t,2H), 1.85 (s,3H), 1.45 (s,6H) ppm.

PREPARATION 17

6-(N-[2-(4-Benzyloxyphenyl)ethyl]carbamoyl)-2,2,3-trimethyl-2H-benzo[b]pyran

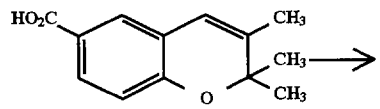

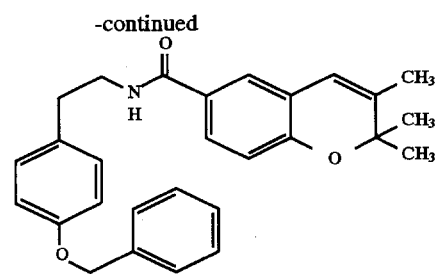

A mixture of the compound of Preparation 4 (1.5 g) and 1,1'-carbonyldiimidazole (1.17 g) in dichloromethane (40 ml) was stirred at room temperature for 30 minutes. 2-(4-Benzyloxyphenyl)ethylamine (2.2 g) was added and the mixture was stirred at room temperature for 3 days then diluted with dichloromethane (100 ml) and washed successively with 10% aqueous sodium hydroxide (100 ml) and 2N hydrochloric acid (2×100 ml). The dichloromethane layer was concentrated in vacuo and the residue was purified by chromatography on silica eluting with dichloromethane containing methanol (1%). The product-containing fractions were combined and concentrated in vacuo to give a foam which was azeotroped with dichloromethane to give the title compound as a pale yellow solid, 2.2 g.

$^1$H-NMR (CDCl$_3$): δ=7.50–7.30 (m,7H), 7.20–7.10 (d,2H), 6.95–6.90 (d,2H), 6.75–6.70 (d,1H), 6.10 (s,1H), 6.10–6.00 (t, 1H), 5.05 (s,2H), 3.70–3.60 (m,2H), 2.90–2.80 (t,2H), 1.85 (s,3H), 1.45 (s,6H) ppm.

PREPARATION 18

(3S,4S)-6-(1-Benzyl-1H-tetrazol-5-yl)-3,4-dihydro-3,4-epoxy-2,2,3-trimethyl-2H-benzo[b]pyran

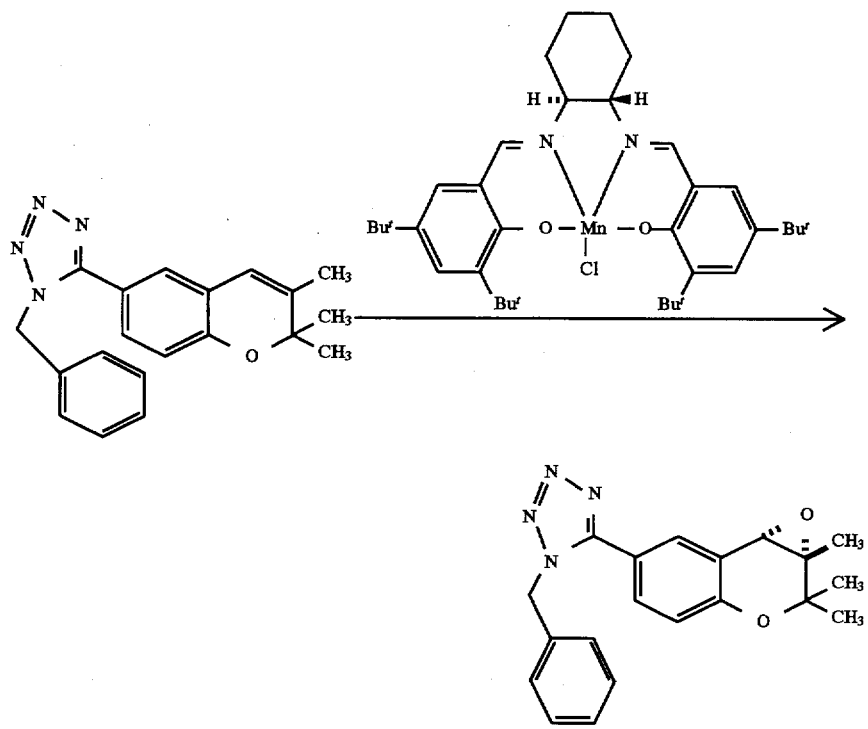

A solution of the compound of Preparation 19 (1.9 g) and [(S,S)-1,2-bis(3,5-di-tert-butylsalicylideamino]cyclohexane manganese III chloride (see J. Amer. Chem. Soc., 1991, 113, 7063) (0.23 g) in dichloromethane (7 ml) was added to a stirred solution of commercial bleach (21 ml of a 3M solution) at 0° C. The mixture was allowed to warm to room temperature and stirred for 16 hours then extracted with dichloromethane (2×20 ml). The dichloromethane extracts were concentrated in vacuo and the residue was purified by chromatography on silica eluting with dichloromethane containing methanol (1%). The product-containing fractions were combined and concentrated in vacuo to give the title compound as a foam, 1.03 g.

$^1$H-NMR (CDCl$_3$): δ=7.55 (d,1H), 7.45–7.40 (dd,1H), 7.40–7.30 (m,3H), 7.20–7.15 (m,2H), 6.90–6.85 (d,1H), 5.65 (s,2H), 3.65 (s,1H), 1.60 (s,3H), 1.55 (s,3H), 1.30 (s,3H) ppm.

PREPARATION 19

6-(1-Benzyl-1H-tetrazol-5-yl)-2,2,3-trimethyl-2H-benzo[b]pyran

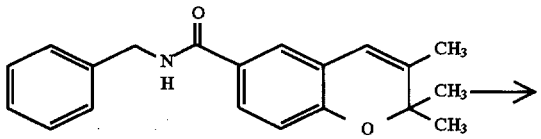

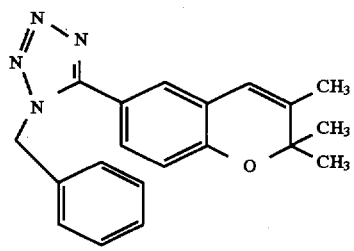

Phosphorus pentachloride (1.1 g) was added to a solution of the compound of Preparation 20 (1.6 g) in chloroform (25 ml) and the mixture heated under reflux for 15 minutes. On cooling to room temperature trimethylsilyl azide (0.9 g) was added and the mixture was allowed to stand at room temperature for 16 hours then diluted with chloroform (25 ml) and washed with water (30 ml). The chloroform solution was dried (MgSO$_4$) and concentrated in vacuo to give the title compound as an oil, 1.9 g.

$^1$H-NMR (CDCl$_3$): δ=7.40–7.30 (m,3H), 7.25–7.20 (dd, 1H), 7.20–7.15 (m,3H), 6.85–6.80 (d,1H), 6.05 (s,1H), 5.60 (s,2H), 1.85 (s,3H), 1.45 (s,6H) ppm.

PREPARATION 20

6-(N-Benzyl)carbamoyl-2,2,3-trimethyl-2H-benzo[b]pyran

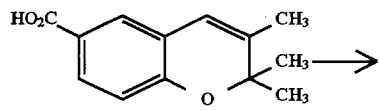

eluting with dichloromethane containing methanol (1%). The product-containing fractions were combined and concentrated in vacuo to give the title compound as a foam, 1.64 g.

$^1$H-NMR (CDCl$_3$): δ=7.50–7.45 (dd,1H), 7.40 (s,1H), 7.35–7.25 (m,5H), 6.80–6.75 (d,1H), 6.35–6.25 (brt, 1H), 6.10 (s,1H), 4.65–4.60 (d,2H), 1.85 (s,3H), 1.45 (s,6H) ppm.

PREPARATION 21

(3S,4S)-3,4-Dihydro-3,4-epoxy-6-(1-[2-phenylethyl]-1H-tetrazol-5-yl)-2,2,3-trimethyl-2H-benzo[b]pyran

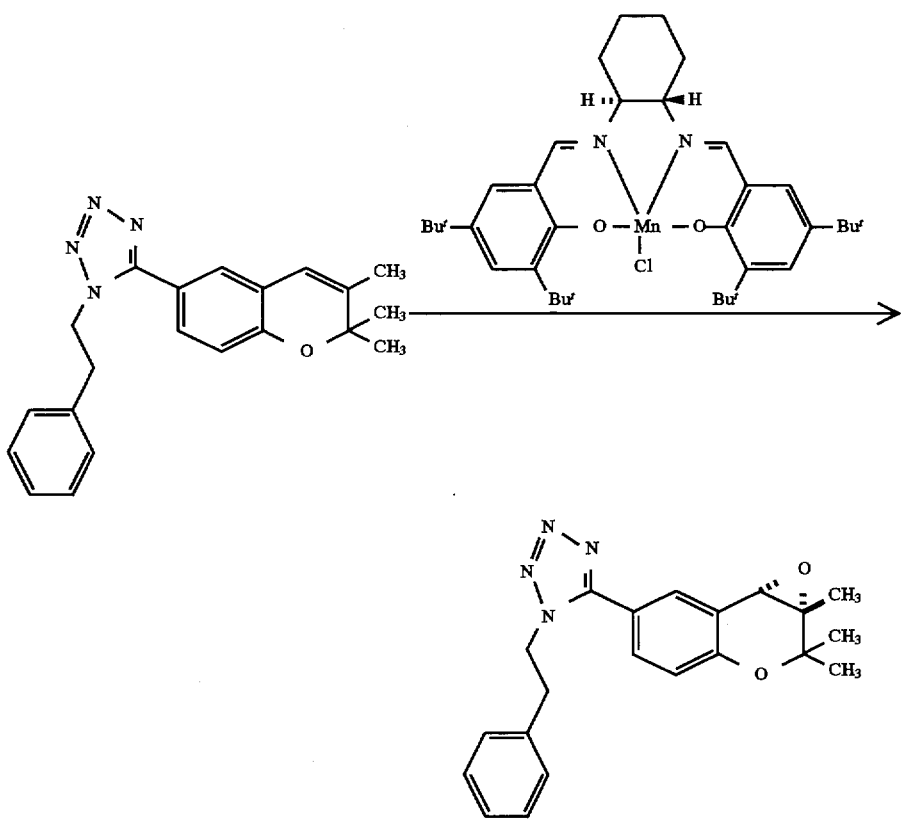

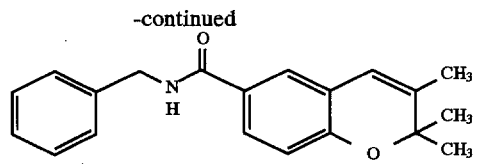

1,1'-Carbonyldiimidazole (1.17 g) was added to a solution of the compound of Preparation 4 (1.5 g) in dichloromethane (30 ml) and the mixture was stirred at room temperature for 30 minutes. Benzylamine (1.47 g) was added and the mixture was allowed to stand at room temperature for 16 hours then diluted with dichloromethane to a total volume of 70 ml. The solution was washed sequentially with 10% aqueous sodium hydroxide (50 ml), 2N hydrochloric acid (2×50 ml) and water (50 ml), then concentrated in vacuo to give a solid which was purified by chromatography on silica A solution of the compound of Preparation 22 (2 g) and [(S,S)-1,2-bis(3,5-di-tert-butylsalicylideamino]cyclohexane manganese III chloride (see J. Amer. Chem. Soc., 1991, 113, 7063) (0.23 g) in dichloromethane (7 ml) was added to a stirred solution of commercial bleach (21 ml of a 3M solution) at 0° C. The mixture was allowed to warm to room temperature and stirred for 16 hours then diluted with dichloromethane (20 ml) and filtered through a cellulose-based filter aid. The filtrate was concentrated in vacuo and the residue was purified by chromatography on silica eluting with dichloromethane containing methanol (1%). The product-containing fractions were combined and concentrated in vacuo to give the title compound as a foam, 1.14 g.

$^1$H-NMR (CDCl$_3$): δ=7.30–7.15 (m,4H), 7.10–7.05 (dd, 1H), 6.95–6.80 (m,2H), 6.90–6.80 (d,1H), 4.60–4.50 (t,2H), 3.60 (s,1H), 3.30–3.20 (t,2H), 1.60 (s,3H), 1.55 (s,3H), 1.30 (s,3H) ppm.

PREPARATION 22

6-(1-(2-Phenylethyl)-1H-tetrazol-5-yl)-2,2,3-trimethyl-2H-benzo[b]pyran

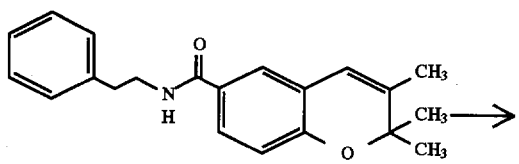

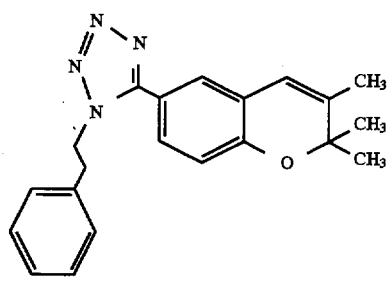

Phosphorus pentachloride (1.2 g) was added to a solution of the compound of Preparation 23 (1.8 g) in chloroform (25 ml) and the mixture was heated under reflux for 15 minutes. On cooling to room temperature, trimethylsilyl azide (0.97 g) was added and the mixture was allowed to stand at room temperature for 16 hours. Water (20 ml) was added and the mixture was stirred vigorously for 20 minutes. The layers were separated and the chloroform solution was dried (MgSO$_4$) then concentrated in vacuo to give the title compound as an oil which solidified on standing, 2.07 g.

$^1$H-NMR (CDCl$_3$): δ=7.30–7.20 (m,3H), 7.00–6.95 (m,3H), 6.80–6.75 (m,2H), 6.05 (s,1H), 4.65–4.55 (t,2H), 3.30–3.20 (t,2H), 1.85 (s,3H), 1.45 (s,6H) ppm.

PREPARATION 23

6-(N-[2-Phenylethyl])carbamoyl-2,2,3-trimethyl-2H-benzo[b]pyran

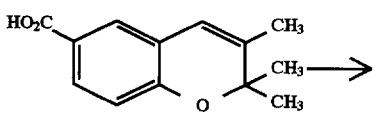

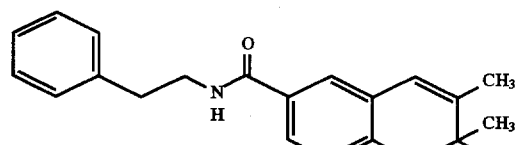

1,1'-Carbonyldiimidazole (1.17 g) was added to a solution of the compound of Preparation 4 (1.5 g) in dichloromethane (30 ml) and the mixture was stirred at room temperature for 30 minutes. 2-Phenylethylamine (1.67 g) was added and the mixture was allowed to stand at room temperature for 16 hours then diluted with dichloromethane to a total volume of 70 ml. The solution was washed sequentially with 10% aqueous sodium hydroxide (50 ml), 2N hydrochloric acid (2×50 ml) and water (50 ml), then concentrated in vacuo to give a solid which was purified by chromatography on silica eluting with dichloromethane containing methanol (1%). The product-containing fractions were combined and concentrated in vacuo to give the title compound as an oil, 1.87 g.

$^1$H-NMR (CDCl$_3$): δ=7.40–7.20 (m,7H), 6.75–6.70 (d,1H), 6.10 (s,1H), 6.05–5.95 (brt, 1H), 3.75–3.65 (q,2H), 2.95–2.90 (q,2H), 1.85 (s,3H), 1.40 (s,6H) ppm.

PREPARATION 24

(3R,4R/3S,4S)-3,4-Dihydro-2,2-dimethyl-3,4-epoxy-6-(1-[2-(4-methoxyphenyl)ethyl]-1H-tetrazol-5-yl)-2H-benzo[b]pyran

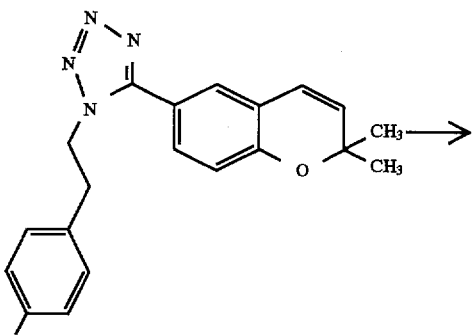

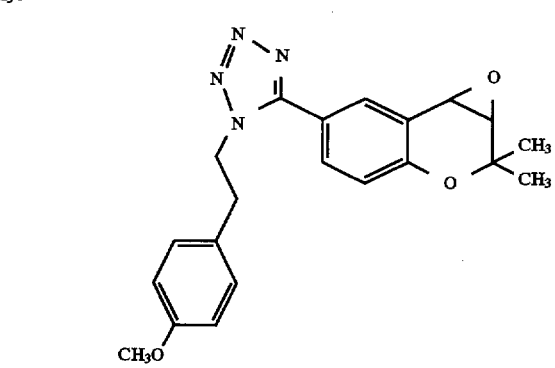

A solution of OXONE™ (12.5 g) in water (50 ml) was added, over 1 hour, to a stirred mixture of the compound of Preparation 25 (3.69 g), sodium hydrogen carbonate (7.9 g), water (50 ml) and acetone (150 ml). When the addition was complete the mixture was stirred at room temperature for a further 1 hour. The acetone was evaporated in vacuo and the resulting aqueous mixture was extracted with dichloromethane (3×100 ml). The dichloromethane solution was dried (Na$_2$SO$_4$) then concentrated in vacuo to give the title compound as a foam, 3.6 g.

$^1$H-NMR (CDCl$_3$): δ=7.15–7.10 (m,2H), 6.90–6.70 (m,5H), 4.60–4.50 (m,2H), 3.80 (d,1H), 3.75 (s,3H), 3.50 (d,1H), 3.25 (t,2H), 1.60 (s,3H), 1.30 (s,3H) ppm.

PREPARATION 25

2,2-Dimethyl-6-(1-[2-(4-methoxyphenyl)ethyl]- 1H-tetrazol-5-yl)-2H-benzo[b]pyran

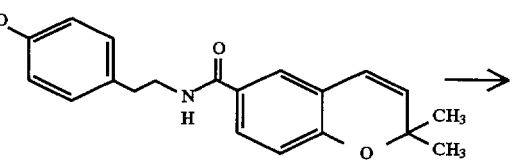

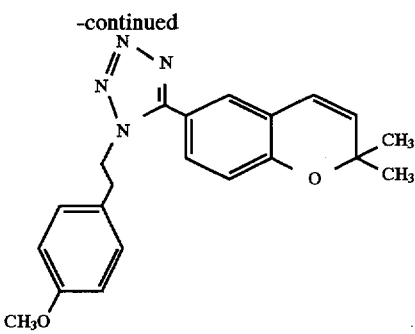

Phosphorus pentachloride (3.4 g) was added to a solution of the compound of Preparation 26 (5.5 g) in chloroform (100 ml) and the mixture was heated under reflux for 15 minutes. On cooling to room temperature trimethylsilyl azide (1.9 g) was added and the mixture was allowed to stand at room temperature for 5 hours. 10% Aqueous ceric ammonium nitrate (100 ml) was added followed by dichloromethane (200 ml) and water (50 ml). The mixture was stirred vigorously for 20 minutes then filtered through a cellulose-based filter aid. The layers were separated and the organic solution was concentrated in vacuo to give an oil which was purified by chromatography on silica eluting with dichloromethane containing methanol (0.1%). The product-containing fractions were combined and concentrated in vacuo to give the title compound as an oil, 3.75 g.

$^1$H-NMR (CDCl$_3$): δ=7.05–7.00 (dd,1H), 6.90–6.70 (m,6H), 6.25–6.20 (d,1H), 5.70–5.65 (d,1H), 4.60–4.50 (t,2H), 3.75 (s,3H), 3.25–3.15 (t,2H), 1.45 (s,6H) ppm.

PREPARATION 26

2,2-Dimethyl-6-(N-[2-(4-methoxyphenyl)ethyl]) carbamoyl-2H-benzo[b]pyran

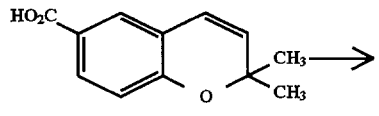

1,1'-Carbonyldiimidazole (2.62 g) was added to a solution of the compound of Preparation 27 (3 g) in dichloromethane (40 ml) and the mixture was heated under reflux for 30 minutes. On cooling to room temperature 2-(4-methoxyphenyl)ethylamine (2.4 g) was added and the mixture was allowed to stand at room temperature for 16 hours. Further 2-(4-methoxyphenyl)ethylamine (2 g) was added and the mixture was allowed to stand at room temperature for 12 days then diluted with dichloromethane to a total volume of 100 ml. The solution was washed sequentially with 10% aqueous sodium hydroxide (50 ml), 2N hydrochloric acid (2×50 ml) and water (50 ml), then dried (Na$_2$SO$_4$) and concentrated in vacuo to give the title compound as a solid, 5.5 g, m.p. 105°–107° C.

$^1$H-NMR (CDCl$_3$): δ=7.45–7.35 (m,2H), 7.15–7.10 (d,2H), 6.90–6.85 (d,2H), 6.75–6.70 (d,1H), 6.35–6.30 (d,1H), 6.05–5.95 (brt, 1H), 5.65–5.60 (d,1H), 3.80 (s,3H), 3.70–3.60 (q,2H), 2.90–2.80 (t,2H), 1.45 (s,6H) ppm.

PREPARATION 27

2,2-Dimethyl-2H-benzo[b]pyran-6-carboxylic Acid

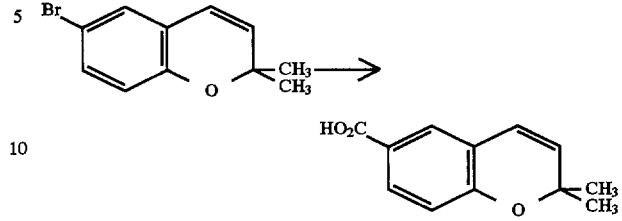

To a solution of 6-bromo-2,2-dimethyl-2H-benzo[b]pyran (see J. Med. Chem., 33, 3028 [1990]) (5.0 g) in dry tetrahydrofuran (100 ml) at −70° C. under nitrogen was added, dropwise, a 1.6M solution of n-butyllithium in hexane (17 ml). The reaction mixture was stirred at −70° C. for 15 minutes then treated with an excess of finely ground solid CO$_2$. The reaction was further stirred for one hour, the solvent evaporated in vacuo and the residue taken up in ethyl acetate and washed with dilute aqueous hydrochloric acid. The organic layer was concentrated in vacuo to a solid which was triturated with hexane to provide a white solid, 1.6 g.

$^1$H-NMR (CDCl$_3$): δ=7.90 (d,1H), 7.76 (s,1H), 6.80 (d,1H), 6.34 (d,1H), 5.67 (d,1H), 1.49 (s,6H) ppm.

PREPARATION 28

(3R,4R/3S,4S)-3,4-Dihydro-2,2-dimethyl-3,4-epoxy-6-(1-[3-phenylprop-1-yl]-1H-tetrazol-5-yl)-2H-benzo[b]pyran

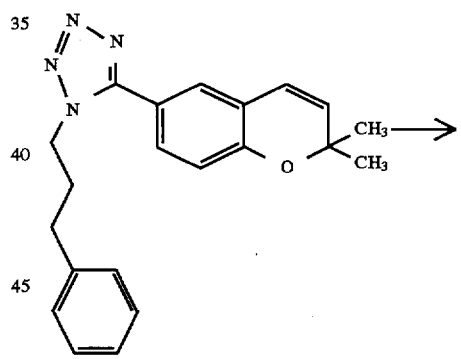

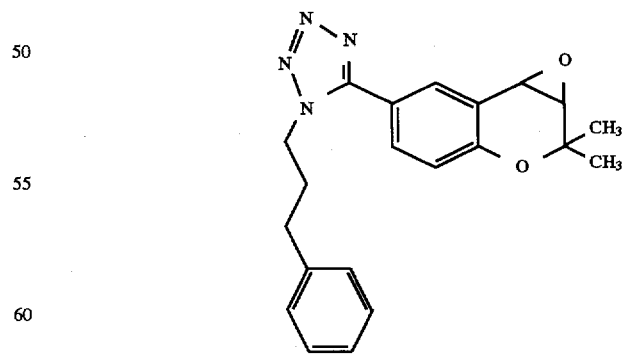

A solution of OXONE™ (4.62 g) in water (20 ml) was added, over 2 hours, to a stirred mixture of the compound of Preparation 29 (2.6 g), sodium hydrogen carbonate (3.5 g), water (20 ml) and acetone (60 ml). When the addition was complete the mixture was stirred at room temperature for a further 1 hour. The acetone was evaporated in vacuo and the resulting aqueous mixture was extracted with dichloromethane (2×100 ml). The dichloromethane solution was dried (Na₂SO₄) then concentrated in vacuo to give the title compound as a foam, 2.6 g.

¹H-NMR (CDCl₃): δ=7.65 (d,1H), 7.40–7.35 (dd,1H), 7.30–7.20 (m,3H), 7.15–7.10 (m,2H), 6.90–6.85 (d,1H), 4.25–4.15 (t,2H), 3.90 (d,1H), 3.55 (d,1H), 2.70–2.60 (t,2H), 2.35–2.20 (.m,2H), 1.65 (s,3H), 1.30 (s,3H) ppm.

PREPARATION 29

2,2-Dimethyl-6-(1-[3-phenylprop-1-yl]-1H-tetrazol-5-yl)-2H-benzo[b]pyran

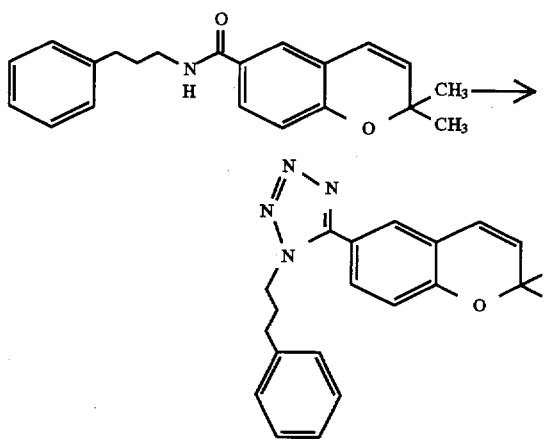

Phosphorus pentachloride (3.3 g) was added to a solution of the compound of Preparation 30 (5.1 g) in chloroform (100 ml) and the mixture was heated under reflux for 15 minutes. On cooling to room temperature trimethylsilyl azide (1.8 g) was added and the mixture was allowed to stand at room temperature for 16 hours. 10% Aqueous ceric ammonium nitrate (100 ml) was added followed by dichloromethane (200 ml) and water (50 ml). The mixture was stirred vigorously for 20 minutes then filtered through a cellulose-based filter aid. The layers were separated and the organic solution was concentrated in vacuo to give an oil which was purified by chromatography on silica eluting with dichloromethane containing methanol (0.25%). The product-containing fractions were combined and concentrated in vacuo to give the title compound as an oil, 2.7 g.

¹H-NMR (CDCl₃): δ=7.30–7.20 (m,5H), 7.15–7.10 (m,2H), 6.85–6.80 (d,1H), 6.35–6.25 (d,1H), 5.75–5.70 (d,1H), 4.45–4.35 (t,2H), 2.70–2.65 (m,2H), 2.35–2.25 (t,2H), 1.50 (s,6H) ppm.

PREPARATION 30

2,2-Dimethyl-6-(N-[3-phenylprop-1-yl])carbamoyl-2H-benzo[b]pyran

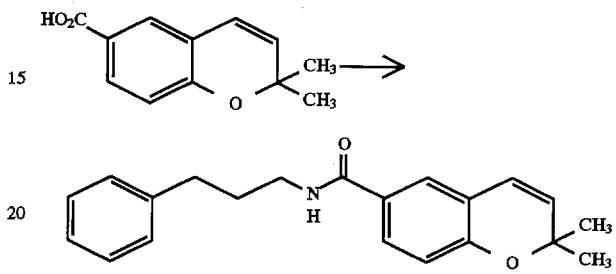

1,1'-Carbonyldiimidazole (2.6 g) was added to a solution of the compound of Preparation 27 (3 g) in dichloromethane (40 ml) and the mixture was heated under reflux for 30 minutes. On cooling to room temperature 1-amino-3-phenylpropane (4 g) was added and the mixture was allowed to stand at room temperature for 12 days. The mixture was diluted with dichloromethane to a total volume of 100 ml then washed sequentially with 10% aqueous sodium hydroxide (50 ml), 2N hydrochloric acid (2×50 ml) and water (50 ml), then dried (Na₂SO₄) and concentrated in vacuo to give the title compound as an oil, 5.17 g.

¹H-NMR (CDCl₃): δ=7.40–7.15 (m,7H), 6.75–6.70 (d,1H), 6.35–6.30 (d,1H), 6.00–5.90 (brs,1H), 5.65–5.60 (d,1H), 3.50–3.40 (m,2H), 2.75–2.70 (t,2H), 2.00–1.90 (m,2H), 1.45 (s,6H) ppm.

PREPARATION 31

6-(1-[2-(4-Benzyloxyphenyl)ethyl]-1H-tetrazol-5-yl)-2,2-dimethyl-2H-benzo[b]pyran

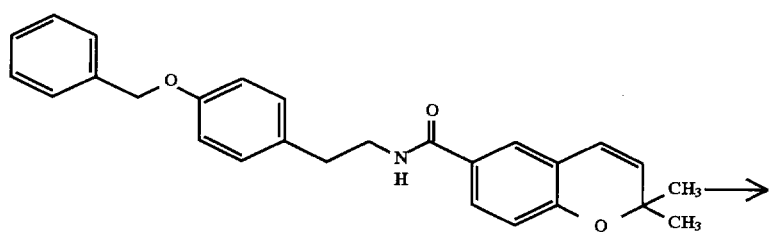

-continued

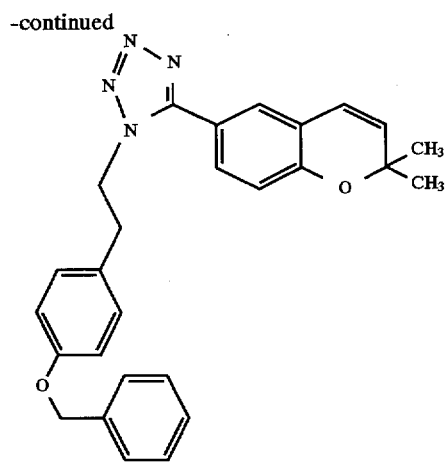

Phosphorus pentachloride (2.2 g) was added to a solution of the compound of Preparation 32 (4.4 g) in chloroform (100 ml) and the mixture was heated under reflux for 15 minutes. On cooling to room temperature tetramethylguanidinium azide (10.6 ml of a 1M solution in dichloromethane) was added and the mixture was allowed to stand at room temperature. After 3 and 6 days, further portions of tetramethylguanidinium azide (8 and 20 ml respectively of a 1M solution in dichloromethane) were added. Following the final addition the mixture was stirred for 24 hours then washed with water (3×100 ml) and concentrated in vacuo. The residue was purified by chromatography on silica eluting with dichloromethane containing methanol (0.5%). The product-containing fractions were combined and concentrated in vacuo to give the title compound as an oil, 3.2 g.

$^1$H-NMR (CDCl$_3$): δ=7.45–7.25 (m,5H), 7.05–7.00 (dd, 1H), 6.90–6.75 (m,6H), 6.25–6.20 (d,1H), 5.70–5.65 (d,1H), 5.00 (s,2H), 4.60–4.50 (t,2H), 3.25–3.15 (t,2H), 1.45 (s,6H) ppm.

which was purified by chromatography on silica eluting with dichloromethane containing methanol (1%). The product-containing fractions were combined and concentrated in vacuo to give the title compound as a solid, 4.7 g, m.p. 133°–135° C. Found: C,78.26; H,6.49; N,3.34; C$_{27}$H$_{27}$NO$_3$ requires: C,78.42; H,6.49; N,3.39%.

$^1$H-NMR (CDCl$_3$): δ=7.45–7.30 (m,7H), 7.15–7.10 (d,2H), 6.95–6.90 (d,2H), 6.75–6.70 (d,1H), 6.35–6.30 (d,1H), 6.05–5.95 (brt, 1H), 5.65–5.60 (d,1H), 5.05 (s,2H), 3.70–3.60 (q,2H), 2.90–2.80 (t,2H), 1.45 (s,6H) ppm.

PREPARATION 32

6-(N-[2-(4-Benzyloxyphenyl)ethyl])carbamoyl-2,2-dimethyl-2H-benzo[b]pyran

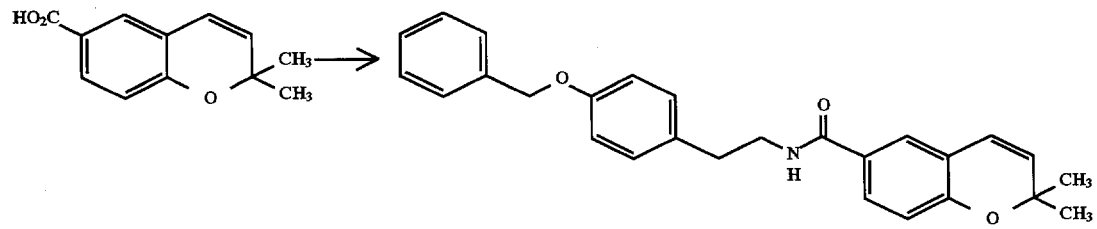

1,1'-Carbonyldiimidazole (2.6 g) was added to a solution of the compound of Preparation 27 (3 g) in dichloromethane (40 ml) and the mixture was heated under reflux for 30 minutes. On cooling to room temperature 2-(4-benzyloxyphenyl)ethylamine (4 g) and dichloromethane (50 ml) were added and the mixture was allowed to stand at room temperature for 12 days. The mixture was diluted with dichloromethane to a total volume of 100 ml then washed sequentially with 10% aqueous sodium hydroxide (50 ml), 2N hydrochloric acid (2×50 ml) and water (50 ml), then dried (Na$_2$SO$_4$) and concentrated in vacuo to give a solid

PREPARATION 33

(3R,4R/3S,4S)-3,4-Dihydro-2,2-dimethyl-3,4-epoxy-6-(1-[4-phenylbut-1-yl]-1H-tetrazol-5-yl)-2H-benzo[b]pyran

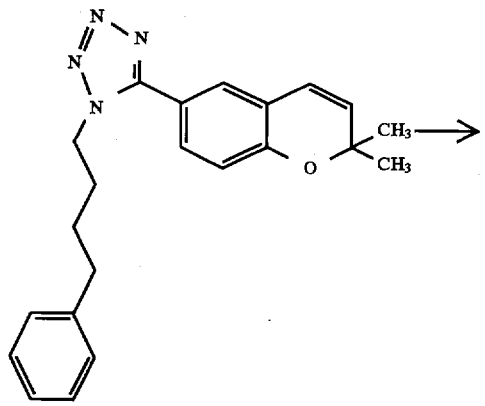

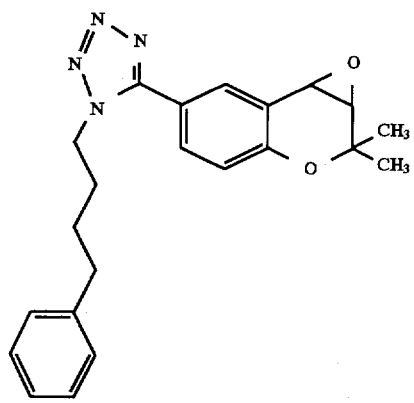

A solution of OXONE™ (7 g) in water (30 ml) was added, over 2 hours, to a stirred mixture of the compound of Preparation 34 (4 g), sodium hydrogen carbonate (4 g), water (30 ml) and acetone (90 ml). When the addition was complete the mixture was stirred at room temperature for a further 1 hour. The acetone was evaporated in vacuo and the resulting aqueous mixture was extracted with dichloromethane (2×100 ml). The dichloromethane solution was dried (Na$_2$SO$_4$) then concentrated in vacuo to give the title compound as an oil, 4.1 g.

$^1$H-NMR (CDCl$_3$): δ=7.65 (d,1H), 7.45–7.40 (d,1H), 7.35–7.10 (m,5H), 7.00–6.95 (d,1H), 4.45–4.35 (t,2H), 3.95 (d,1H), 3.55 (d,1H), 2.70–2.55 (t,2H), 2.00–1.90 (m,2H), 1.70–1.55 (m,2H), 1.60 (s,3H), 1.30 (s,3H) ppm.

PREPARATION 34

2,2-Dimethyl-6-(1-[4-phenylbut-1-yl]-1H-tetrazol-5-yl)-2H-benzo[b]pyran

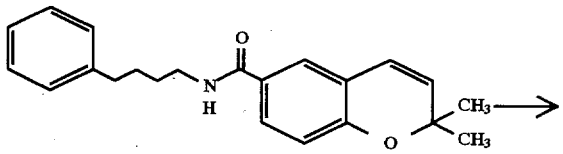

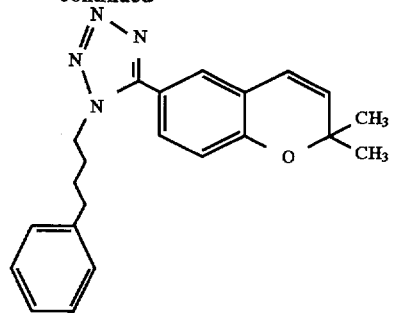

Phosphorus pentachloride (3.1 g) was added to a solution of the compound of Preparation 35 (5.3 g) in chloroform (100 ml) and the mixture was heated under: reflux for 15 minutes. On cooling to room temperature trimethylsilyl azide (1.7 g) was added and the mixture allowed to stand at room temperature for 16 hours. The mixture was washed with water (100 ml) and concentrated in vacuo to give an oil which was purified by chromatography on silica eluting with dichloromethane containing methanol (0.5%). The product-containing fractions were combined and concentrated in vacuo to give the title compound as an oil, 4.07 g.

$^1$H-NMR (CDCl$_3$): δ=7.35–7.05 (m,7H), 6.90 (d,1H), 6.35–6.30 (d,1H), 5.75–5.70 (d,1H), 4.45–4.35 (t,2H), 2.65–2.55 (t,2H), 2.00–1.90 (m,2H), 1.70–1.60 (m,2H), 1.45 (s,6H) ppm.

PREPARATION 35

2,2-Dimethyl-6-(N-[4-phenylbut-1-yl])carbamoyl-2H-benzo[b]pyran

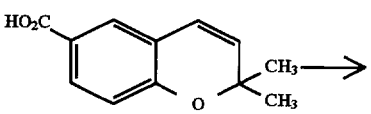

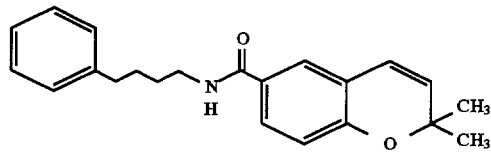

1,1'-Carbonyldiimidazole (2.62 g) was added to a solution of the compound of Preparation 27 (3 g) in dichloromethane (40 ml) and the mixture was stirred at room temperature for 30 minutes. 1-Amino-4-phenylbutane (4.4 g) was added and the mixture was allowed to stand at room temperature for 3 days. The mixture was washed sequentially with water (100 ml), 2N hydrochloric acid (2×50 ml) and water (100 ml), then dried (Na$_2$SO$_4$) and concentrated in vacuo to give the title compound as an oil which crystallised on standing, 5.35 g, m.p. 65°–70° C.

$^1$H-NMR (CDCl$_3$): δ=7.50–7.45 (dd,1H), 7.40 (d,1H), 7.30–7.10 (m,5H), 6.80–6.75 (d,1H), 6.35–6.30 (d,1H), 6.10–6.00 (br$^+$, 1H); 5.65–5.60 (d,1H), 3.50–3.40 (m,2H), 2.70–2.60 (m,2H), 1.75–1.60 (m,4H), 1.45 (s,6H) ppm.

PREPARATION 36

(3R,4R/3S,4S)-3,4-Dihydro-2,2-dimethyl-3,4-epoxy-6-(1-[3-ethoxycarbonylprop-1-yl]-1H-tetrazol-5-yl)-2H-benzo[b]pyran

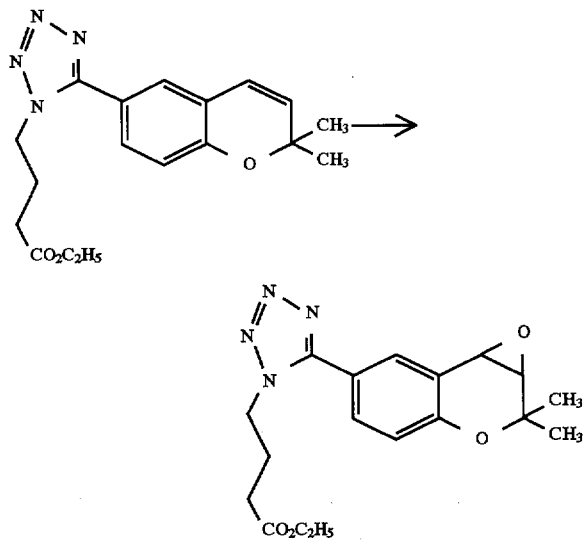

A solution of OXONE™ (2.2 g) in water (10 ml) was added, over 1.5 hours, to a stirred mixture of the compound of Preparation 37 (1.2 g), sodium hydrogen carbonate (1.2 g), water (8 ml) and acetone (30 ml). When the addition was complete the mixture was stirred at room temperature for a further 30 minutes. The acetone was evaporated in vacuo and the resulting aqueous mixture was extracted with dichloromethane (2×100 ml). The dichloromethane solution was dried (MgSO₄) then concentrated in vacuo to give the title compound as an oil, 1.1 g.

¹H-NMR (CDCl₃): δ=7.80 (d,1H), 7.65–7.55 (dd,1H), 7.00–6.95 (d,1H), 4.55–4.50 (t,2H), 4.15–4.05(q,2H), 4.00 (d,1H), 3.55 (d,1H), 2.45–2.40 (m,2H), 2.30–2.20 (m,2H), 1.65 (s,3H), 1.30 (s,3H), 1.30–1.20 (t,3H) ppm.

PREPARATION 37

2,2-Dimethyl-6-(1-[3-ethoxycarbonylprop-1-yl]-1H-tetrazol-5-yl)-2H-benzo[b]pyran

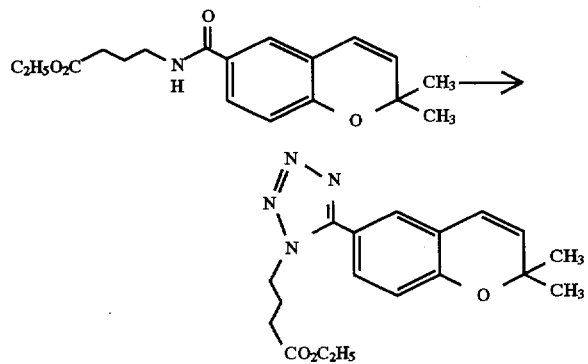

Phosphorus pentachloride (0.66 g) was added to a solution of the compound of Preparation 38 (1 g) in chloroform (20 ml) and the mixture was heated under reflux for 15 minutes. On cooling to room temperature trimethylsilyl azide (0.54 g) was added and the mixture was allowed to stand at room temperature for 4 days. The mixture was washed with water (100 ml), dried (MgSO₄) and concentrated in vacuo to give the title compound as an oil, 1.28 g, ¹H-NMR (CDCl₃): δ=7.45–7.40 (dd,1H), 7.40 (d,1H), 6.90 (d,1H), 6.40–6.35 (d,1H), 5.70 (d,1H), 4.55–4.45 (t,2H), 4.10–4.05 (q,2H), 2.45–2.35 (t,2H), 2.30–2.20 (m,2H), 1.45 (s,6H), 1.30–1.20 (t,3H) ppm.

PREPARATION 38

2,2-Dimethyl-6-(N-[3-ethoxycarbonylprop-1-yl])carbamoyl-2H-benzo[b]pyran

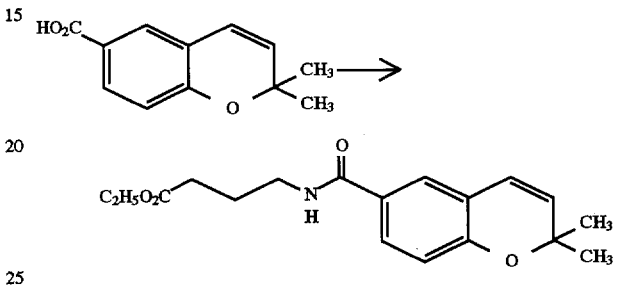

1,1'-Carbonyldiimidazole (4.4 g) was added to a solution of the compound of Preparation 27 (5 g) in dichloromethane (100 ml) and the mixture was stirred at room temperature for 30 minutes. Ethyl 4-aminobutanoate hydrochloride (4.5 g) was added and the mixture was allowed to stand at room temperature for 7 days. The mixture was washed with water (100 ml) then concentrated in vacuo to give a gum which was purified by chromatography on silica eluting with dichloromethane containing methanol (1.25%). The product-containing fractions were combined and concentrated in vacuo to give the title compound as a solid, 4.3 g, m.p. 88°–89° C.

¹H-NMR (CDCl₃): δ=7.60–7.50 (dd,1H), 7.45 (d,1H), 6.85–6.75 (d,1H), 6.45–6.40 (brt,1H), 6.40–6.35 (d,1H), 5.70–5.65 (d,1H), 4.20–4.10 (m,2H), 3.55–3.45 (q,2H), 2.50–2.45 (m,2H), 2.05–1.95 (m,2H), 1.50 (s,6H), 1.30–1.25 (t,3H) ppm.

PREPARATION 39

(3R,4R/3S,4S)-6-(1-[2-Benzyloxyethyl]-1H-tetrazol-5-yl)-3,4-dihydro-2,2-dimethyl-3,4-epoxy-2H-benzo[b]pyran

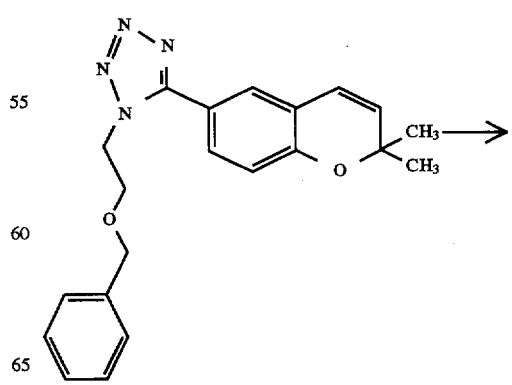

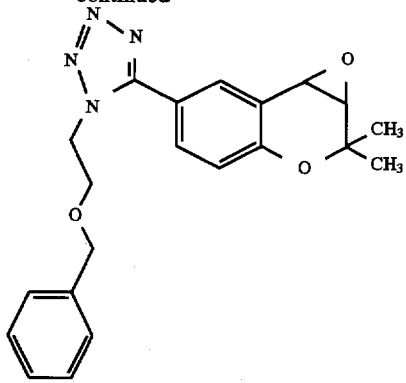

A solution of OXONE™ (6.8 g) in water (20 ml) was added, over 1 hour, to a stirred mixture of the compound of Preparation 40 (4 g) sodium hydrogen carbonate (5.5 g), water (60 ml) and acetone (20 ml). When the addition was complete the mixture was stirred at room temperature for a further 30 minutes. The acetone was evaporated in vacuo and the resulting aqueous mixture was extracted with dichloromethane (2×100 ml). The dichloromethane solution was dried ($Na_2SO_4$) then concentrated in vacuo to give the title compound as a foam, 3.2 g.

$^1$H-NMR ($CDCl_3$): δ=7.85 (d,1H), 7.70–7.65 (dd,1H), 7.35–7.25 (m,3H), 7.20–7.15 (m,2H), 6.90 (d,1H), 4.60–4.55 (t,2H), 4.50 (s,2H), 4.05–4.00 (t,2H), 3.75 (d,1H), 3.50 (d,1H), 1.60 (s,3H), 1.30 (s,3H) ppm.

PREPARATION 40

6-(1-[2-Benzyloxyethyl]-1H-tetrazol-5-yl)-2, 2-dimethyl-2H-benzo[b]pyran

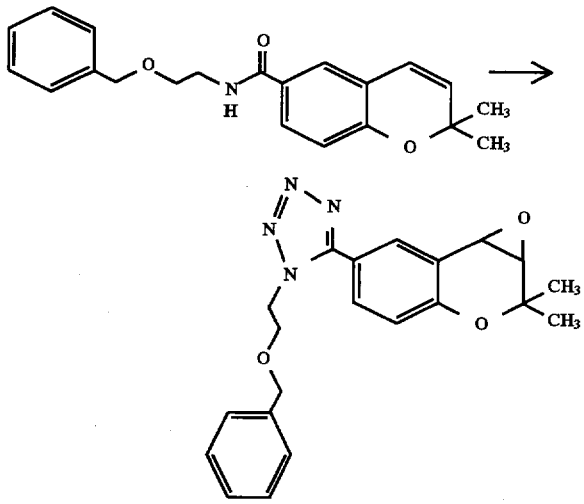

Phosphorus pentachloride (9.9 g) was added to a solution of the compound of Preparation 41 (16 g) in chloroform (300 ml) and the mixture was heated under reflux for 15 minutes. On cooling to room temperature trimethylsilyl azide (5.5 g) was added and the mixture was allowed to stand at room temperature for a total of 2 days during which time further trimethylsilyl azide was added after 16 (1.5 g) and 43 (0.5 g) hours. The mixture was washed with water (200 ml), dried ($MgSO_4$) and concentrated in vacuo to give the title compound as an oil, 20.6 g.

$^1$H-NMR ($CDCl_3$): δ=7.55–7.50 (dd,1H), 7.45 (d,1H), 7.35–7.25 (m,3H), 7.20–7.15 (m,2H), 6.90–6.85 (d,1H), 6.25–6.20 (d,1H), 5.70–5.65 (d,1H), 4.60–4.50 (t,2H), 4.45 (s,2H), 4.05–4.00 (t,2H), 1.45 (s,6H) ppm.

PREPARATION 41

6-(N-[2-Benzyloxyethyl])carbamoyl-2,2-dimethyl-2H-benzo [b]pyran

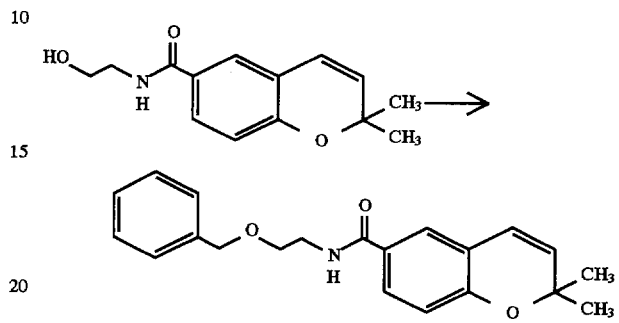

Sodium hydride (1.72 g of an 80% suspension in mineral oil) was added, in portions, over 10 minutes to a cooled (0° C.) solution of the compound of Preparation 42 (14.2 g) in anhydrous tetrahydrofuran (200 ml). The mixture was stirred at room temperature for 30 minutes then re-cooled to 0° C. and a solution of benzyl bromide (9.94 g) in anhydrous tetrahydrofuran: (10 ml) was added over 15 minutes. When the addition was complete the mixture was allowed to warm to room temperature and was stirred for 18 hours. Water (250 ml) was added and the mixture was extracted with diethyl ether (2×300 ml). The ethereal extracts were concentrated in vacuo and the residue was dissolved in dichloromethane (100 ml). The water which separated was removed and the organic layer was concentrated in vacuo to give an oil which was purified by chromatography on silica eluting with dichloromethane containing methanol (0.5%). The product-containing fractions were combined and concentrated in vacuo to give the title compound as an oil, 15.5 g.

$^1$H-NMR ($CDCl_3$): δ=7.50–7.45 (dd,1H), 7.45 (d,1H), 7.35–7.25 (m,5H), 6.80–6.75 (d,1H), 6.45–6.35 (brs,1H), 6.35–6.30 (d,1H), 5.70–5.65 (d,1H), 4.55 (s,2H), 3.65 (s,4H), 1.45 (s,6H) ppm.

PREPARATION 42

2,2-Dimethyl-6-(N-[2-hydroxyethyl])carbamoyl-2H-benzo[b]pyran

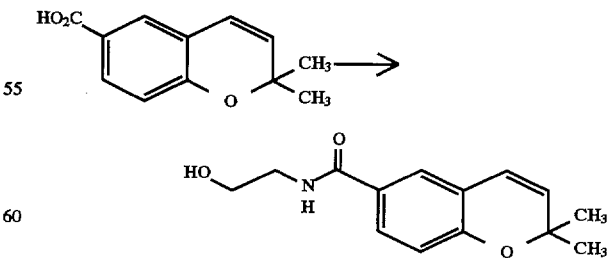

1,1'-Carbonyldiimidazole (10.5 g) was added, in three portions, to a solution of the compound of Preparation 27 (12 g) in dichloromethane (250 ml) and the mixture was stirred at room temperature for 30 minutes. Ethanolamine (10 g) was added and the mixture was stirred at room temperature for 4 days. The mixture was washed with water (250 ml) and the washings back-extracted with dichloromethane (100 ml). The dichloromethane extracts were combined and concentrated in vacuo and the residue was purified by chromatography on silica eluting with dichloromethane containing methanol (5%). The product-containing fractions were combined and concentrated in vacuo to give a foam which was azeotroped with dichloromethane and ethyl acetate to give the title compound as a colourless solid, 12.25 g, m.p. 60°–70° C.

¹H-NMR (CDCl₃): δ=7.55–7.50 (dd,1H), 7.45 (d,1H), 6.80–6.75 (d,1H), 6.70–6.60 (brs,1H), 6.30 (d,1H), 5.65–5.60 (d,1H), 3.85–3.75 (m,2H), 3.65–3.55 (m,2H), 3.05–3.00 (t, 1H), 1.45 (s,6H) ppm.

PREPARATION 43

(3R,4R/3S,4S)-3,4-Dihydro-2,2-dimethyl-3,4-epoxy-6-(1-[2-phthalimidoethyl]-1H-tetrazol-5-yl)-2H-benzo[b]pyran

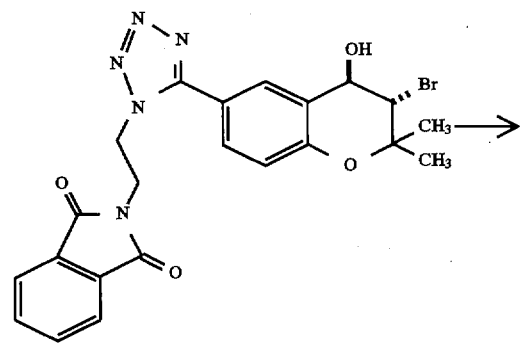

(only one stereoisomer shown)

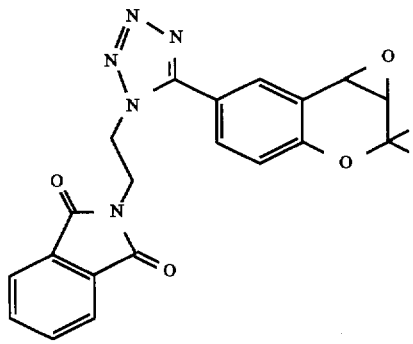

Sodium hydride (0.6 g of an 80% suspension in mineral oil) was added to a solution of the compound of Preparation 44 (8.6 g) in anhydrous dimethyl sulfoxide (40 ml) and the mixture was stirred at room temperature for 30 minutes. The mixture was poured onto ice (100 g) and extracted with ethyl acetate (3×100 ml). The organic extracts were combined and washed with saturated sodium chloride solution (2×100 ml), then dried (MgSO₄) and concentrated in vacuo to give the title compound, 5.6 g.

¹H-NMR (CDCl₃): δ=7.80–7.65 (m,5H), 7.55–7.50 (dd, 1H), 6.90–6.85 (d,1H), 4.85–4.75 (m,2H), 4.15–4.05 (m,2H), 3.90 (d,1H), 3.50 (d,1H), 1.60 (s,3H), 1.30 (s,3H) ppm.

PREPARATION 44

(3R,4S/3S,4R)-3-Bromo-3,4-dihydro-2,2-dimethyl-4-hydroxy-6-(1-[2-phthalimidoethyl]-1H-tetrazol-5-yl)-2H-benzo[b]pyran

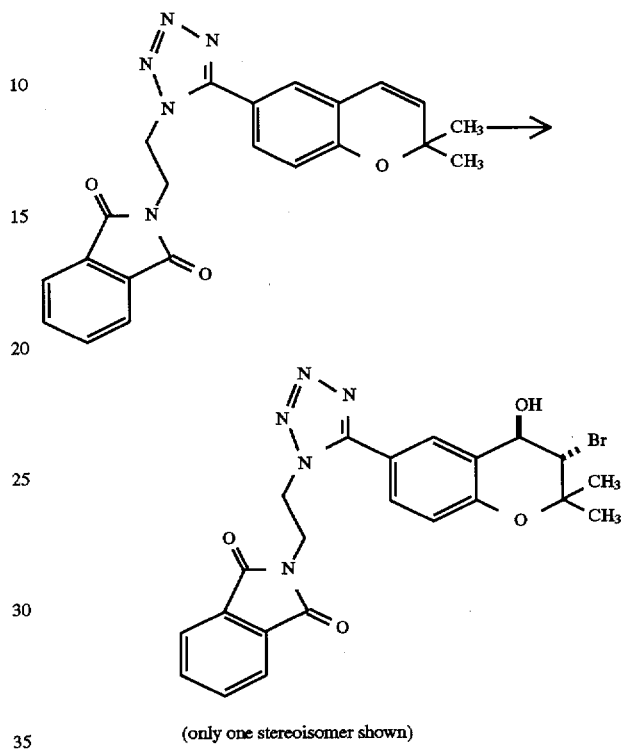

(only one stereoisomer shown)

Water (0.5 ml) was added to a solution of the compound of Preparation 45 (7.74 g) in dimethyl sulfoxide (110 ml) and the mixture was cooled to 0° C. in an ice bath. N-Bromosuccinimide (7 g) was added and the mixture was stirred at room temperature for 1 hour then poured onto ice (200 g). The mixture was extracted with ethyl acetate (300 ml) and the extract was washed with saturated sodium chloride solution (2×100 ml), dried (MgSO₄) and concentrated in vacuo to give the title compound as a foam, 9.1 g.

¹H-NMR (CDCl₃): δ=7.90–7.65 (m,5H), 7.55–7.50 (dd, 1H), 6.80 (d,1H), 4.95–4.90 (d,1H), 4.90–4.75 (m,2H), 4.20–4.05 (m,3H), 1.65 (s,3H), 1.45 (s,3H) ppm.

PREPARATION 45

2,2-Dimethyl-6-(1-[2-phthalimidoethyl]-1H-tetrazol-5-yl)-2H-benzo[b]pyran

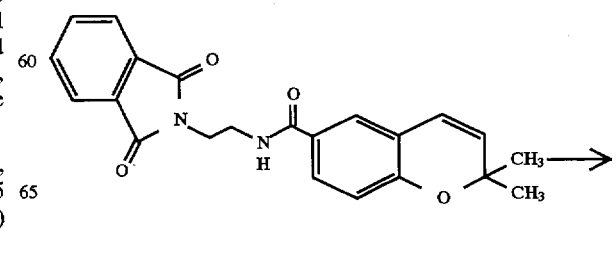

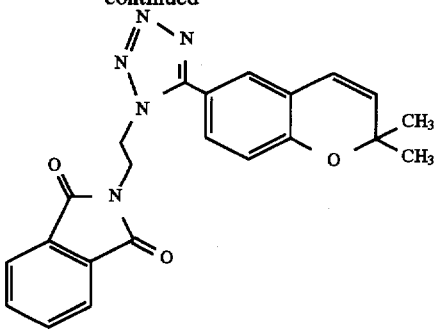

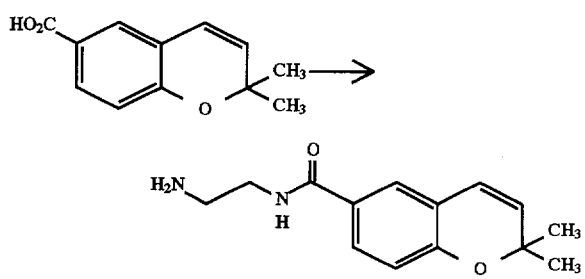

PREPARATION 47

6-(N-[2-Aminoethyl])carbamoyl-2,2-dimethyl-2H-benzo[b]pyran

Phosphorus pentachloride (4.9 g) was added to a solution of the compound of Preparation 46 (8.6 g) in chloroform (200 ml) and the mixture was heated under reflux for 15 minutes. On cooling to room temperature trimethylsilyl azide (4.3 g) was added and the mixture was allowed to stand at room temperature for 18 hours. Water (100 ml) was added and the mixture was stirred vigorously for 10 minutes. The layers were separated and the aqueous layer was extracted with dichloromethane (100 ml). The combined organic extracts were dried ($Na_2SO_4$) and concentrated in vacuo to give the title compound as a solid, 9.5 g, m.p. 178°–182° C.

$^1$H-NMR ($CDCl_3$): δ=7.80–7.70 (m,4H), 7.35–7.30 (dd, 1H), 7.25 (d,1H), 6.75–6.70 (d,1H), 6.30–6.25 (d,1H), 5.70–5.65 (d,1H), 4.85–4.75 (t,2H), 4.15–4.05 (t,2H), 1.45 (s,6H) ppm.

1,1'-Carbonyldiimidazole (4.4 g) was added to a solution of the compound of Preparation 27 (5 g) in dichloromethane (80 ml) and the mixture was stirred for 30 minutes at room temperature. 1,2-Diaminoethane (4 g) was added and the mixture was allowed to stand at room temperature for 16 hours. The mixture was concentrated in vacuo to give a solid which was purified by chromatography on silica eluting with dichloromethane containing methanol (2.5 up to 20%) and concentrated aqueous ammonia (0 up to 1%). The product-containing fractions were combined and concentrated in vacuo to give the title compound as an oil, 4.9 g.

$^1$H-NMR ($CDCl_3$): δ=7.55–7.50 (dd,1H), 7.45 (s,1H), 6.80–6.70 (m,2H), 6.30 (d,1H), 5.65–5,60 (d,1H), 3.50–3.40 (m,2H), 2.95–2.90 (t,2H), 1.80–1.75 (brs,2H), 1.40 (s,6H) ppm.

PREPARATION 46

2,2-Dimethyl-6-(N-[2-phthalimidoethyl])carbamoyl-2H-benzo[b]pyran

PREPARATION 48

(3S,4R)-6-(1-[3-Carboxyprop-1-yl]-1H-tetrazol-5-yl)-3,4-dihydro-3-hydroxy-4-(3-hydroxypyridazin-6-yl)oxy-2,2,3-trimethyl-2H-benzo [b]pyran

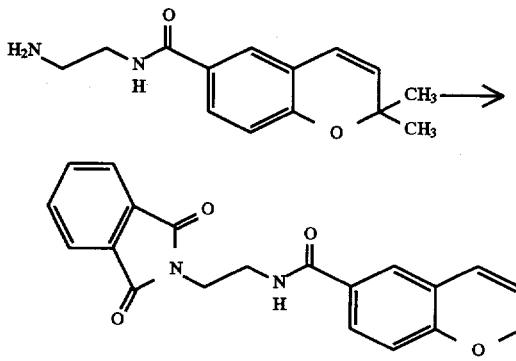

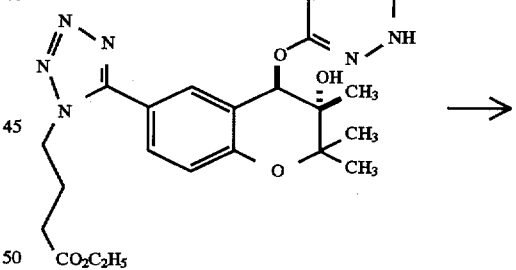

A mixture of the compound of Preparation 47 (0.57 g) and phthalic anhydride (0.35 g) was heated with stirring at 175°–185° C. for 15 minutes. On cooling to room temperature the mixture was purified by chromatography on silica eluting with dichloromethane containing methanol (8%) and concentrated aqueous ammonia (0.4%). The product-containing fractions were combined and concentrated in vacuo to give the title compound as a solid, 0.58 g, m.p. 183°–185° C.

$^1$H-NMR ($CDCl_3$): δ=7.90–7.85 (m,2H), 7.75–7.70 (m,2H), 7.50–7.45 (dd,1H), 7.45 (d,1H), 6.80–6.75 (m,2H), 6.35–6.30 (d,1H), 5.65–5.60 (d,1H), 4.05–3.95 (m,2H), 3.75–3.70 (m,2H), 1.45 (s,6H) ppm.

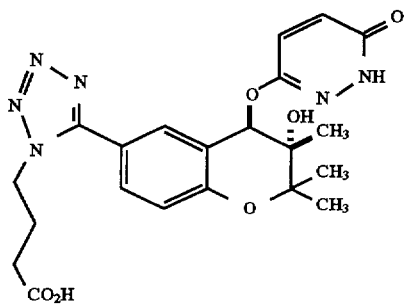

A mixture of the compound of Example 1 (0.078 g), sodium hydroxide (1 ml of a 0.35M aqueous solution) and ethanol (1 ml) was allowed to stand at room temperature for 1 hour. The mixture was acidified to pH1 by the addition of 2N hydrochloric acid and the ethanol was removed in vacuo to leave a gum. The water was decanted off and the residual gum was triturated twice with water then dried in vacuo to give the title compound as a solid, 0.046 g, m.p. 116°–126° C. Found: C, 53.97; H, 5.45; N, 17.79; $C_{21}H_{24}N_6O_6 \cdot 0.5H_2O$ requires: C, 54.19; H, 5.41; N, 18.06%.

$^1$H-NMR (d$_6$-DMSO): δ=7.65–7.55 (m,2H), 7.30–7.20 (d,1H), 7.00–6.85 (m,2H), 5.95 (s,1H), 5.50–5.20 (brs,1H), 4.45–4.30 (m,2H), 2.30–2.20 (m,2H), 2.05–1.90 (m,2H), 1.40 (s,3H), 1.30 (s,3H), 1.20 (s,3H) ppm.

PREPARATION 49

(3R,4R/3S,4S)-3,4-Dihydro-2,2-dimethyl-3,4-epoxy-6-(1-[2-(3-methoxyphenyl)ethyl]-1H-tetrazol-5-yl)-2H-benzo[b]pyran

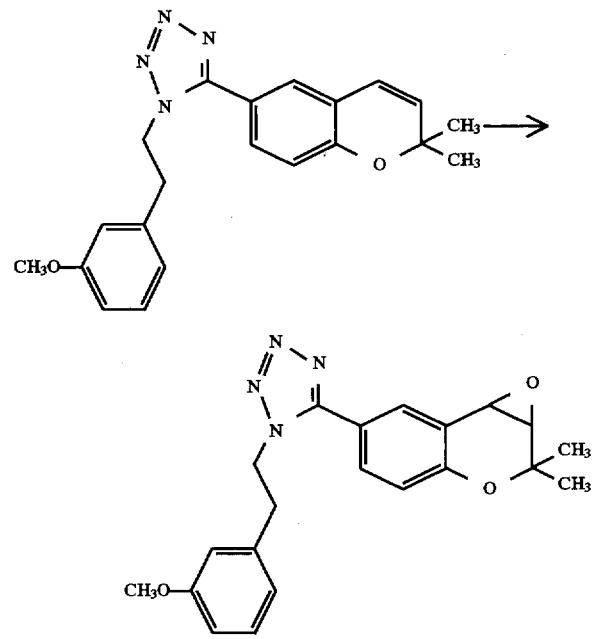

A solution of OXONE™ (5 g) in water (20 ml) was added, over 1 hour, to a stirred mixture of the compound of Preparation 50 (2.8 g), sodium hydrogen carbonate (3.25 g), water (20 ml) and acetone (60 ml). When the addition was complete the mixture was stirred at room temperature for a further 45 minutes. The acetone was evaporated in vacuo and the resulting aqueous mixture was extracted with dichloromethane (2×100 ml). The dichloromethane solution was dried (Na$_2$SO$_4$) then concentrated in vacuo to give the title compound as a foam, 2.6 g.

$^1$H-NMR (CDCl$_3$): δ=7.15–7.05 (m,3H), 6.85–6.80 (d,1H) 6.80–6.75 (dd,1H), 6.55–6.50 (d,1H), 6.45 (s,1H), 4.65–4.55 (m,2H), 3.85 (d,1H), 3.70 (s,3H), 3.50 (d,1H), 3.30–3.20 (t,2H), 1.65 (s,3H), 1.30 (s,3H) ppm.

PREPARATION 50

2,2-Dimethyl-6-(1-[2-(3-methoxyphenyl)ethyl]-1H-tetrazol-5-yl)-2H-benzo[b]pyran

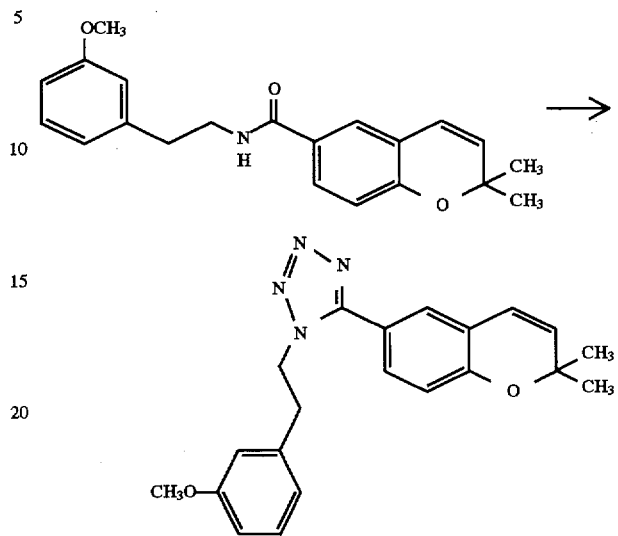

Phosphorus pentachloride (3.2 g) was added to a solution of the compound of Preparation 51 (5.17 g) in chloroform (100 ml) and the mixture was heated under reflux for 15 minutes. On cooling to room temperature trimethylsilyl azide (1.8 g) was added and the mixture was allowed to stand at room temperature for 5 hours. 10% Aqueous ceric ammonium nitrate (100 ml) was added followed by dichloromethane (200 ml) and water (50 ml). The mixture was stirred vigorously for 20 minutes and then was filtered through a cellulose-based filter aid. The layers were separated and the organic solution was concentrated in vacuo to give an oil which was purified by chromatography on silica eluting with dichloromethane containing methanol (0.25%). The product-containing fractions were combined and concentrated in vacuo to give the title compound as an oil, 2.9 g.

$^1$H-NMR (CDCl$_3$): δ=7.15–7.10 (t,1H), 7.05–7.00 (dd, 1H), 6.85–6.75 (m,3H), 6.55–6.50 (d,1H), 6.45 (s,1H), 6.25–6.20 (d,1H), 5.70–5.65 (d,1H), 4.60–4.55 (t,2H), 3.70 (s,3H), 3.25–3.20 (t,2H), 1.45 (s,6H) ppm.

PREPARATION 51

2,2-Dimethyl-6-(N-[2-(3-methoxyphenyl)ethyl])carbamoyl-2H-benzo[b]pyran

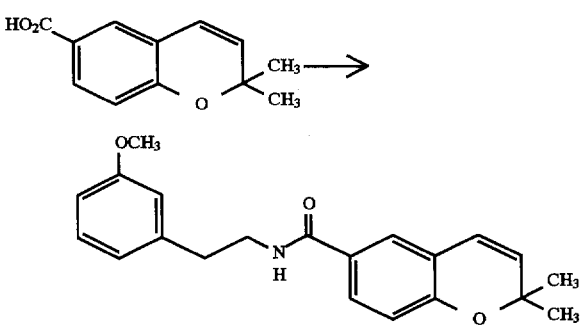

1,1'-Carbonyldiimidazole (2.62 g) was added to a solution of the compound of Preparation 27 (3 g) in dichloromethane (40 ml) and the mixture was heated under reflux for 30 minutes. On cooling to room temperature 2-(3-methoxyphenyl)ethylamine (2.4 g) was added and the mixture was allowed to stand at room temperature for 12 days. The mixture was diluted with dichloromethane to a total volume of 100 ml, then washed sequentially with 10% aqueous sodium hydroxide (50 ml), 2N hydrochloric acid (2×50 ml) and water (50 ml), then dried (Na$_2$SO$_4$) and concentrated in vacuo to give the title compound as an oil which crystallised on standing, 5.26 g, m.p. 105°–110° C.

$^1$H-NMR (CDCl$_3$): δ=7.45–7.35 (m,2H), 7.30–7.20 (m,1H), 6.85–6.70 (m,4H), 6.30 (d,1H), 6.05–6.00 (brt,1H), 5.65–5.60 (d,1H), 3.80 (s,3H), 3.75–3.65 (m,2H), 2.95–2.85 (t,2H), 1.45 (s,6H) ppm.

PREPARATION 52

(3R,4R/3S,4S)-3,4-Dihydro-2,2-dimethyl-3,4-epoxy-6-(1-[2-(2-methoxyphenyl)ethyl]-1H-tetrazol-5-yl)-2H-benzo[b]-pyran

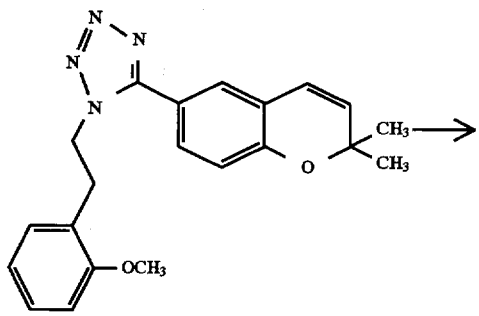

A solution of OXONE™ (4.5 g) in water (20 ml) was added, over 1 hour, to a stirred mixture of the compound of Preparation 53 (2.5 g), sodium hydrogen carbonate (2.9 g), water (20 ml) and acetone (60 ml). When the addition was complete the mixture was stirred at room temperature for a further 45 minutes. The acetone was evaporated in vacuo and the resulting aqueous mixture was extracted with dichloromethane (3×100 ml). The dichloromethane solution was dried (Na$_2$SO$_4$) then concentrated in vacuo to give the title compound as a solid, 2.8 g.

$^1$H-NMR (CDCl$_3$): δ=7.30–7.15 (m,3H), 6.90–6.70 (m,4H), 4.70–4.60 (t,2H), 3.85 (d,1H), 3.65 (s,3H), 3.55 (d,1H), 3.30–3.15 (m,2H), 1.60 (s,3H), 1.30 (s,3H) ppm.

PREPARATION 53

2,2-Dimethyl-6-(1-[2-(2-methoxyphenyl)ethyl]-1H-tetrazol-5-yl)-2H-benzo[b]pyran

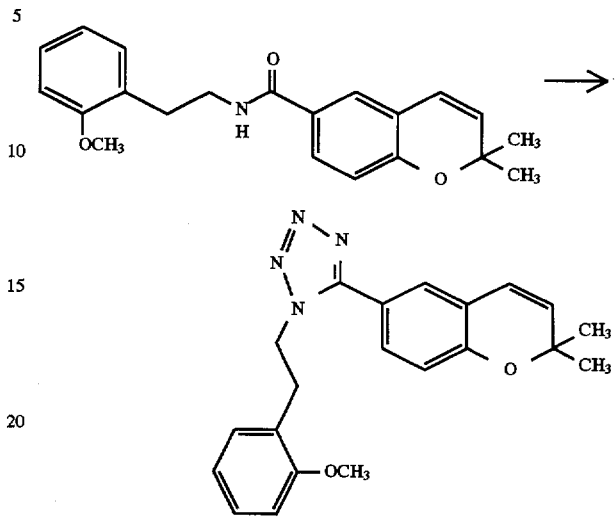

Phosphorus pentachloride (3.1 g) was added to a solution of the compound of Preparation 54 (5 g) in chloroform (100 ml) and the mixture was heated under reflux for 15 minutes. On cooling to room temperature trimethylsilyl azide (1.7 g) was added and the mixture was allowed to stand at room temperature for 16 hours. 10% Aqueous ceric ammonium nitrate (100 ml) was added followed by dichloromethane (250 ml) and water (50 ml). The mixture was stirred vigorously for 20 minutes then filtered through a cellulose-based filter aid. The layers were separated and the organic layer was concentrated in vacuo to give an oil which was purified by chromatography on silica eluting with dichloromethane containing methanol (0.25%). The product-containing fractions were combined and concentrated in vacuo to give the title compound as a solid, 2.65 g, m.p. 101°–105° C.

$^1$H-NMR (CDCl$_3$): δ=7.20–7.10 (m,2H), 6.95 (d,1H), 6.90–6.75 (m,3H), 6.75–6.70 (d,1H), 6.30–6.25 (d,1H), 5.70 (d,1H), 4.70–4.60 (t,2H), 3.65 (s,3H), 3.25–3.20 (t,2H), 1.50 (s,6H) ppm.

PREPARATION 54

2,2-Dimethyl-6-(N-[2-(2-methoxyphenyl)ethyl]carbamoyl)-2H-benzo[b]pyran

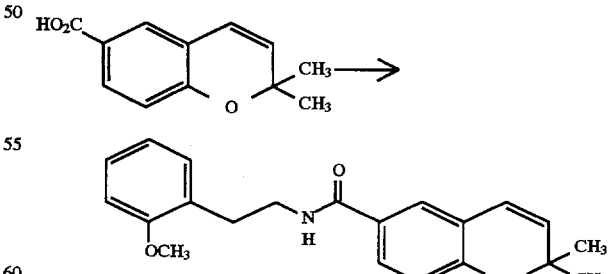

1,1'-Carbonyldiimidazole (2.62 g) was added to a solution of the compound of Preparation 27 (3 g) in dichloromethane (40 ml) and the mixture was heated under reflux for 30 minutes. On cooling to room temperature 1-amino-2-(2-methoxyphenyl)ethane (4 g) was added and the mixture was allowed to stand at room temperature for 12 days. The mixture was diluted with dichloromethane to a total volume of 100 ml then washed sequentially with 10% aqueous sodium hydroxide (50 ml), 2N hydrochloric acid (2×50 ml) and water (50 ml), then dried (Na$_2$SO$_4$) and concentrated in vacuo to give the title compound as a solid, 5.15 g, m.p. 125°–130° C.

$^1$H-NMR (CDCl$_3$): δ=7.45–7.35 (m,2H), 7.25–7.15 (m,2H), 6.95–6.85 (m,2H), 6.75 (d,1H), 6.40–6.35 (brt, 1H), 6.30 (d,1H), 5.65 (d,1H), 3.85 (s,3H), 3.70–3.60 (t,2H), 2.95–2.80 (t,2H), 1.45 (s,6H) ppm.

PREPARATION 55

(3S,4R)-4-Amino-3,4-dihydro-6-(1-[3-ethoxycarbonylprop-1-yl]-1H-tetrazol-5-yl)-3-hydroxy-2,2,3-trimethyl-2H-benzo[b]pyran

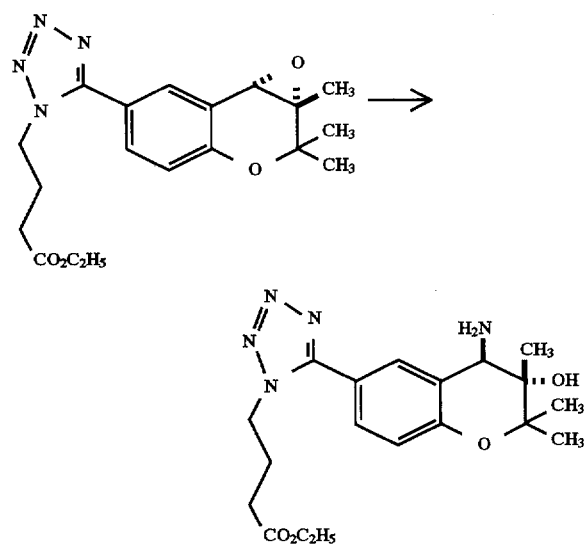

A mixture containing the compound of Preparation 1 (1 g), concentrated aqueous ammonia (4 ml) and ethanol (10 ml) was heated at 60°–65° C. for 18 hours then concentrated in vacuo and the residue was purified by chromatography on silica eluting with dichloromethane containing methanol (5%). The product-containing fractions were combined and concentrated in vacuo to give the title compound as a foam, 0.56 g. Found: C, 58.28; H, 7.03; N, 17.66; C$_{19}$H$_{27}$N$_5$O$_4$ requires: C, 58.57; H, 6.98; N, 17.97%.

$^1$H-NMR (CDCl$_3$): δ=7.85 (s,1H), 7.55–7.50 (dd,1H), 6.95–6.90 (d,1H), 4.55–4.40 (m,2H), 4.15–4.05 (q,2H), 3.95 (s,1H), 2.50–2.40 (m,2H), 2.30–2.20 (m,2H), 1.85–1.60 (brs,2H), 1.50 (s,3H), 1.35 (s,3H), 1.25–1.20 (t,3H), 1.05 (s,3H) ppm.

PREPARATION 56

(3R,4R/3S,4S)-3,4-Dihydro-2,2-dimethyl-3,4-epoxy-6-(1-[2-methoxyethyl]-1H-tetrazol-5-yl)-2H-benzo[b]pyran

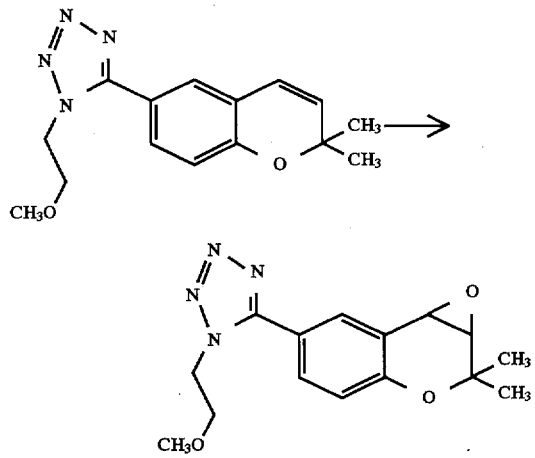

A solution of OXONE™ (3.5 g) in water (15 ml) was added, over 1 hour, to a stirred mixture of the compound of Preparation 57 (1.65 g), sodium hydrogen carbonate (2 g), water (15 ml) and acetone (45 ml). When the addition was complete the mixture was stirred at room temperature for a further 15 minutes then a second batch of OXONE™ (1.7 g in 5 ml water) was added. The acetone was evaporated in vacuo and the resulting aqueous mixture was extracted with dichloromethane (3×100 ml). The combined dichloromethane extracts were dried (Na$_2$SO$_4$) then concentrated in vacuo to give the title compound as an oil, 1.7 g.

$^1$H-NMR (CDCl$_3$): δ=7.90 (d,1H), 7.75–7.70 (dd,1H), 6.95–6.90 (d,1H), 4.55–4.45 (m,2H), 4.00–3.90 (m,3H), 3.–55 (d,1H), 3.30 (s,3H), 1.65 (s,3H), 1.30 (s,3H) ppm.

PREPARATION 57

2,2-Dimethyl-6-(1-[2-methoxyethyl]-1H-tetrazol-5-yl)-2H-benzo[b]pyran

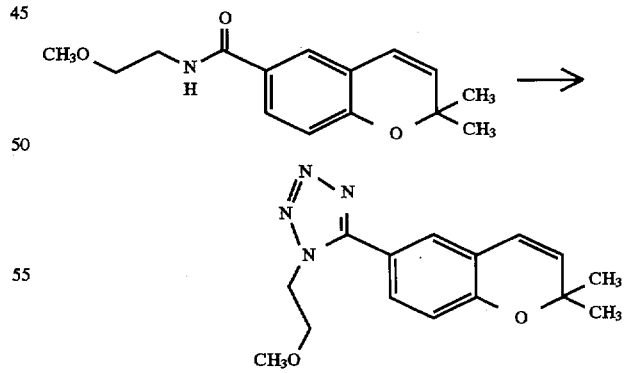

Phosphorus pentachloride (2.6 g) was added to a solution of the compound of Preparation 58 (3.2 g) in chloroform (75 ml) and the mixture was heated under reflux for 15 minutes. On cooling to room temperature trimethylsilyl azide (1.4 g) was added and the mixture was allowed to stand at room temperature for 16 hours. The mixture was washed with water (100 ml) dried (MgSO$_4$) and concentrated in vacuo to give an oil which was purified by chromatography on silica eluting with dichloromethane containing methanol (1%). The product-containing fractions were combined and concentrated in vacuo to give the title compound as an oil, 3.16 g.

¹H-NMR (CDCl₃): δ=7.55–7.50 (dd,1H), 7.45 (d,1H), 6.90 (d,1H), 6.40–6.35 (d,1H), 5.70 (d,1H), 4.55–4.50 (t,2H), 3.95–3.90 (t,2H), 3.30 (s,3H), 1.45 (s,6H) ppm.

PREPARATION 58

2,2-Dimethyl-6-(N-[2-methoxyethyl]carbamoyl)-2H-benzo[b]pyran

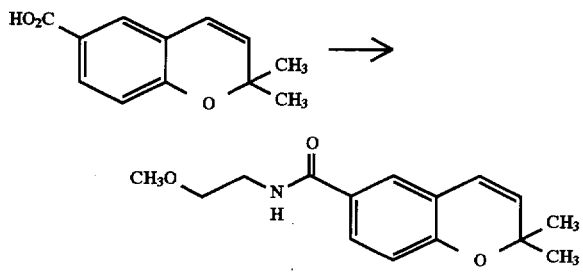

1,1'-Carbonyldiimidazole (2.62 g) was added to a solution of the compound of Preparation 27 (3 g) in dichloromethane (60 ml) and the mixture was stirred for 30 minutes at room temperature. 1-Amino-2-methoxyethane (1.1 g) was added and the mixture allowed to stand at room temperature for 48 hours. A further batch of 1-amino-2-methoxyethane (1 g) was added and stirring was continued for 24 hours. The mixture was washed with 10% aqueous sodium hydroxide (50 ml), 2N hydrochloric acid (2×50 ml) and water (50 ml), then concentrated in vacuo to give an oil which was purified by chromatography on silica eluting with dichloromethane containing methanol (1%). The product-containing fractions were combined and concentrated in vacuo to give the title compound as an oil which crystallised on standing, 3.32 g, m.p. 57°–60° C.

¹H-NMR (CDCl₃): δ=7.55–7.50 (dd,1H), 7.45 (d,1H), 6.80–6.75 (d,1H), 6.50–6.40 (brs,1H), 6.35–6.30 (d,1H), 5.65–5.60 (d,1H), 3.65–3.50 (m,4H), 3.40 (s,3H), 1.45 (s,6H) ppm.

PREPARATION 59

(3R,4S/3S,4R)-3,4-Dihydro-2,2-dimethyl-3-hydroxy-4-(2-oxo-1,2-dihydropyridin-1-yl)-6-(1H-tetrazol-5-yl)-2H-benzo[b]pyran

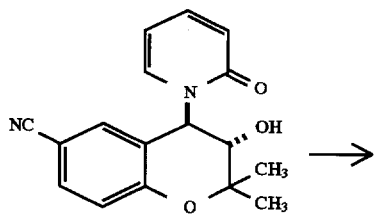

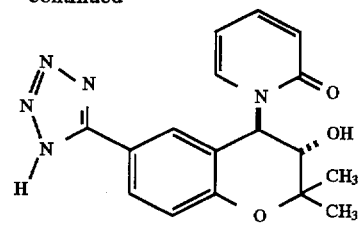

(only one stereoisomer shown)

A mixture containing (3R,4S/3S,4R)-6-cyano-3,4-dihydro-2,2-dimethyl-3-hydroxy-4-(2-oxo-1,2-dihydropyridin-1-yl)-2H-benzo[b]pyran (see J. Med. Chem., 1990, 33, 3028, and J. Med. Chem., 1990, 33, 492) (1 g), sodium azide (1 g), triethylamine hydrochloride (1.2 g) and 1-methyl-2-pyrrolidinone (10 ml) was heated at 150° C. for 2 hours. On cooling to room temperature the mixture was poured into water (100 ml), basified with 10% aqueous sodium hydroxide and extracted with dichloromethane (2×50 ml). The aqueous solution was filtered and then acidified with concentrated hydrochloric acid (CAUTION! HN₃ evolved). The resulting precipitate was filtered off and washed with water to give the title compound as a solid, 1 g, m.p. >260° C. Found: C, 58.83; H, 5.10; N, 19.99; C₁₇H₁₇N₅O₃.0.5H₂O requires: C, 58.61; H, 5.21; N, 20.10%.

¹H-NMR (d₆-DMSO): δ=7.90–7.80 (m,1H), 7.80–7.70 (d,0.5H), 7.50–7.35 (m,2H), 7.30 (s,0.5H), 7.05–7.00 (d,0.67H), 7.00–6.95 (d,0.33H), 6.55–6.50 (d,0.5H), 6.35–6.30 (t,0.5H), 6.30–6.15 (m,1.5H), 5.85–5.70 (brs,1H), 4.95–4.90 (d,0.25H), 4.50–4.45 (d,0.25H), 4.00–3.90 (d,1H), 0.60–3.10 (brs), 1.45 (s,2H), 1.40 (s,1H), 1.25 (s,2H), 1.20 (s,1H) ppm.

PREPARATION 60

(3R,4S/3S,4R)-3,4-Dihydro-2,2-dimethyl-3-hydroxy-4-(2-oxopiperidin-1-yl)-6-(1H-tetrazol-5-yl)-2H-benzo[b]pyran

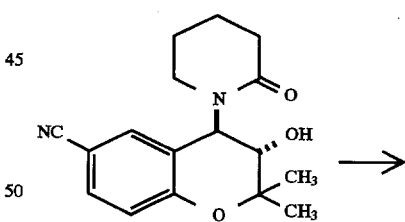

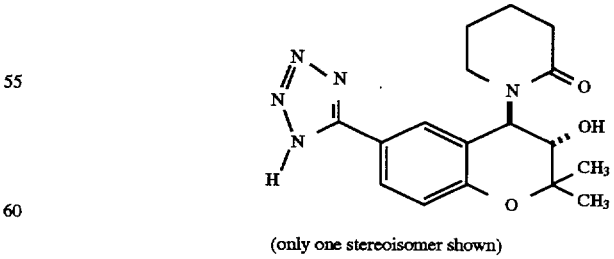

(only one stereoisomer shown)

A mixture containing (3R,4S/3S,4R)-6-cyano-3,4-dihydro-2,2-dimethyl-3-hydroxy-4-(2-oxopiperidin-1-yl)-2H-benzo[b]pyran (see J. Med. Chem., 1986, 29, 2194) (0.5 g), sodium azide (0.5 g), triethylamine hydrochloride (0.6 g)

and 1-methyl-2-pyrrolidinone (5 ml) was heated at 150° C. for 2 hours. On cooling to room temperature the mixture was partitioned between ethyl acetate (50 ml) and 5% aqueous sodium hydroxide (30 ml). The layers were separated and the aqueous layer was further extracted with ethyl acetate (2×20 ml). The aqueous solution was filtered and acidified to pH1 with concentrated hydrochloric acid (CAUTION: HN₃ evolved). The resulting precipitate was triturated with hot ethanol containing a few drops of water, then filtered and dried in vacuo to give the title compound as a solid, 0.4 g, m.p. >295° C.

¹H-NMR (d₆-DMSO): δ =7.85–7.75 (d,1H), 7.55 (s,1H), 6.95–6.90 (d,1H), 5.80–5.70 (d,1H), 5.60–5.55 (d,1H), 3.75–3.65 (m,1H), 3.30–3.25 (brs,1H), 3.15–3.10 (brt, 1H), 2.75–2.65 (m,1H), 2.50–2.40 (m,2H), 1.85–1.65 (m,3H), 1.60–1.50 (m,1H), 1.45 (s,3H), 1.15 (s,3H) ppm.

PREPARATION 61

(3R,4S/3S,4R)-3,4-Dihydro-2,2-dimethyl-3-hydroxy-4-(2-oxopiperidin-1-yl)-6-(1H-tetrazol-5-yl)-2H-benzo[b]pyran

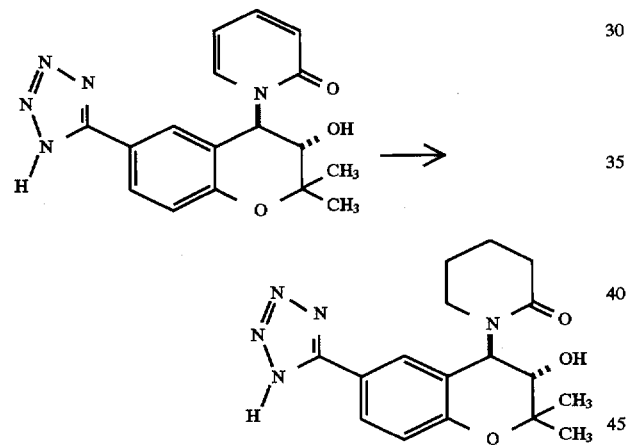

(only one stereoisomer shown)

10% Aqueous sodium hydroxide (5 ml) was added to a solution of the compound of Preparation 59 (5.8 g) in water (200 ml) and then 10% palladium-on-carbon (1 g) was added. The mixture was hydrogenated at room temperature and 345 kPa (50 psi) for 25 hours, then filtered through a cellulose-based filter aid. The filtrate was acidified to pH1 with concentrated hydrochloric acid to give the title compound as a solid which was filtered off and dried in vacuo, 5.3 g.

¹H-NMR (d₆-DMSO): δ=7.85–7.80 (d,1H), 7.55 (s,1H), 6.95–6.90 (d,1H), 5.80–5.70 (d,1H), 5.65–5.50 (brs,1H), 3.75–3.65 (d,1H), 3.20–3.05 (m,1H), 2.75–2.65 (m,1H), 2.55–2.35 (m,3H), 1.85–1.65 (m,3H), 1.60–1.45 (m,1H), 1.45 (s,3H), 1.15 (s,3H) ppm.

PREPARATION 62

(3R,4R/3S,4S)-3,4-Dihydro-2,2-dimethyl-3,4-epoxy-6-(1-[-2-phenylethyl]-1H-tetrazol-5-yl)-2H-benzo[b]pyran

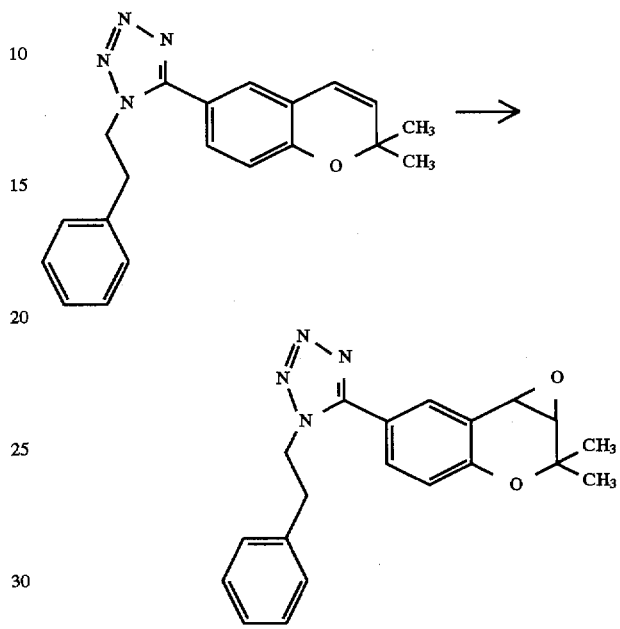

A solution of OXONE™ (8.75 g) in water (35 ml) was added, over 45 minutes, to a stirred mixture of the compound of Preparation 63 (4.5 g), sodium hydrogen carbonate (5.7 g), water (35 ml) and acetone (100 ml). When the addition was complete the mixture was stirred at room temperature for 16 hours. The acetone was evaporated in vacuo and the resulting aqueous mixture was extracted with ethyl acetate (2×100 ml). The ethyl acetate solution was dried (MgSO₄), then concentrated in vacuo to give the title compound, 4.6 g.

¹H-NMR (CDCl₃): δ=7.35–7.20 (m,4H), 7.15–7.10 (m,1H), 7.00–6.95 (m,2H), 6.85–6.80 (d,1H), 4.65–4.55 (m,2H), 3.85 (d,1H), 3.55 (d,1H), 3.30–3.25 (t,2H), 1.60 (s,3H), 1.30 (s,3H) ppm.

PREPARATION 63

2,2-Dimethyl-6-(1-[2-phenylethyl]-1H-tetrazol-5-yl)-2H-benzo[b]pyran

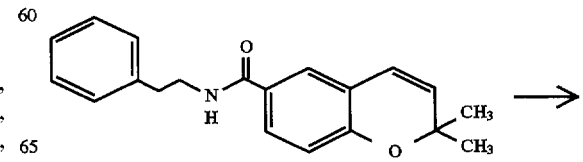

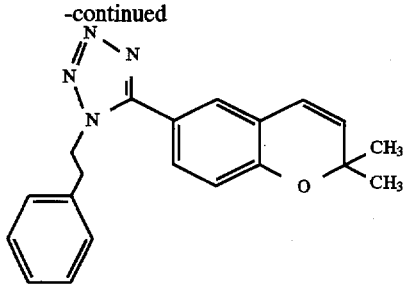

Phosphorus pentachloride (5 g) was added to a solution of the compound of Preparation 64 (8.2 g) in chloroform (100 ml) and the mixture was heated under reflux for 25 minutes. On cooling to 0° C. trimethylsilyl azide (3.2 ml) was added and the mixture was allowed to stand at room temperature for 3 days. Further trimethylsilyl azide (0.8 ml) was added and the mixture was stirred at room temperature for 5 hours. The mixture was washed with water (2×100 ml) and the organic layer was dried (MgSO$_4$) then concentrated in vacuo in give an oil which was purified by chromatography on silica eluting with dichloromethane containing methanol (1%). The product-containing fractions were combined and concentrated in vacuo to give a gum which was further purified by chromatography on silica eluting with toluene containing ethyl acetate (5%). The product-containing fractions were combined and concentrated in vacuo to give the title compound, 6 g.

$^1$H-NMR (CDCl$_3$): δ=7.30–7.15 (m,3H), 7.05–6.95 (m,3H), 6.85–6.75 (m,2H), 6.25–6.20 (d,1H), 5.70–5.65 (d,1H), 4.65–4.55 (t,2H), 3.30–3.20 (t,2H), 1.45 (s,6H) ppm.

PREPARATION 64

2,2-Dimethyl-6-(N-[2-phenylethyl]carbamoyl)-2H-benzo[b]pyran

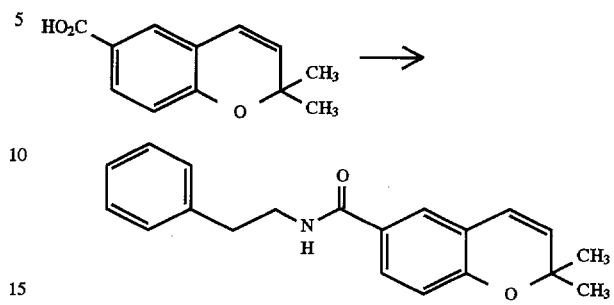

1,1'-Carbonyldiimidazole (4.1 g) was added to a solution of the compound of Preparation 27 (5 g) in dichloromethane (40 ml) and the mixture was stirred at room temperature for 30 minutes. 2-Phenylethylamine (4.2 ml) was added and the mixture was stirred at room temperature for 16 hours. The mixture was diluted with dichloromethane to a total volume of 100 ml then washed sequentially with 2N hydrochloric acid (2×50 ml), 10% aqueous sodium hydroxide (50 ml), water (50 ml) and, finally, 2N hydrochloric acid (2×50 ml), then dried (MgSO$_4$) and concentrated in vacuo to give the title compound, 8 g.

$^1$H-NMR (CDCl$_3$): δ=7.45–7.15 (m,7H), 6.80–6.75 (d,1H), 6.35–6.30 (d,1H), 6.10–6.05 (brs,1H), 5.65–5.60 (d,1H), 3.70–3.65 (q,2H), 2.95–2.90 (t,2H), 1.45 (s,6H) ppm.

PREPARATION 65

(3S,4S)-3,4-Dihydro-3,4-epoxy-6-(1-[4-ethoxycarbonylbut-1-yl]-1H-tetrazol-5-yl)-2,2,3-trimethyl-2H-benzo[b]pyran

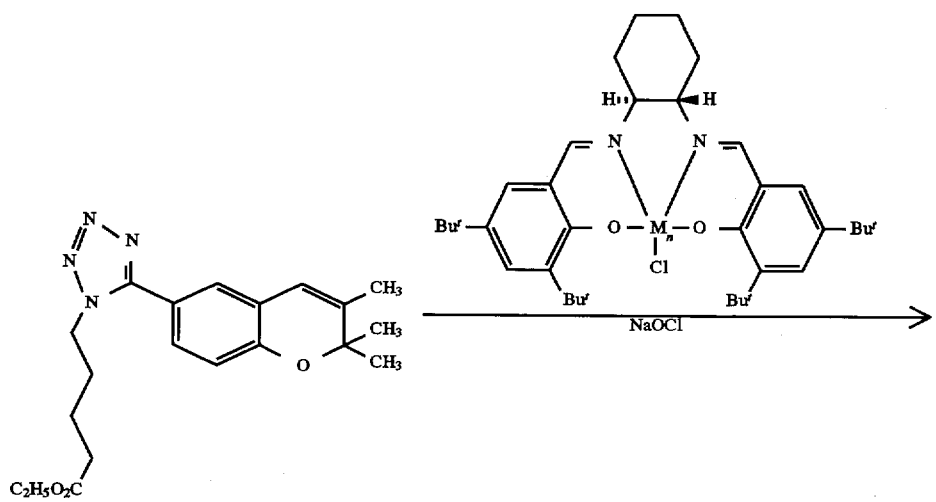

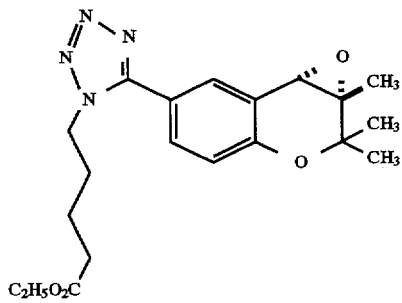

A solution of 4M commercial bleach (30 ml) was diluted to a volume of 72 ml with 0.05M aqueous sodium hydrogen phosphate solution and the pH of the mixture was adjusted to 11.3 with 5N aqueous sodium hydroxide solution. A portion of the resulting solution (51 ml) was cooled to 0° C. in an ice bath and a solution of the compound of Preparation 66 (5.6 g) and [(S,S)-1,2-bis(3,5-di-tert-butylsalicylideamino]cyclohexane manganese III chloride (see J. Amer. Chem. Soc., 1991, 113, 7063) (0.527 g) in dichloromethane (25 ml) was added. The resulting mixture was stirred at 0° C. for 20 hours then the layers were separated and the dichloromethane layer was washed with saturated aqueous sodium chloride solution (20 ml), dried (MgSO₄) and concentrated in vacuo. The residual gum was purified by chromatography on silica eluting initially with hexane containing dichloromethane (5%) and then with hexane containing ethyl acetate (5% up to 20%). The product-containing fractions were combined and concentrated in vacuo to give the title compound, 3.72 g.

¹H-NMR (CDCl₃): δ=7.65 (d,1H), 7.50–7.45 (dd,1H), 6.95–6.90 (d,1H), 4.45–4.35 (t,2H), 4.10–4.00 (q,2H), 3.75 (s,1H), 2.30–2.25 (t,2H), 2.00–1.90 (m,2H), 1.65–1.55 (m,2H), 1.55 (s,3H), 1.50 (s,3H), 1.30 (s,3H), 1.25–1.15 (t,3H) ppm.

PREPARATION 66

6-(1-[4-Ethoxycarbonylbut-1-yl]-1H-tetrazol-5-yl)-2,2,3-trimethyl-2H-benzo[b]pyran

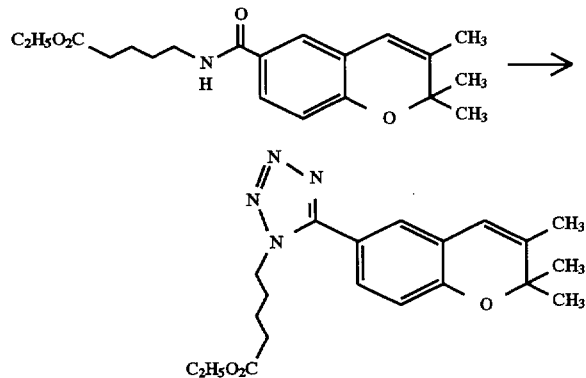

Phosphorus pentachloride (4.58 g) was added to a solution of the compound of Preparation 67 (7.1 g) in chloroform (90 ml) and the mixture was heated under reflux for 15 minutes. On cooling to room temperature trimethylsilyl azide (3.32 g) was added and the mixture was stirred at room temperature for 16 hours. Water (50 ml) was added and the mixture was vigorously stirred. The layers were separated and the chloroform solution was washed with saturated aqueous sodium chloride solution (50 ml) and 10% aqueous sodium carbonate solution (50 ml), then dried (MgSO₄) and concentrated in vacuo. The residue was chromatographed on silica eluting with dichloromethane containing methanol (5%). The product-containing fractions were combined and concentrated in vacuo to give the title compound, 5.7 g.

¹H-NMR (CDCl₃): δ=7.30–7.25 (dd,1H), 7.20 (d,1H), 6.90–6.85 (d,1H), 6.10 (s,1H), 4.45–4.35 (t,2H), 4.10 (q,2H), 2.30–2.25 (t,2H), 2.00–1.90 (m,2H), 1.85 (brs,3H), 1.70–1.55 (m,2H), 1.40 (s,6H), 1.25–1.15 (t,3H) ppm.

PREPARATION 67

6-(N-[4-Ethoxycarbonylbut-1-yl]carbamoyl)-2,2,3-trimethyl-2H-benzo[b]pyran

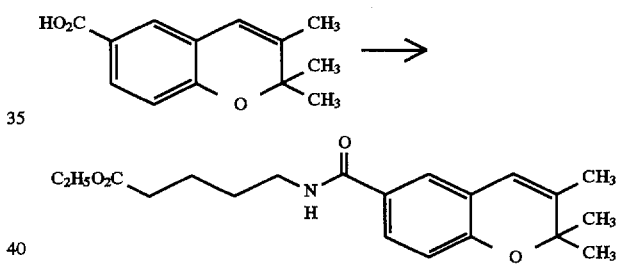

Oxalyl chloride (10 ml) was added to a solution of the compound of Preparation 4 (7.5 g) in dichloromethane (100 ml). Anhydrous N,N-dimethylformamide (1 drop) was added and the mixture was heated under reflux for 30 minutes then allowed to cool to room temperature and concentrated in vacuo. The residue was azeotroped with dichloromethane (3×100 ml) and the resulting residue was dissolved in dichloromethane (50 ml) and added, dropwise, to a cooled (0° C.) solution of ethyl 5-aminopentanoate hydrochloride (6.9 g) and N,N-diisopropylethylamine (13.4 g) in dichloromethane (150 ml). The resulting mixture was stirred at room temperature for 16 hours then water (100 ml) was added and the layers were separated. The dichloromethane layer was washed with saturated aqueous sodium chloride solution (100 ml), dried (MgSO₄) and concentrated in vacuo to give a gum which was purified by chromatography on silica eluting with dichloromethane containing methanol (2%) and concentrated aqueous ammonia (0.3%). The product-containing fractions were combined and concentrated in vacuo to give the title compound, 7.2 g.

¹H-NMR (CDCl₃): δ=7.50–7.45 (dd,1H), 7.35 (d,1H), 6.75–6.70 (d,1H), 6.55–6.50 (brt, 1H), 6.05 (s,1H), 4.10–4.05 (q,2H), 3.45–3.35 (q,2H), 2.35–2.25 (t,2H), 1.80 (s,3H), 1.70–1.55 (m,4H), 1.40 (s,6H), 1.25–1.15 (t,3H) ppm.

PREPARATION 68

(3S,4R)-4-Amino-3,4-dihydro-6-(1-[4-ethoxycarbonylbut-1-yl]-1H-tetrazol-5-yl)-3-hydroxy-2,2,3-trimethyl-2H-benzo[b]pyran

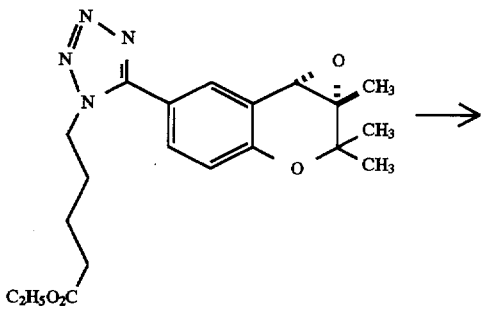

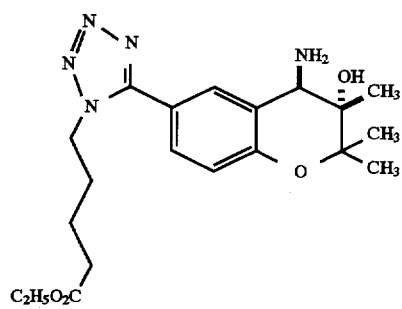

A mixture containing the compound of Preparation 65 (0.5 g), concentrated aqueous ammonia (3 ml) and ethanol (6 ml) was heated at 60° C. for 20 hours. Further concentrated aqueous ammonia 2 ml) was added and heating was continued for 24 hours. The mixture was concentrated in vacuo and the residue was purified by chromatography on silica eluting with dichloromethane containing methanol (2%) and concentrated aqueous ammonia (0.3%). The product-containing fractions were combined and concentrated in vacuo to give the title compound, 0.36 g.

$^1$H-NMR (CDCl$_3$): δ=7.80 (s,1H), 7.65-7.55 (dd,1H), 6.95-6.90 (d,1H), 4.40-4.30 (t,2H), 4.10-4.00 (q,2H), 4.00-3.95 (s,1H), 2.30-2.25 (t,2H), 2.10-1.90 (m,2H), 2.05-1.55 (brs,2H), 1.65-1.55 (m,2H), 1.50 (s,3H), 1.30 (s,3H), 1.25-1.20 (t,3H), 1.10 (s,3H) ppm.

PREPARATION 69

(3S,4R)-6-(1-Carboxymethyl-1H-tetrazol-5-yl)-3,4-dihydro-3-hydroxy-4-(3-hydroxypyridazin-6-yl)oxy-2,2,3-trimethyl-2H-benzo[b]pyran

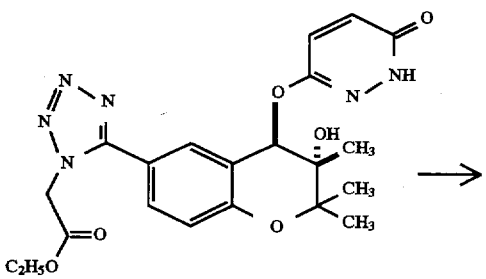

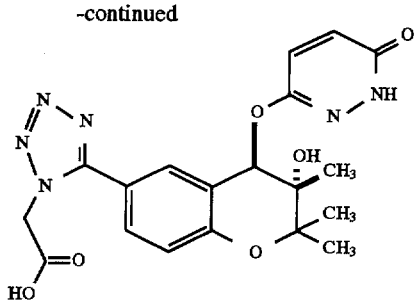

A mixture containing the compound of Example 4 (0.23 g), 0.35N aqueous sodium hydroxide solution (3 ml) and ethanol (3 ml) was stirred at room temperature for 4 hours then concentrated in vacuo. The residue was extracted with ethyl acetate (50 ml). The ethyl acetate extract was washed with water (50 ml), dried (MgSO$_4$) and concentrated in vacuo to give the title compound as a foam, 0.14 g, m.p. 210° C. (dec.).

$^1$H-NMR (CDCl$_3$/d$_6$-DMSO): δ=7.65-7.55 (dd,1H), 7.50 (s, 1H), 7.10-7.05 (d,1H), 7.00-6.90 (m,2H), 5.95 (s,1H), 5.10-4.95 (ABq,2H), 2.00 (m,2H), 1.45 (s,3H), 1.40 (s,3H), 1.30 (s,3H) ppm.

PREPARATION 70

5-(2-Methanesulphonyloxyethyl)-1,3-benzodioxolane

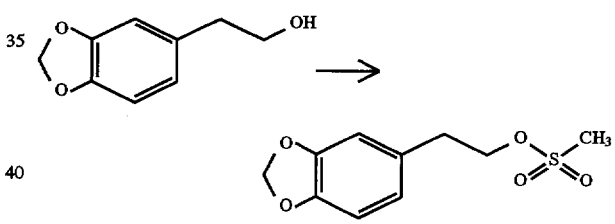

A solution of methanesulphonyl chloride (7.6 g) in dichloromethane (25 ml) was added, over 15 minutes, to a cooled (−5° C.) solution of triethylamine (6.7 g) and the compound of Preparation 71 (10 g) in dichloromethane (75 ml). The mixture was stirred at 0° C. for 1 hour then poured into water (100 ml). The layers were separated and the aqueous layer was extracted with dichloromethane (50 ml). The combined dichloromethane layers were washed with water (100 ml) then dried (MgSO$_4$) and concentrated in vacuo to give the title compound as an oil, 15.3 g.

$^1$H-NMR (CDCl$_3$): δ=6.80-6.65 (m,3H), 5.95 (s,2H), 4.40-4.30 (t,2H), 3.00-2.95 (t,2H), 2.90 (s,3H) ppm.

PREPARATION 71

5-(2-Hydroxyethyl)-1,3-benzodioxolane

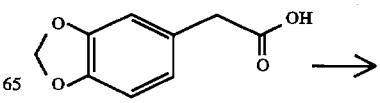

-continued

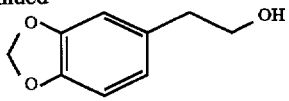

5-Carboxymethyl-1,3-benzodioxolane (18 g) was added, in portions over 30 minutes, to a stirred, ice-cooled (0° C.) suspension of lithium aluminium hydride (4 g) in diethyl ether (400 ml). The mixture was stirred at room temperature for 2 hours then quenched by the cautious addition of saturated aqueous ammonium chloride solution. The mixture was filtered and the filtrate was washed with 10% aqueous sodium carbonate solution then dried (MgSO$_4$) and concentrated in vacuo to give the title compound as an oil, 15.01 g.

$^1$H-NMR (CDCl$_3$): δ=6.69–6.83 (m,3H), 5.98 (s,2H), 3.82 (dt,2H), 2.81 (t,2H), 1.44 (t,1H) ppm.

PREPARATION 72

(3R,4R/3S,4S)-3,4-Dihydro-2,2-dimethyl-3,4-epoxy-6-(1-ethoxycarbonylmethyl-1H-tetrazol-5-yl)-2H-benzo[b]pyran

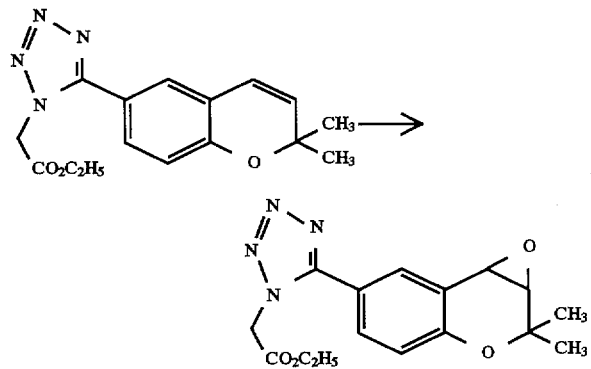

A solution of OXONE™ (3.1 g) in water (12 ml) was added, over 1.5 hours, to a stirred mixture of the compound of Preparation 73 (1.6 g), sodium hydrogen carbonate (1.6 g), water (12 ml) and acetone (40 ml). When the addition was complete the mixture was stirred at room temperature for 30 minutes. The acetone was evaporated in vacuo and the resulting aqueous mixture was extracted with dichloromethane (2×100 ml). The combined dichloromethane extracts were dried (MgSO$_4$) then concentrated in vacuo to give the title compound as a foam, 1.4 g.

$^1$H-NMR (CDCl$_3$): δ=7.70 (d,1H), 7.50–7.45 (dd,1H), 6.95–6.90 (d,1H), 5.15 (s,2H), 4.30–4.20 (q,2H), 3.95 (d,1H), 3.55 (d,1H), 1.65 (s,3H), 1.30 (s,3H), 1.30–1.20 (t,3H) ppm.

PREPARATION 73

2,2-Dimethyl-6-(1-ethoxycarbonylmethyl-1H-tetrazol-5-yl)-2H-benzo[b]pyran

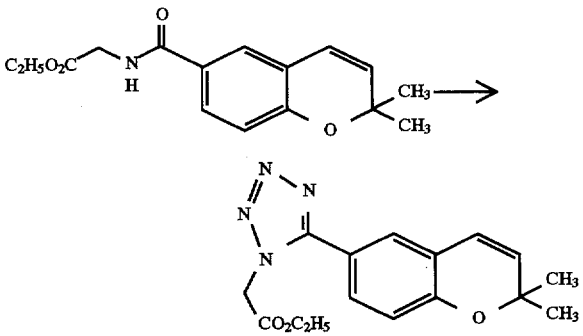

Phosphorus pentachloride (1.1 g) was added to a solution of the compound of Preparation 74 (1.5 g) in chloroform (30 ml) and the mixture was heated under reflux for 15 minutes. On cooling to room temperature trimethylsilyl azide (0.9 g) was added and the mixture was allowed to stand at room temperature for 4 days. The mixture was washed with water (100 ml), dried (MgSO$_4$) and concentrated in vacuo to give the title compound as an oil, 1.7 g.

$^3$H-NMR (CDCl$_3$): δ=7.35–7.30 (m,2H), 6.90–6.85 (d,1H), 6.35–6.30 (d,1H), 5.75–5.70 (d,1H), 5.15 (s,2H), 4.30–4.20 (q,2H), 1.45 (s,6H), 1.30–1.20 (t,3H) ppm.

PREPARATION 74

2,2-Dimethyl-6-(N-ethoxycarbonylmethylcarbamoyl)-2H-benzo[b]pyran

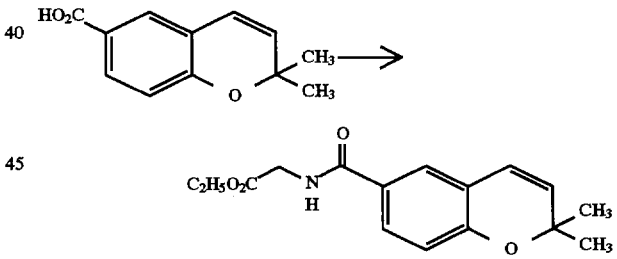

1,1'-Carbonyldiimidazole (4.4 g) was added to a solution of the compound of Preparation 27 (5 g) in dichloromethane (100 ml) and the mixture was stirred at room temperature for 30 minutes. Triethylamine (3 g) was added followed by ethyl glycinate hydrochloride (3.8 g) and the mixture was allowed to stand at room temperature for 2 days. The mixture was washed with water (100 ml) and concentrated in vacuo to give a gum which was purified by chromatography on silica eluting with dichloromethane containing methanol (1.25%). The product-containing fractions were combined and concentrated in vacuo to give the title compound as an oil which crystallised on standing, 7.5 g.

$^1$H-NMR (CDCl$_3$): δ=7.60–7.55 (dd,1H), 7.50 (d,1H), 6.80–6.75 (d,1H), 6.60–6.50 (brt,1H), 6.35–6.30 (d,1H), 5.65–5.60 (d,1H), 4.30–4.15 (m,4H), 1.45 (s,6H), 1.30–1.25 (t,3H) ppm.

PREPARATION 75

2-(4-Fluorophenyl)ethyl Iodide

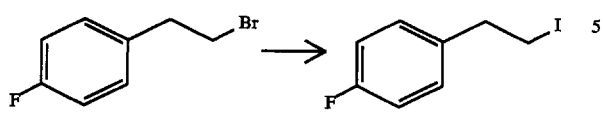

A mixture containing 2-(4-fluorophenyl)ethyl bromide (see Preparation 76) (10 g), sodium iodide (10 g) and acetone (200 ml) was stirred at room temperature for 20 hours then filtered. The filtrate was concentrated in vacuo to give the title compound as a colourless oil, 12 g.

$^1$H-NMR (CDCl$_3$): δ=7.20–7.10 (m,2H), 7.05–6.95 (m,2H), 3.35–3.30 (t,2H), 3.20–3.10 (t,2H) ppm.

PREPARATION 76

2-(4-Fluorophenyl)ethyl Bromide

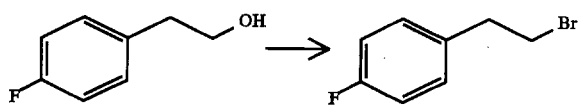

Phosphorus tribromide (14 g) was added, over 2 minutes, to a solution of 2-(4-fluorophenyl)ethanol (14 g) in carbon tetrachloride (80 ml). The mixture was heated under reflux for 2 hours then cooled in an ice bath. 10% Aqueous sodium carbonate solution was added until all of the solid has dissolved. The mixture was transferred to a separating funnel and the layers were separated. The aqueous layer was extracted with dichloromethane (50 ml) and the organic solutions were combined, dried (MgSO$_4$) and concentrated in vacuo. The residue was purified by chromatography on silica eluting with 1:1 hexane/dichloromethane. The product-containing fractions were combined and concentrated in vacuo to give the title compound as a colourless oil, 10 g.

$^1$H-NMR (CDCl$_3$): δ=7.30–7.20 (m,2H), 7.10–7.00 (m,2H), 3.65–3.55 (t,2H), 3.25–3.15 (t,2H) ppm.

PREPARATION 77

Chloromethyl Ethyl Carbonate

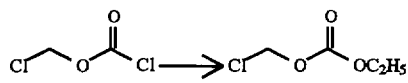

Ethanol (1.9 ml) was added in one portion to a cooled (0° C.) solution of chloromethyl chloroformate (4.2 g) in dichloromethane (20 ml). Pyridine (2.63 ml) was then added (CAUTION! EXOTHERMIC) and the mixture was allowed to warm to room temperature and stirred for 2 hours. The mixture was diluted with dichloromethane (100 ml), washed with ice-cold (0° C.) 0.5M hydrochloric acid then dried (MgSO$_4$) and concentrated in vacuo to give the title compound as an oil, 0.17 g.

$^1$H-NMR (CDCl$_3$): δ=5.70 (s,2H), 4.30–4.20 (q,2H), 1.35–1.25 (t,3H) ppm.

PREPARATION 78

6-Bromo-2,3-dihydro-2,2,3-trimethyl-4H-benzo[b]pyran-4-one

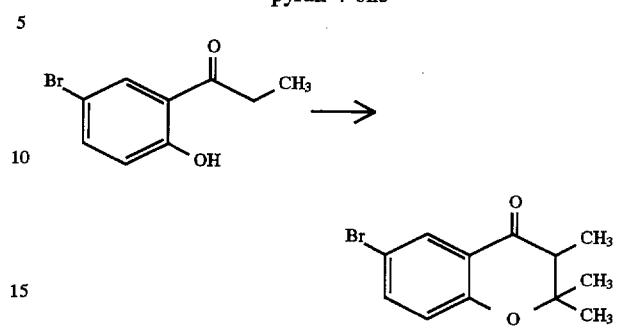

The compound of Preparation 79 (1.46 kg) was dissolved in a mixture of acetone (7.30 l) and xylene (6.57 l) and piperidine (3.04 kg) was added. The solution obtained was heated under reflux for 5 days, cooled, washed with water (2×3.0 l), 2N aqueous hydrochloric acid solution (2×5.0 l), 2N aqueous sodium hydroxide solution (1×3.0 l) and water (2×3.0 l). The organic layer was dried and concentrated under reduced pressure to provide the title compound as a brown oil (1.458 kg).

PREPARATION 79

4-Bromo-2-propanoylphenol

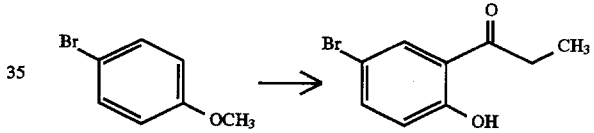

Aluminium chloride (3.747 kg) was added to dichloromethane (7.0 l) at room temperature and propionyl chloride (1.297 kg) was then added over a 10 minute period. The mixture was stirred for 45 minutes and then a solution of 4-bromoanisole (1.312 kg) in dichloromethane (0.87 l) was added over a 15 minute period. The mixture was heated under reflux for 6.5 hours and then kept overnight at room temperature. The ice-cooled reaction mixture was quenched by the slow addition of ice (15 kg) over 1.5 hours. The mixture obtained was stirred for 15 minutes, the layers were separated and the aqueous layer extracted with dichloromethane (2×1.0 l). The organic layers were combined and washed with water (2×2.0 l), then two-thirds of the solvent removed by distillation at atmospheric pressure. Methanol (5.63 l) was then added slowly and the distillation continued until a pot temperature of 64° C. and a head temperature of 62° C. was achieved. Water (0.4 l) was added slowly and the mixture was cooled resulting in the precipitation of an off-white solid. Further water (0.4 l) was then added slowly and the precipitated solid granulated at about 10° C. for 2 hours. The solid was then filtered off, washed sparingly with a 6:1 methanol/water mixture and dried under reduced pressure at 50° C. to provide the title compound (1.464 kg).

PHARMACOLOGICAL DATA

A selection of the compounds of the preceding Examples was tested for smooth muscle relaxant activity by the method involving measuring the in vitro relaxation of guinea pig tracheal ring preparations as described on pages 31 and 32 of the description. The results are shown in the Table below.

TABLE

| Compound of Example No. | IC$_{50}$(μM) |
|---|---|
| 3 | 0.15 |
| 7 | 0.44 |
| 11 | 0.12 |
| 35 or 56 | 0.04 |
| 36 | 0.068 |

We claim:
1. A compound of the formula:

or a pharmaceutically acceptable salt thereof,
wherein the dashed line represents an optional covalent bond;

X is O, NH, S or a direct link;

R and $R^1$ are either each independently selected from H, fluoro($C_1$–$C_4$)alkyl and $C_1$–$C_4$ alkyl or taken together represent $C_2$–$C_6$ alkylene;

$R^2$ is H or $C_1$–$C_4$ alkyl;

$R^3$ is hydroxy when the dashed line does not represent a covalent bond and $R^3$ is absent when the dashed line represents a covalent bond;

$R^4$ is (a), when X is O, a group of the formula:

wherein W and $W^1$ taken together represent $C_1$–$C_4$ alkylene, said alkylene being optionally benzo-fused when W and $W^1$ taken together represent $C_2$–$C_4$ alkylene, and optionally substituted, including in the benzo-fused portion, by $C_1$–$C_6$ alkyl, hydroxy, —$OR^8$, halo, —$N(R^8)_2$, —$SR^8$ or halo($C_1$–$C_4$)alkyl, (b), when X is O, NH or S, hydroxyphenyl optionally substituted by $C_1$–$C_6$ alkyl, —$OR^8$, halo, —$N(R^8)_2$, —$SR^8$ or halo($C_1$–$C_4$)alkyl, (c) a 4- to 7-membered heterocyclic ring containing either from 1 to 3 N hetero-atoms or one N hetero-atom and one O or one S hetero-atom, said ring being optionally benzo- or $C_3$–$C_7$ cycloalkyl-fused and optionally substituted, including in the benzo- or $C_3$–$C_7$ cycloalkyl-fused portion, by $C_1$–$C_6$ alkyl, hydroxy, hydroxy($C_1$–$C_4$)alkyl, —$OR^8$, $R^8O$($C_1$–$C_4$)alkyl, halo, halo($C_1$–$C_4$)alkyl, —$S(O)_mR^8$, $R^8S(O)_m$($C_1$–$C_4$)alkyl, oxo, N-cyanoimino, amino, amino($C_1$–$C_4$)alkyl, —$NHR^8$, $R^8NH$($C_1$–$C_4$)alkyl, —$N(R^8)_2$, $(R^8)_2N$($C_1$–$C_4$)alkyl, cyano, cyano ($C_1$–$C_4$)alkyl, —$CO_2R^8$, $R^8O_2C$($C_1$–$C_4$)alkyl, —$CONH_2$, $H_2NCO$($C_1$–$C_4$)alkyl, —$CONHR^8$, $R^8NHCO$($C_1$–$C_4$)alkyl, —$CON(R^8)_2$ or $(R^8)_2NCO$($C_1$–$C_4$)alkyl, or, as appropriate, a ring N- or S-oxide derivative of said heterocyclic ring, with the proviso that said heterocyclic ring is linked by a ring carbon atom when X is O, NH or S, or (d), when X is NH, a group of the formula:

wherein $R^6$ is —$OR^8$, —$NHR^8$, —$SR^8$, —NH(aryl) or —NH(pyridinyl) and $R^7$ is cyano, nitro or $C_2$–$C_6$ alkanoyl;

$R^5$ is aryl, $C_1$–$C_{12}$ alkyl, $C_2$–$C_{12}$ alkenyl or $C_2$–$C_{12}$ alkynyl, said $C_1$–$C_{12}$ alkyl, $C_2$–$C_{12}$ alkenyl and $C_2$–$C_{12}$ alkynyl being optionally substituted by $C_4$–$C_7$ cycloalkyl, hydroxy, —$OR^8$, $C_2$–$C_6$ alkanoyloxy, halo, cyano, nitro, amino, —$NHR^8$, —$N(R^8)_2$, —$S(O)_mR^8$, —$NHSO_2R^8$, —$NHCOR^8$, —$COR^8$, —$CONH_2$, —$CONHR^8$, —$CON(R^8)_2$, —$OCO_2R^8$, —CONH ($C_1$–$C_6$)alkyl$CO_2R^8$, —$CONR^8$($C_1$–$C_6$)alkyl$CO_2R^8$, —$CO_2R^9$, aryl, aryloxy, arylcarbonyl, arylcarbonyloxy, aryl($C_1$–$C_6$)alkoxy, aryl($C_1$–$C_6$)alkoxycarbonyl, phthalimido, or a group of the formula:

$R^8$ is $C_1C_6$ alkyl;

$R^9$ is indanyl, aryl, $C_1$–$C_{12}$ alkyl, $C_2$–$C_{12}$ alkenyl or $C_2$–$C_{12}$ alkynyl, said $C_1$–$C_{12}$, alkyl, $C_2$–$C_{12}$alkenyl and $C_2$–$C_{12}$ alkynyl being optionally substituted by $C_4$–$C_7$ cycloalkyl, hydroxy, —$OR^8$, $C_2$–$C_6$ alkanoyloxy, halo, cyano, nitro, amino, —$NHR^8$, —$N(R^8)_2$, —$S(O)_mR^8$, —$NHSO_2R^8$, —$NHCOR^8$, —$COR^8$, —$CONH_2$, —$CONHR^8$, —$CON(R^8)_2$, —$OCO_2R^8$, —CONH ($C_1$–$C_6$)alkyl$CO_2R^8$, —$CONR^8$($C_1$–$C_6$)alkyl$CO_2R^8$, —$CO_2$($C_1$–$C_{12}$ alkyl), aryl, aryloxy, arylcarbonyl, arylcarbonyloxy, aryl($C_1$–$C_6$)alkoxy, aryl($C_1$–$C_6$) alkoxycarbonyl, phthalimido, or a group of the formula:

"aryl", used in the definitions of $R^5$, $R^6$ and $R^9$ and in this definition, means phenyl optionally substituted by $C_1$–$C_6$ alkyl, $C_2$–$C_6$ alkenyl, $C_2$–$C_6$ alkynyl, hydroxy, hydroxy($C_1$–$C_6$)alkyl, —$OR^8$, $R^8O$($C_1$–$C_6$)alkyl, $R^8O$ ($C_1$–$C_6$)alkoxy, $R^8O$($C_1$–$C_6$)alkoxy($C_1$–$C_6$)alkyl, halo, halo($C_1$–$C_6$)alkyl, cyano, cyano($C_1$–$C_6$)alkyl, nitro, nitro($C_1$–$C_6$)alkyl, amino, amino($C_1$–$C_6$)alkyl, —$NHR^8$, $R^8NH$($C_1$–$C_6$)alkyl, —$N(R^8)_2$, $(R^8)_2N$ ($C_1$–$C_6$)alkyl, —$S(O)_mR^8$, $R^8S(O)_m$($C_1$–$C_6$)alkyl, —$NHCOR^8$, $R^8CONH$($C_1$–$C_6$)alkyl, —$COR^8$, $R^8CO$ ($C_1$–$C_6$)alkyl, —$CONH_2$, $H_2NCO$($C_1$–$C_6$)alkyl, —$CONHR^8$, $R^8NHCO$($C_1$–$C_6$)alkyl, —$CON(R^8)_2$, $(R^8)_2NCO$($C_1$–$C_6$)alkyl, —$CONH$($C_1$–$C_6$) alkyl$CO_2R^8$, $R^8O_2C$($C_1$–$C_6$)alkyl$NHCO$($C_1$–$C_6$)alkyl, —$CONR^8$($C_1$–$C_6$)alkyl$CO_2R^8$, $R^8O_2C$($C_1$–$C_6$) alkyl$NR^8CO$($C_1$–$C_6$)alkyl, —$CO_2R^{9A}$, $R^{9A}O_2C$ ($C_1$–$C_6$)alkyl, aryl, aryl($C_1$–$C_6$)alkyl, aryl($C_1$–$C_6$) alkoxy or aryl($C_1$–$C_6$)alkoxy($C_1$–$C_6$)alkyl;

$R^{9A}$ is indanyl, phenyl, $C_1$–$C_{12}$ alkyl, $C_2$–$C_{12}$ alkenyl or $C_2$–$C_{12}$alkynyl, said $C_1$–$C_{12}$ alkyl, $C_2$–$C_{12}$ alkenyl and $C_2$–$C_{12}$ alkynyl being optionally substituted as previously defined for those definitions for $R^9$ and said phenyl being optionally substituted by from 1 to 3 substituents each independently selected from $C_1$–$C_6$ alkyl, hydroxy, —$OR^8$, halo, halo($C_1$–$C_6$)alkyl, nitro and cyano;

m is 0, 1 or 2; and n is 1, 2 or 3.

2. A compound as claimed in claim 1 wherein

R and $R^1$ are either each independently selected from H and $C_1$–$C_4$ alkyl or taken together represent $C_1$–$C_6$ alkylene;

$R^4$ is (a), when X is O, a group of the formula:

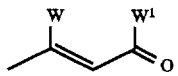

wherein W and $W^1$ taken together represent $C_1$–$C_4$ alkylene, said alkylene being optionally benzo-fused when W and $W^1$ taken together represent $C_2$–$C_4$ alkylene, and optionally substituted, including in the benzo-fused portion, by $C_1$–$C_6$ alkyl, hydroxy, —$OR^8$, halo, —$N(R^8)_2$, —$SR^8$ or halo($C_1$–$C_4$)alkyl, (b), when X is O, NH or S, hydroxyphenyl optionally substituted by $C_1$–$C_6$ alkyl, —$OR^8$, halo, —$N(R^8)_2$, —$SR^8$ or halo($C_1$–$C_4$)alkyl, (c) a 4- to 7-membered heterocyclic ring containing either from 1 to 3 N hetero-atoms or one N hetero-atom and one O or one S hetero-atom, said ring being optionally benzo-fused and optionally substituted, including in the benzo-fused portion, by $C_1$–$C_6$ alkyl, hydroxy, hydroxy($C_1$–$C_4$)alkyl, —$OR^8$, $R^8O$ ($C_1$–$C_4$)alkyl, halo, halo($C_1$–$C_4$)alkyl, —$S(O)_mR^8$, $R^8S(O)_m$($C_1$–$C_4$)alkyl, oxo, N-cyanoimino, amino, amino($C_1$–$C_4$)alkyl, —$NHR^8$, $R^8NH$($C_1$–$C_4$)alkyl, —$N(R^8)_2$, $(R^8)_2N$($C_1$–$C_4$)alkyl, cyano, cyano ($C_1$–$C_4$)alkyl, —$CO_2R^8$, $R^8O_2C$($C_1$–$C_4$)alkyl, —$CONH_2$, $H_2NCO$($C_1$–$C_4$)alkyl, —$CONHR^8$, $R^8NHCO$($C_1$–$C_4$)alkyl, —$CON(R_8)_2$ or $(R^8)_2NCO$ ($C_1$–$C_4$)alkyl, or, as appropriate, a ring N- or S-oxide derivative of said heterocyclic ring, with the proviso that said heterocyclic ring is linked by a ring carbon atom when X is O, NH or S, or (d), when X is NH, a group of the formula:

wherein $R^6$ is —$OR^8$, —$NHR^8$, —$SR^8$, —NH(aryl) or —NH(pyridinyl) and $R^7$ is cyano, nitro or $C_2$–$C_6$ alkanoyl; and the dashed line, X, $R^2$, $R^3$ and $R^5$ are as defined in claim 1.

3. A compound as claimed in claim 1 wherein the dashed line does not represent a covalent bond; X is O, NH or a direct link; R and $R^1$ are each independently selected from H and $C_1$–$C_4$ alkyl;

$R^2$ is H or methyl;

$R^3$ is hydroxy;

$R^4$ is a group of the formula:

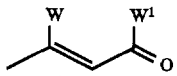

wherein W and $W^1$ taken together represent $C_1$–$C_4$ alkylene, a 6-membered heterocyclic ring containing 1 or 2 nitrogen heteroatoms and optionally substituted by $C_1$–$C_6$ alkyl, hydroxy, halo, $C_1$–$C_4$ alkylthio or oxo, or is a group of the formula:

wherein $R^6$ is —$OR^8$, —$NHR^8$ or —$SR^8$ and $R^7$ is cyano;

$R^5$ is aryl or $C_1$–$C_{12}$ alkyl, said $C_1$–$C_{12}$ alkyl being optionally substituted by hydroxy, —$OR^8$, $C_2$–$C_6$ alkanoyloxy, amino, —$CONHR^8$, —$CONH(C_1$–$C_6)$ alkyl$CO_2R^8$, —$CO_2R^9$, aryl, aryloxy, arylcarbonyloxy, aryl($C_1$–$C_6$)alkoxy, phthalimido, or a group of the formula:

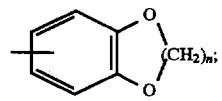

$R^8$ is methyl or ethyl;

$R^9$ is indanyl, aryl, $C_1$–$C_{12}$ alkyl or $C_2$–$C_{12}$ alkenyl, said $C_1$–$C_{12}$ alkyl being optionally substituted by halo, $C_2$–$C_6$ alkanoyloxy, —$OCO_2R^8$ or aryl;

"aryl" means phenyl optionally substituted by $C_1$–$C_6$ alkyl, hydroxy, —$OR^8$, halo or aryl($C_1$–$C_6$)alkoxy;

m is O; and n is 1.

4. A compound as claimed in claim 3 wherein R and $R^1$ are each $C_1$–$C_4$ alkyl;

$R^4$ is 1-oxocyclopent-2-en-3-yl, 2-oxo-1,2-dihydropyridin-1-yl, 2-oxo-1H-1,2-dihydropyridin-4-yl, 2-oxopiperidin-1-yl, 3-hydroxypyridazin-6-yl, 2-methyl-3-oxopyridazin-6-yl, 4-chloropyrimidin-2-yl, 2-chloropyrimidin-4-yl, 2-methylthiopyrimidin-4-yl or is a group of the formula:

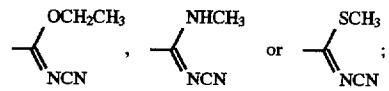

$R^5$ is phenyl or $C_1$–$C_4$ alkyl, said $C_1$–$C_4$ alkyl being optionally substituted by hydroxy, methoxy, acetoxy, amino, methylaminocarbonyl, N-(ethoxycarbonylmethyl)carbamoyl, —$CO_2R^9$, phenyl, methylphenyl, methoxyphenyl, hydroxyphenyl, halophenyl, benzyloxyphenyl, phenoxy, benzoyloxy, benzyloxy, phthalimido, or a group of the formula:

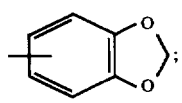

and R⁹ and R⁹ᴬ are each independently indanyl, phenyl, C₁–C₄ alkyl or vinyl, said C₁–C₄ alkyl being optionally substituted by fluoro, pivaloyloxy, ethoxycarbonyloxy or phenyl.

5. A compound as claimed in claim 4 wherein

R⁵ is phenyl, methyl, ethyl, n-propyl, 2-hydroxyethyl, 2-methoxyethyl, 2-acetoxyethyl, 2-aminoethyl, 2-(methylaminocarbonyl)ethyl, N-(ethoxycarbonylmethyl)carbamoylmethyl, ethoxycarbonylmethyl, 3-methoxycarbonylprop-1-yl, 3-ethoxycarbonylprop-1-yl, 4-ethoxycarbonylbut-1-yl, 3-vinyloxycarbonylprop-1-yl, 3-(2,2,2-trifluoroethoxycarbonyl)prop-1-yl, 3-(ethoxycarbonyloxymethoxycarbonyl)prop-1-yl, 3-(pivaloyloxymethoxycarbonyl)prop-1-yl, 3-phenoxycarbonylprop-1-yl, 3-benzyloxycarbonylprop-1-yl, 3-(5-indanyloxycarbonyl)prop-1-yl, benzyl, 2-phenylethyl, 3-phenylprop-1-yl, 4-phenylbut-1-yl, 2-(2-methylphenyl)ethyl, 2-(3-methylphenyl)ethyl, 2-(4-methylphenyl)ethyl, 2-(2-methoxyphenyl)ethyl, 2-(3-methoxyphenyl)ethyl, 2-(4-methoxyphenyl)ethyl, 2-(4-hydroxyphenyl)ethyl, 2-(4-fluorophenyl)ethyl, 2-(4-benzyloxyphenyl)ethyl, 2-phenoxyethyl, 2-benzoyloxyethyl, 2-benzyloxyethyl, 2-phthalimidoethyl or 2-(1,3-benzodioxolan-5-yl)-ethyl;

and R⁹ and R⁹ᴬ are each independently 5-indanyl, phenyl, methyl, ethyl, vinyl, 2,2,2-trifluoroethyl, pivaloyloxymethyl, ethoxycarbonyloxymethyl or benzyl.

6. A compound as claimed in claim 5 wherein

R and R¹ are each methyl; R² is methyl; and R⁵ is methyl, ethyl, n-propyl, 3-ethoxycarbonylprop-1-yl, 4-ethoxycarbonylbut-1-yl or 2-phenylethyl.

7. A compound selected from the group:

4-(2-chloropyrimidin-4-yl)amino-3,4-dihydro-6-(1-[3-ethoxycarbonylprop-1-yl]-1H-tetrazol-5-yl)-3-hydroxy-2,2,3-trimethyl-2H-benzo[b]pyran;

3,4-dihydro-6-(1-[3-ethoxycarbonylprop-1-yl]-1H-tetrazol-5-yl)-3-hydroxy-4-(3-hydroxypyridazin-6-yl)oxy-2,2,3-trimethyl-2H-benzo[b]pyran;

3,4-dihydro-6-(1-[4-ethoxycarbonylbut-1-yl]-1H-tetrazol-5-yl)-3-hydroxy-4-(3-hydroxypyridazin-6-yl)oxy-2,2,3-trimethyl-2H-benzo[b]pyran;

3,4-dihydro-6-(1-[3-ethoxycarbonylprop-1-yl]-1H-tetrazol-5-yl)-3-hydroxy-4-(2-methyl-3-oxopyridazin-6-yl)oxy-2,2,3-trimethyl-2H-benzo[b]pyran;

3,4-dihydro-2,2-dimethyl-3-hydroxy-4-(2-oxopiperidin-1-yl)-6-(1-[2-phenylethyl]-1H-tetrazol-5-yl)-2H-benzo-[b]pyran;

3,4-dihydro-6-(1-[3-ethoxycarbonylprop-1-yl]-1H-tetrazol-5-yl)-3-hydroxy-4-(2-oxo-1H-1,2-dihydropyridin-4-yl)oxy-2,2,3-trimethyl-2H-benzo[b]pyran;

3,4-dihydro-3-hydroxy-4-(3-hydroxypyridazin-6-yl)oxy-6-(1-[2-phenylethyl]-1H-tetrazol-5-yl)-2,2,3-trimethyl-2H-benzo[b]pyran:

or a pharmaceutically acceptable salt of any of these compounds.

8. A compound as claimed in claim 1 of the formula:

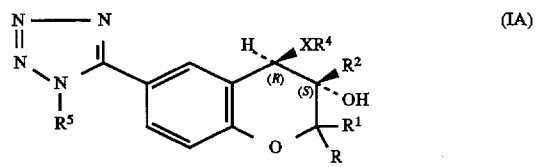

wherein X is O or NH; R and R¹ are each C₁–C₄ alkyl; R² is H or C₁–C₄ alkyl; and R⁴ and R⁵ are as defined in claim 1.

9. A pharmaceutical composition comprising a compound of the formula (I) or a pharmaceutically acceptable salt thereof, as claimed in claim 1, together with a pharmaceutically acceptable diluent or carrier.

10. A method of treatment of a human to treat angina or a disease associated with the altered tone and/or motility of smooth muscle which comprises administering to said human an effective amount of a compound of the formula (I) or a pharmaceutically acceptable salt or composition thereof, as claimed in claim 1.

11. A method as claimed in claim 10 where the disease is chronic obstructive airways disease, asthma, urinary incontinence, irritable bowel syndrome, diverticular disease, oesophageal achalasia or hypertension.

12. A compound of the formula:

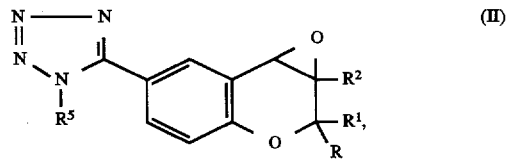

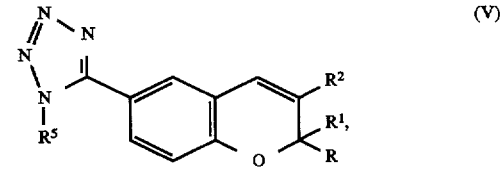

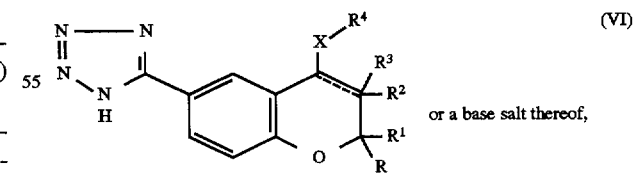

or a base salt thereof,

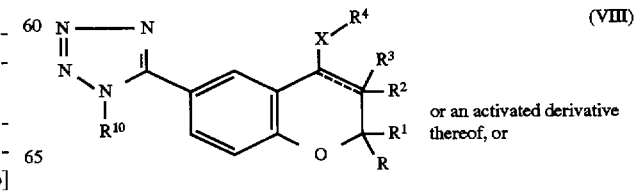

or an activated derivative thereof, or

-continued

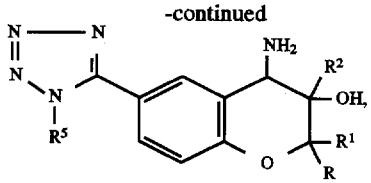

(IX)

wherein $R^{10}$ is aryl, $C_1$–$C_{12}$ alkyl, $C_2$–$C_{12}$ alkenyl or $C_2$–$C_{12}$ alkynyl, said alkyl, alkenyl and alkynyl being substituted by —$CO_2H$ or by aryl substituted by —$CO_2H$ or $HO_2C(C_1$–$C_6)$ alkyl, and said aryl being substituted by —$CO_2H$ or $HO_2C(C_1$–$C_6)$ alkyl, and the dashed line, X, R, $R^1$, $R^2$, $R^3$, $R^4$, $R^5$ and "aryl" are as defined in claim 1.

13. A compound as claimed in claim 7, or a pharmaceutically acceptable salt thereof, having the 3S,4R- form.

* * * * *